(12) United States Patent  
Reiter et al.

(10) Patent No.: US 8,747,855 B2  
(45) Date of Patent: Jun. 10, 2014

(54) ANTI HUMAN IMMUNODEFICIENCY ANTIBODIES AND USES THEREOF

(75) Inventors: Yoram Reiter, Haifa (IL); Maya Haus-Cohen, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 338 days.

(21) Appl. No.: 12/935,286

(22) PCT Filed: Apr. 5, 2009

(86) PCT No.: PCT/IL2009/000379
§ 371 (c)(1),
(2), (4) Date: Sep. 29, 2010

(87) PCT Pub. No.: WO2009/125394
PCT Pub. Date: Oct. 15, 2009

(65) Prior Publication Data
US 2011/0020357 A1    Jan. 27, 2011

Related U.S. Application Data

(60) Provisional application No. 61/071,043, filed on Apr. 9, 2008.

(51) Int. Cl.
C07K 16/10   (2006.01)
C07H 21/04   (2006.01)
G01N 33/536  (2006.01)
A61K 39/42   (2006.01)

(52) U.S. Cl.
USPC ...... 424/148.1; 424/139.1; 435/5; 435/320.1; 530/387.1; 530/387.3; 530/387.9; 530/388.35; 536/23.53

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 5,591,829 A | 1/1997 | Matsushita |
| 5,695,928 A | 12/1997 | Stewart et al. |
| 5,952,471 A | 9/1999 | Griffiths Lawson |
| 6,054,297 A | 4/2000 | Carter et al. |
| 6,232,445 B1 | 5/2001 | Rhode et al. |
| 6,291,160 B1 | 9/2001 | Lerner et al. |
| 6,342,221 B1 | 1/2002 | Thorpe et al. |
| 6,416,738 B1 | 7/2002 | Theodore et al. |
| 6,468,983 B2 | 10/2002 | Silverman et al. |
| 6,992,176 B2 | 1/2006 | Reiter et al. |
| 7,632,923 B2 | 12/2009 | Reiter et al. |
| 7,718,777 B2 | 5/2010 | Hoogenboom et al. |
| 2003/0129191 A1 | 7/2003 | Theodore et al. |
| 2003/0165993 A1 | 9/2003 | Buechler et al. |
| 2003/0175772 A1 | 9/2003 | Wang |
| 2003/0223994 A1 | 12/2003 | Hoogenboom et al. |
| 2004/0191260 A1 | 9/2004 | Reiter et al. |
| 2005/0152912 A1 | 7/2005 | Reiter et al. |
| 2005/0250833 A1 | 11/2005 | Attali et al. |
| 2005/0255101 A1 | 11/2005 | Reiter et al. |
| 2005/0287141 A1 | 12/2005 | Reiter |
| 2006/0079471 A1 | 4/2006 | Michaeli |
| 2006/0083735 A1 | 4/2006 | Reiter et al. |
| 2007/0196369 A1 | 8/2007 | Hoogenboom et al. |
| 2010/0080805 A1 | 4/2010 | Reiter et al. |
| 2010/0228007 A1 | 9/2010 | Hoogenboom et al. |
| 2011/0293616 A1 | 12/2011 | Reiter et al. |
| 2011/0318369 A1 | 12/2011 | Reiter et al. |

FOREIGN PATENT DOCUMENTS

| | | | |
|---|---|---|---|
| EP | 1178116 | 2/2002 | |
| JP | 11-510375 | 9/1999 | |
| WO | WO 91/12332 | 8/1991 | |
| WO | WO 95/29193 | 11/1995 | |
| WO | WO 97/02342 | 1/1997 | |
| WO | WO 97/41440 | 11/1997 | |
| WO | WO 9949893 A1 * | 10/1999 | ........... A61K 39/385 |
| WO | WO9949893 A1 * | 10/1999 | |
| WO | WO 00/25813 | 5/2000 | |
| WO | WO 01/72768 | 10/2001 | |
| WO | WO 01/96401 | 12/2001 | |
| WO | WO 03/068201 | 8/2003 | |
| WO | WO 03/070752 | 8/2003 | |
| WO | WO 2004/069148 | 8/2004 | |
| WO | WO 2004/084798 | 10/2004 | |
| WO | WO 2006/103429 | 10/2006 | |
| WO | WO 2007/030167 | 3/2007 | |
| WO | WO 2009/125394 | 10/2009 | |
| WO | WO 2009/125395 | 10/2009 | |
| WO | WO 2009125395 | 10/2009 | |

OTHER PUBLICATIONS

Lu et al. A fully Human Recombinant IgG-like Bispecific Antibody to Both the Epidermal Growth Factor Receptor and the Insulin-like Growth Factor Receptor for Enhanced Antitumor Activity. The Jounal of Biological Chemistry 2005, vol. 280, No. 20, pp. 19665-19672.*

Denkberg et al. Recombinant human single-chain MHC-peptide complexes made from E. coli by in vitro refolding: functional single-chain MHC-peptide complexes and tetramers with tumor associated antigens. European Journal of Immunology 2000, vol. 30, pp. 3522-3532.*

(Continued)

Primary Examiner — Louise Humphrey

(57) ABSTRACT

Provided are antibodies comprising an antigen recognition domain capable of binding an MHC molecule being complexed with a human immunodeficiency virus (HIV) peptide, wherein the antibody does not bind the MHC molecule in an absence of the complexed peptide, and wherein the antibody does not bind the peptide in an absence of the MHC molecule. Also provided are methods of using same for diagnosing HIV infection and treating AIDS.

11 Claims, 15 Drawing Sheets
(12 of 15 Drawing Sheet(s) Filed in Color)

(56) References Cited

OTHER PUBLICATIONS

Restriction Official Action Dated Dec. 13, 2011 From the US Patent and Trademark Office Re. U.S. Appl. No. 13/163,701.
Office Action Dated Dec. 13, 2010 From the Israeli Patent Office Re.: Application No. 162952 and Its Translation Into English.
Office Action Dated Dec. 14, 2010 From the Israel Patent Office Re.: Application No. 193376 and Its Translation Into English.
Response Dated Dec. 20, 2010 to Requisition by the Examiner of Jun. 22, 2010 From the Canadian Intellectual Property Office Re. Application No. 2,476,625.
Response Dated Sep. 21, 2010 to Office Action of Feb. 21, 2010 From the Israeli Patent Office Re.: Application No. 170951.
Boder et al. "Yeast Surface Display for Screening Combinatorial Polypeptide Libraries", Nature Biotechnology, 15: 553-557, Jun. 1997.
Notice of Appeal Re. Response Dated Jan. 19, 2011 to Official Action of Jul. 20, 2010 From the Patent and Trademark Office Re.: U.S. Appl. No. 11/203,137.
Communication Pursuant to Article 94(3) EPC Dated Feb. 1, 2012 From the European Patent Office Re. Application No. 10011766.2.
Notice of Allowance Dated Aug. 23, 2005 From the US Patent and Trademark Office Re.: U.S. Appl. No. 10/073,301.
International Search Report Dated Nov. 15, 2005 From the International Searching Authority Re. Application No. PCT/IL04/00108.
Official Action Dated Feb. 7, 2012 From the US Patent and Trademark Office Re. U.S. Appl. No. 13/163,701.
Requisition by the Examiner Dated Feb. 14, 2012 From the Canadian Intellectual Property Office Re. Application No. 2,476,625.
Requisition by the Examiner Dated Aug. 9, 2010 From the Canadian Intellectual Property Office Re. Application No. 2,474,782.
Response Dated Feb. 8, 2011 to Requisition by the Examiner of Aug. 9, 2010 From the Canadian Intellectual Property Office Re. Application No. 2,474,782.
Communication Under Rule 71(3) EPC Dated Feb. 22, 2012 From the European Patent Office Re. Application No. 09001632.0.
Official Action Dated Apr. 20, 2012 From the US Patent and Trademark Office Re. U.S. Appl. No. 12/591,421.
Official Action Dated Apr. 25, 2012 From the US Patent and Trademark Office Re. U.S. Appl. No. 12/591,336.
Ding et al. "Four A6-TCR/Peptide/HLA-A2 Structures That Generate Very Different T Cell Signals Are Nearly Identical", Immunity, 11: 45-56, Jul. 1999.
Communication Pursuant to Rule 69 EPC—Reminder Concerning Payment of the Designation Fees (Art. 79(2) EPC) and of the Examination Fee (Art.94(1) EPC)—and Invitation Pursuant to Rule 70a(1) EPC Dated Sep. 27, 2011 From the European Patent Office Re. Application No. 09001632.0.
Response Dated Mar. 17, 2011 to Communication Pursuant to Rule 69 EPC—Reminder Concerning Payment of the Designation Fees (Art. 79(2) EPC) and of the Examination Fee (Art.94(1) EPC)—and Invitation Pursuant to Rule 70a(1) EPC of Sep. 27, 2011 From the European Patent Office Re. Application No. 09001632.0.
Response Dated Apr. 13, 2011 to Office Action of Dec. 13, 2010 From the Israeli Patent Office Re.: Application No. 162952.
Response Dated Apr. 14, 2011 to Office Action of Dec. 14, 2010 From the Israel Patent Office Re.: Application No. 193376.
Altman et al. "Formation of Functional Peptide Complexes of Class II Major Histocompatibility Complex Proteins From Subunits Produced in *Escherichia coli*", Proc. Nat. Acad. Sci. USA, 90: 10330-10334, 1993.
Brinkmann et al. "B3(Fv)-PE38KDEL, A Single-Chain Immunotoxin That Causes Complete Regression of a Human Carcinoma in Mice", Proc. Natl. Acad. Sci. USA, 88: 8616-8620, Oct. 1991.
Cox et al. "Identification of a Peptide Recognized by Five Melanoma-Specific Human Cytotoxic T Cell Lines", Science, 264(5159): 716-719, 1994.
Garboczi et al. "HLA-A2-Peptide Complexes: Refolding and Crystallization of Molecules Expressed in *Escherichia coli* and Complexed With Single Antigenic Peptides", Proc. Natl. Acad. Sci. USA, XP002131069, 89: 3429-3433, 1992.
Lee et al. "Functional Cell Surface Expression by a Recombinant Single-Chain Class I Major Histocompatibility Complex Molecule With a Cis-Active Beta 2-Microglobulin Domain", European Journal of Immunology, 24(11): 2633-2639, 1994.
Lone et al. "In Vitro Induction of Specific Cytotoxic T Lymphocytes Using Recombinant Single-Chain MHC Class I/Peptide Complexes", Journal of Immunotherapy, 21(4): 283-94, 1998.
Mage et al. "A Recombinant, Soluble, Single-Chain Class 1 Major Histocompatibility Complex Molecule with Biological Activity", Proc. Natl. Acad. Sci. USA, PNAS, 89: 10658-10662, 1992.
Matsumura et al. "In Vitro Peptide Binding to Soluble Empty Class I Major Histocompatibility Complex Molecules Isolated From Transfected *Drososphila melanogaster* Cells", Journal of Biological Chemistry, 267(33): 23589-23595, 1992.
Mottez et al. "Cells Expressing a Major Histocompatibility Complex Class I Molecule With a Single Covalently Bound Peptide Are Highly Immunogenic", Journal of Experimental Medicine, XP000654243, 181(2): 493-502, 1995.
Renkvist et al. "A Listing of Human Tumor Antigens Recognized by T Cells", Cancer Immunology and Immunotherapy, XP002274524, 50(1): 3-15, 2001.
Uger et al. "Creating CTL Targets With Epitope-Linked Beta 2-Microglobulin Constructs", Journal of Immunology, XP002115504, 160(4): 1598-1605, Feb. 15, 1998.
White et al. "Soluble Class I MHC With Beta2-Microglobulin Covalently Linked Peptides: Specific Binding to A T Cell Hybridoma", The Journal of Immunology, 162: 2671-2676, 1999.
European Search Report and the European Search Opinion Dated May 4, 2011 From the European Patent Office Re. Application No. 10011766.2.
Official Action Dated May 17, 2011 From the US Patent and Trademark Office Re. U.S. Appl. No. 12/724,486.
Hoogenboom "Designing and Optimizing Library Selection Strategies for Generating High-Affinity Antibodies", Trends in Biotechnology, XP004034115, 15(2): 62-70, Feb. 1, 1997.
Michaeli et al. "Expression Hierarchy of T Cell Epitopes From Melanoma Differentiation Antigens: Unexprected High Level Presentation of Tyrosinase-HLA-A2 Complexes Revealed by Peptide-Specific, MHC-Restricted, TCR-Like Antibodies", The Journal of Immunology, XP007918402, 182(10): 6328-6341, May 15, 2009.
Benhar et al. "Phage Display of Single Chain Antibody Constructs", Current Protocols in Immunology, Chap.10(Unit 10.19B), May 2002.
Berdichevsky et al. "Phage Display of a Cellulose Binding Domain From *Clostridium thermocellum* and Its Application as a Tool for Antibody Engineering", Journal of Immunological Methods, 228: 151-162, 1999.
Esche et al. "The Use of Dendritic Cells for Cancer Vaccination", Current Opinion in Molecular Therapeutics, 10): 72-81, Feb. 1999. Abstract.
Ignatowicz et al. "Cell Surface Expression of Class II MHC Proteins Bound by a Single Peptide", The Journal of Immunology, 154: 3852-3862, 1995.
Ignatowicz et al. "The Repertoire of T Cells Shaped by a single MHC/Peptide Ligand", Cell, 84: 521-529, Feb. 23, 1996.
Kawakami et al. "Recognition of Multiple Epitopes in the Human Melanoma Antigen Gp100 by Tumor-Infiltrating T Lymphocytes Associated With In Vivo Tumor Regression", The Journal of Immunology, 154: 3961-3968, 1995.
Kozono et al. "Production of Soluble MHC Class II Proteins With Covalently Bound Single Peptides", Nature, 369: 151-154, May 12, 1994.
Stern et al. "The Human Class II MHC Protein HLA-DR1 Assembles as Empty AlphaBeta Heterodimers in the Absence of Antigenic Peptide", Cell, 68: 465-477, Feb. 7, 1992.
Office Action Dated May 13, 2012 From the Israel Patent Office Re.: Application No. 193376 and Its Translation Into English.
Pastan "Targeted Therapy of Cancer With Recombinant Immunotoxins", Biochimica et Biophysica Acta, 1333(2): C1-C6, 1997.

(56) References Cited

OTHER PUBLICATIONS

Requisition by the Examiner Dated May 4, 2011 From the Canadian Intellectual Property Office Re. Application No. 2,474,782.
Communication Pursuant to Rules 70(2) and 70a(2) EPC and Reference to Rule 39(1) EPC Dated Jun. 14, 2011 From the European Patent Office Re. Application No. 10011766.2.
Translation of Decision of Refusal Dated Jun. 13, 2011 From the Japanese Patent Office Re. Application No. 2003-569659.
Invitation Pursuant to Article 94(3) and Rule 71(1) EPC Dated Jul. 26, 2011 From the European Patent Office Re. Application No. 09001632.0.
Response Dated Aug. 7, 2011 to Invitation Pursuant to Article 94(3) and Rule 71(1) EPC of Jul. 26, 2011 From the European Patent Office Re. Application No. 09001632.0.
Official Action Dated Aug. 7, 2012 From the US Patent and Trademark Office Re. U.S. Appl. No. 13/163,701.
Requisition by the Examiner Dated Jul. 6, 2012 From the Canadian Intellectual Property Office Re. Application No. 2,474,782.
Rhode et al. "Single-Chain MHC Class II Molecules Induce T Cell Activation and Adoptosis", The Journal of Immunology, 157: 4885-4891, 1996.
Communication Pursuant to Article 94(3) EPC Dated May 13, 2011 From the European Patent Office Re. Application No. 09729769.1.
Official Action Dated Aug. 9, 2011 From the US Patent and Trademark Office Re. U.S. Appl. No. 12/724,486.
Communication Pursuant to Article 94(3) EPC Dated Sep. 16, 2011 From the European Patent Office Re. Application No. 03742843.0.
Official Action Dated Sep. 6, 2011 From the US Patent and Trademark Office Re. U.S. Appl. No. 12/591,336.
Response Dated Sep. 13, 2011 to Invitation Pursuant to Article 94(3) and Rule 71(1) EPC of Jul. 26, 2011 From the European Patent Office Re. Application No. 09001632.0.
Hildreth "Syncytium-Inhibiting Monoclonal Antibodies Produced Against Human T-Cell Lymphotropic Virus Type 1-Infected Cells Recognize Class II Major Histocompatibility Complex Molecules and Block by Protein Crowding", Journal of Virology, 72(12): 9544-9552, Dec. 1998.
Restriction Official Action Dated Sep. 25, 2012 From the US Patent and Trademark Office Re. U.S. Appl. No. 12/936,518.
Gould et al. "Characterization of Two Distinct Major Histocompatibility Complex Class I Kk-Restricted T-Cell Epitopes Within the Influenza A/PR/8/34 Virus Hemagglutinin", Journal of Virology, 65(10): 5401-5409, Oct. 1991.
International Preliminary Report on Patentability Dated Oct. 21, 2010 From the International Bureau of WIPO Re. Application No. PCT/IL2009/000379.
International Preliminary Report on Patentability Dated Oct. 21, 2010 From the International Bureau of WIPO Re. Application No. PCT/IL2009/000380.
Official Action Dated Oct. 23, 2012 From the Patent and Trademark Office Re.: U.S. Appl. No. 12/591,421.
Reynhardt et al. "Biacore's SPR Technology in a GMP-Regulated Environment", Biacore Journal, 1: 12-14, 2001.
Response Dated Nov. 3, 2011 to Requisition by the Examiner of May 4, 2011 From the Canadian Intellectual Property Office Re. Application No. 2,474,782.
Decision of Refusal Dated Jun. 13, 2011 From the Japanese Patent Office Re. Application No. 2003-569659 and its Translation Into English.
International Search Report and the Written Opinion Dated Apr. 15, 2005 From the International Searching Authority Re: Application No. PCT/IL04/00275.
International Search Report Dated Jul. 23, 2003 From the International Searching Authority Re: Application No. PCT/IL03/00105.
International Search Report Dated Jul. 31, 2009 From the International Searching Authority Re.: Application No. PCT/IL2009/000379.
Official Action Dated Sep. 10, 2004 From the US Patent and Trademark Office Re. U.S. Appl. No. 10/396,578.

Supplementary European Search Report Dated Aug. 22, 2005 From the European Patent Office Re. Application No. 03706876.4.
Written Opinion Dated Jan. 4, 2005 From the International Searching Authority Re: Application No. PCT/IL03/00105.
Written Opinion Dated Jul. 31, 2009 From the International Searching Authority Re.: Application No. PCT/IL2009/000379.
Anikeeva et al. "Soluble HIV-Specific T Cell Receptor: Expression, Purification and Analysis of the Specificity", Journal of Immunological Methods, XP004430548, 277(1-2): 75-86, Jun. 1, 2003.
Polakova et al. "Antibodies Directed Against the MHC-I Molecule H-2Dd Complexed With an Antigenic Peptide: Similarities to A T Cell Receptor With the Same Specificity", The Journal of Immunology, XP002986050, 165(10): 5703-5712, Nov. 1, 2000. Figs.1-8.
Examiner's Report Date Aug. 24, 2009 From the Australian Government, IP Australia Re.: Application No. 2008201062.
Pascolo et al. "HLA-A2.1-Restricted Education and Cytolytic Activity of CD8+ T Lymphocytes From $\beta 2$ Microglobulin ($\beta 2m$) HLA-A2.1 Monochain Transgenic H-2Db $\beta 2m$ Double Knockout Mice", Journal of Experimental Medicine, 185(12): 2043-2051, 1977.
Wülfing et al. "Correctly Folded T-Cell Receptor Fragments in the Periplasm of *Escherichia coli*", Journal of Molecular Biology, 242(5): 655-669, 1994. Abstract.
Yamano et al. "Detection of HTLV-I Tax11-19 Peptide/HLA-A*201 Complexes are Overexpressed in HAM/TSP Patients", Aids Research and Human Retroviruses, 19(Suppl.): S-38, 2003. Abstract. & 11th International Conference on Human Retrovirology: HTLV and Related Viruses, San Francisco, USA, 2003. Abstract.
Yamano et al. "Increased Expression of Human T Lymphocyte Virus Type I (HTLV-I) Tax11-19 Peptide-Human Histocompatibility Leukocyte Antigen A*201 Complexes on CD4+ CD25+ T Cells Detected by Peptide-Specific, Major Histocompatibility Complex-Restricted Antibodies in Patients With HTLV-I-Associated Neurological Disease", Journal of Experimental Medicine, 199(10): 1367-1377, 2004.
Restriction Official Action Dated Nov. 10, 2011 From the US Patent and Trademark Office Re. U.S. Appl. No. 12/591,421.
Response Dated Dec. 5, 2011 to Restriction Official Action of Nov. 10, 2011 From the US Patent and Trademark Office Re. U.S. Appl. No. 12/591,421.
Response Dated Dec. 6, 2011 to Communication Pursuant to Rules 70(2) and 70a(2) EPC and Reference to Rule 39(1) EPC of Jun. 14, 2011 From the European Patent Office Re. Application No. 10011766.2.
Communication Under Rule 71(3) EPC Dated Dec. 7, 2012 From the European Patent Office Re. Application No. 10011766.2.
Official Action Dated Apr. 4, 2008 From the US Patent and Trademark Office Re.: U.S. Appl. No. 10/544,066.
Official Action Dated Apr. 4, 2011 From the US Patent and Trademark Office Re.: U.S. Appl. No. 10/544,066.
Official Action Dated Sep. 19, 2011 From the US Patent and Trademark Office Re.: U.S. Appl. No. 10/544,066.
Official Action Dated Jul. 20, 2010 From the US Patent and Trademark Office Re.: U.S. Appl. No. 10/544,066.
Response Dated Jun. 16, 2011 to Official Action of May 17, 2011 From the US Patent and Trademark Office Re. U.S. Appl. No. 12/724,486.
Response Dated Jan. 19, 2011 to Official Action of Jul. 20, 2010 From the US Patent and Trademark Office Re.: U.S. Appl. No. 10/544,066.
Response Dated Jun. 27, 2011 to Official Action of Apr. 4, 2011 From the US Patent and Trademark Office Re.: U.S. Appl. No. 10/544,066.
Downward "Science, Medicine, and the Future. RNA Interference", BMJ, 328: 1245-1248, 2004.
Dunbar et al. "The U14 SnoRNA is Required for 2'-O-Methylation of the Pre-18S rRNA in *Xenopus* Oocytes", RNA, 4: 195-204, 1998.
Gupta et al. "Small Nucleolar RNA Interference in *Trypanosoma brucei*: Mechanism and Utilization for Elucidating the Function of SnoRNAs", Nucleic Acids Research, 38(20): 7236-7247, Jul. 3, 2010.
Hammond et al. "Post-Transcriptional Gene Silencing by Double-Stranded RNA", Nature Reviews: Genetics, 2: 110-119, 2001.
Kedde et al. "Telomerase-Independent Regulation of ATR by Human Telomerase RNA", Journal of Biological Chemistry, 281(52): 40503-40514, Dec. 29, 2006.

(56) References Cited

OTHER PUBLICATIONS

Kosciolek et al. "Inhibition of Telomerase Activity in Human Cancer Cells by RNA Interference", Molecular Cancer Therapeutics, 2: 209-216, 2003.
Liang et al. "Small Nucleolar RNA Interference Induced by Antisense or Double-Stranded RNA in Trypanosomatids", Proc. Natl. Acad. Sci. USA, 100(13): 7521-7526, 2003.
Lu et al. "Delivering SiRNA In Vivo for Functional Genomics and Novel Therapeutics", RNA Interference Technology, p. 303-317, 2005.
Paul et al. "Effective Exprssion of Small Interfering RNA in Human Cells", Nature Biotechnology, 20: 505-508, 2002.
Protocol Online "What is Antisense Phosphorothioate Oligonucleotides?", Current Protocols, Protocol Online, Oct. 14, 2006.
Samarsky et al. "RNAi in Drug Development: Practical Considerations", RNA Interference Technology, p. 384-395, 2005.
Zhang et al. "Antisense Telomerase RNA Induced Human Gastric Cancer Cell Apoptosis", Worl Journal of Gastroenterology, 6(3): 430-432, 2000.
Communication Pursuant to Article 94(3) EPC Dated Feb. 7, 2013 From the European Patent Office Re. Application No. 03742843.0.
Official Action Dated Jun. 24, 2013 From the US Patent and Trademark Office Re. U.S. Appl. No. 12/936,518.
Reche et al. "Sequence Variability Analysis of Human Class I and Class II MHC Molecules: Functional and Structural Correlates of Amino Acid Polymorphisms", Journal of Molecular Biology, 331(3): 623-641, Aug. 15, 2003.
Applicant-Initiated Interview Summary Dated Apr. 18, 2013 From the US Patent and Trademark Office Re. U.S. Appl. No. 12/591,421.
Official Action Dated Apr. 23, 2013 From the US Patent and Trademark Office Re. U.S. Appl. No. 12/724,486.
Communication Pursuant to Article 94(3) EPC Dated Mar. 6, 2013 From the European Patent Office Re. Application No. 09731417.3.
Requisition by the Examiner Dated Jan. 8, 2013 From the Canadian Intellectual Property Office Re. Application No. 2,476,625.
Communication of a Notice of Opposition Dated May 22, 2013 From the European Patent Office Re. Application No. 09001632.0.
Communication of a Notice of Opposition I Dated May 21, 2013 From the European Patent Office Re. Application No. 09001632.0.
Communication of a Notice of Opposition II Dated May 21, 2013 From the European Patent Office Re. Application No. 09001632.0.
Boder et al. "Directed Evolution of Antibody Fragments With Monovalent Femtomolar Antigen-Binding Affinity", Proc. Natl. Acad. Sci. USA, PNAS, 97(20): 10701-10705, Sep. 26, 2000.
Foote et al. "Breaking the Affinity Ceiling for Antibodies and T Cell Receptors", Proc. Natl. Acad. Sci. USA, PNAS, 97(20): 10679-10681, Sep. 26, 2000.
Gram et al. "In Vitro Selection and Affinity Maturation of Antibodies From a Naive Combinatorial Immunoglobulin Library", Proc. Natl. Acad. Sci. USA, 89: 3576-3580, Apr. 1992.
Holler et al. "In Vitro Evolution of A T Cell Receptor With High Affinity for Peptide/MHC", Proc. Natl. Acad. Sci. USA, PNAS, 97(10): 5387-5392, May 9, 2000.
Kao et al. "Quantitative Analysis of Platelet Surface HLA by W6/32 Anti-HLA Monoclonal Antibody", Blood, 68(3): 627-632, 1986.
Madden et al. "The Antigenic Identity of Peptide-MHC Complexes: A Comparison of the Conformations of Five Viral Peptides Presented by HLA-A2", Cell, 75: 693-708, Nov. 19, 1993.
Pini et al. "Design and Use of a Phage Display Library", The Journal of Biological Chemistry, 273(34): 21769-21776, Aug. 21, 1998.
Pini et al. "Hierarchical Affinity Maturation of a Phage Library Derived Antibody for the Elective Removal of Cytomegalovirus From Plasma", Journal of Immunological Methods, 206: 171-182, 1997.
Schier et al. "Isolation of Picomolar Affinity Anti-C-ErbB-2 Single-Chain Fv by Molecular Evolution of the Complementarity Determining Regions in the Center of the Antibody Binding Site", The Journal of Molecular Biology, 263: 551-567, 1996.
Uchanska-Ziegler et al. "Soluble T Cell Receptor-Like Properties of an HLA-B35-Specific Monoclonal Antibody (TUE165)", European Journal of Immunology, 23: 734-738, 1993.
Willemsen et al. "A Phage Display Selected Fab Fragment With MHC Class I-Restricted Specificity for MAGE-A1 Allows for Retargeting of Primary Human T Lymphocytes", Gene Therapy, 8: 1601-1608, 2001.
Yang et al. "CDR Walking Mutagenesis for the Affinity Maturation of A Potent Human Anti-HIV-1 Antibody Into the Picomolar Range", The Journal of Molecular Biology, 254: 392-403, 1995.
Applicant-Initiated Interview Summary Dated Jan. 24, 2013 From the US Patent and Trademark Office Re. U.S. Appl. No. 12/591,421.
Official Action Dated Jan. 10, 2013 From the US Patent and Trademark Office Re. U.S. Appl. No. 12/936,518.
Rognan et al. "Modeling the Interactions of a Peptide-Major Histocompatibility Class I Ligand With Its Receptors. II. Cross-Reaction Between a Monoclonal Antibody and Two [Alpha][Beta] T Cell Receptors", Journal of Computer-Aided Molecular Design, 14: 71-82, 2000.
Communication Pursuant to Article 94(3) EPC Dated Jul. 7, 2010 From the European Patent Office Re.: Application No. 04723297.0.
Communication Pursuant to Article 94(3) EPC Dated Mar. 18, 2008 From the European Patent Office Re.: Application No. 04723297.0.
Communication Pursuant to Article 96(2) EPC Dated Nov. 15, 2005 From the European Patent Office Re.: Application No. 03706876.4.
Communication Pursuant to Article 96(2) EPC Dated Sep. 21, 2006 From the European Patent Office Re.: Application No. 03706876.4.
Definition "Fab", The Online Medical Dictionary, Retrieved From the Internet, Sep. 23, 2003.
European Search Report and the European Search Opinion Dated Aug. 24, 2010 From the European Patent Office Re. Application No. 09001632.0.
Examiner's Report Dated Aug. 24, 2009 From the Australian Government, IP Australia Re.: Application No. 2008201062.
International Preliminary Examination Report Dated Mar. 31, 2005 From the International Preliminary Examining Authority Re.: Application No. PCT/IL03/00105.
International Preliminary Report on Patentability Dated Oct. 13, 2005 From the International Bureau of WIPO Re.: Application No. PCT/IL2004/000275.
International Search Report Dated Aug. 7, 2009 From the International Searching Authority Re.: Application No. PCT/IL2009/000380.
International Search Report Dated Feb. 24, 2004 From the International Searching Authority Re.: PCT/US03/05128.
Invitation to Pay Additional Fees Dated Feb. 16, 2005 From the International Searching Authority Re.: Application No. PCT/IL04/00275.
Notice of Allowance Dated Aug. 4, 2009 From the US Patent and Trademark Office Re.: U.S. Appl. No. 11/074,803.
Notice of Allowance Dated Dec. 7, 2009 From the US Patent and Trademark Office Re.: U.S. Appl. No. 11/582,416.
Notice of Allowance Dated Aug. 11, 2009 From the US Patent and Trademark Office Re.: U.S. Appl. No. 10/510,229.
Office Action Dated Mar. 10, 2009 From the Israeli Patent Office Re.: Application No. 162952 and Its Translation Into English.
Office Action Dated Mar. 13, 2008 From the Israeli Patent Office Re.: Application No. 162952.
Office Action Dated Nov. 19, 2008 From the Israeli Patent Office Re.: Application No. 170951 and Its Translation Into English.
Office Action Dated Nov. 19, 2008 From the Israeli Patent Office Re.: Application No. 170951.
Office Action Dated Nov. 19, 2009 From the Israel Patent Office Re.: Application No. 162952 and Its Translation Into English.
Office Action Dated Nov. 19, 2009 From the Israel Patent Office Re.: Application No. 193376 and Its Translation Into English.
Office Action Dated Nov. 19, 2009 From the US Patent and Trademark Office Re.: Application No. 193376 and Its Translation Into English.
Office Action Dated Feb. 21, 2010 From the Israeli Patent Office Re.: Application No. 170951 and Its Translation Into English.
Official Action Dated Mar. 5, 2009 From the US Patent and Trademark Office Re.: U.S. Appl. No. 11/074,803.

(56) References Cited

OTHER PUBLICATIONS

Official Action Dated Oct. 9, 2007 From the US Patent and Trademark Office Re.: U.S. Appl. No. 10/510,229.
Official Action Dated Oct. 12, 2007 From the US Patent and Trademark Office Re.: U.S. Appl. No. 11/074,803.
Official Action Dated Jun. 13, 2008 From the Patent and Trademark Office Re.: U.S. Appl. No. 11/074,803.
Official Action Dated May 13, 2009 From the US Patent and Trademark Office Re.: U.S. Appl. No. 11/582,416.
Official Action Dated Sep. 13, 2006 From the US Patent and Trademark Office Re.: U.S. Appl. No. 11/074,803.
Official Action Dated Jun. 18, 2008 From the Patent and Trademark Office Re.: U.S. Appl. No. 10/510,229.
Official Action Dated Jul. 20, 2010 From the Patent and Trademark Office Re.: U.S. Appl. No. 11/203,137.
Official Action Dated Feb. 24, 2009 From the Patent and Trademark Office Re.: U.S. Appl. No. 10/510,229.
Official Action Dated Jan. 24, 2007 From the Patent and Trademark Office Re.: U.S. Appl. No. 10/510,229.
Official Action Dated Jan. 25, 2007 From the Patent and Trademark Office Re.: U.S. Appl. No. 11/074,803.
Official Action Dated Jul. 25, 2008 From the Patent and Trademark Office Re.: U.S. Appl. No. 11/203,137.
Official Action Dated Jan. 26, 2005 From the Patent and Trademark Office Re.: U.S. Appl. No. 10/073,301.
Official Action Dated Jan. 29, 2007 From the US Patent and Trademark Office Re.: U.S. Appl. No. 11/074,803.
Official Action Dated Jan. 29, 2009 From the US Patent and Trademark Office Re.: U.S. Appl. No. 11/582,416.
Requisition by the Examiner Dated Jun. 22, 2010 From the Canadian Intellectual Property Office Re. Application No. 2,476,625.
Response Dated Mar. 16, 2010 to Office Action of Nov. 19, 2009 From the Israel Patent Office Re.: Application No. 162952.
Response Dated Aug. 17, 2010 to Notification of Reason for Refusal of Jun. 2, 2010 From the Japanese Patent Office Re. Application No. 2003-569659.
Response Dated May 20, 2010 to Office Action of Nov. 19, 2009 From the US Patent and Trademark Office Re.: Application No. 193376.
Response Dated Aug. 23, 2010 to Examiner's Report of Aug. 24, 2009 From the Australian Government, IP Australia Re.: Application No. 2008201062.
Response Dated Jul. 28, 2010 to Notice of Reason for Rejection Dated Mar. 12, 2010 From the Japanese Patent Office Re.: Application No. 2006-507590.
Supplementary European Search Report Dated Jan. 11, 2008 From the European Patent Office Re.: Application No. 04723297.0.
Translation of Notice of Reason for Rejection Dated Nov. 7, 2008 From the Japanese Patent Office Re.: Application No. 2003-567383.
Translation of Notice of Reason for Rejection Dated Mar. 12, 2010 From the Japanese Patent Office Re.: Application No. 2006-507590.
Translation of Notice of Reason for Rejection Dated Jun. 13, 2008 From the Japanese Patent Office Re.: Application No. 2003-567383.
Translation of Notification of Reason for Refusal Dated Jun. 2, 2010 From the Japanese Patent Office Re. Application No. 2003-569659.
Written Opinion Dated Aug. 7, 2009 From the International Searching Authority Re.: Application No. PCT/IL2009/000380.
Aharoni et al. "Immunomodulation of Experimental Allergic Encephalomyelitis by Antibodies to the Antigen-Ia Complex", Nature, 351: 147-149, 1991.
Altman et al. "Phenotypic Analysis of Antigen-Specific T Lymphocytes", Science, 274(5284): 94-96, 1996.
Andersen et al. "A Recombinant Antibody With the Antigen-Specific, Major Histocompatibility Complex-Restricted Specifity of T Cells", Proc. Natl. Acad. Sci. USA, 93(5): 1820-1824, 1996.
Anichini et al. "Melanoma Cells and Normal Melanocytes Share Antigens Recognized by HLA-A2-Restricted Cytotoxic T Cell Clones From Melanoma Patients", The Journal of Experimental Medicine, 177: 989-998, 1993.
Anton et al. "MHC Class I-Associated Peptides Produced From Endogenous Gene Products With Vastly Different Efficiencies", The Journal of Immunology, 158: 2535-2542, 1997.
Arai et al. "Identification of Human Telomerase Reverse Transcriptase-Derived Peptides That Induce HLA-A24-Restricted Antileukemia Cytotoxic T Lymphocytes", Blood, 97(9): 2903-2907, 2001.
Bakker et al. "Melanocyte Lineage-Specific Antigen Gp100 is Recognized by Melanoma-Derived Tumor-Infiltrating Lymphocytes", The Journal of Experimental Medicine, 179: 1005-1009, 1994.
Biddison et al. "Tax and M1 Peptide/HLA-A2-Specific Fabs and T Cell Receptors Recognize Nonidentical Structural Features on Peptide/HLA-A2 Complexes", Journal of Immunology, 171(6): 3064-3074, 2003.
Bieganowska et al. "Direct Analysis of Viral-Specific CD8 T Cells With Soluble HLA-A2/Tax11-19 Tetramer Complexes in Patients With Human T-Cell Lymphotropic Virus-Associated Myelopathy", The Journal of Immunology, 162: 1765-1771, 1999.
Bird et al. "Single-Chain Antigen-Binding Proteins", Science, 242: 423-426, 1988.
Boerner et al. "Production of Antigen-Specific Human Monoclonal Antibodies From In-Vitro-Primed Human Splenocytes", The Journal of Immunology, 147(1): 86-95, 1991.
Boon et al. "Human Tumor Antigens Recognized by T Lymphocytes", The Journal of Experimental Medicine, 183: 725-729, 1996.
Carmon et al. "Novel Breast-Tumor-Associated MUC1-Derived Peptides: Characterization in Db-/-X β2 Microglobulin (βm) Null Mice Transgenic for a Chimeric HLA-A2.1/Db β2 Microglobulin Single Chain", International Journal of Cancer, 85(3): 391-397, 2000.
Chames et al. "Direct Selection of a Human Antibody Fragment Directed Against the Tumor T-Cell Epitope HLA-A1-MAGE-A1 From a Nonimmunized Phage-Fab Library", Proc. Natl. Acad. Sci. USA, XP002967292, 97(14): 7969-7974, Jul. 5, 2000. Abstract.
Chames et al. "TCR-Like Human Antibodies Expressed on Human CTLs Mediate Antibody Affinity-Dependent Cytolytic Activity", The Journal of Immunology, XP002383419, 169(2): 1110-1118, Jul. 15, 2002.
Chowdhury et al. "Improving Antibody Affinity by Mimicking Somatic Hypermutation In Vitro", Nature Biotechnology, 17(6): 568-572, 1999. Abstract.
Christinck et al. "Peptide Binding to Class I MHC on Living Cells and Quantitation of Complexes Required for CTL Lysis", Nature, 352: 67-70, 1991.
Chung et al. "Competitive Inhibition In Vivo and Skewing of the T Cell Repertoire of Antigen-Specific CTL Priming by an Anti-Peptide-MHC Monoclonal Antbody", The Journal of Immunology, 167: 699-707, 2001.
Cohen et al. "Direct Detection and Quantitation of a Distinct T-Cell Epitope Derived From Tumor-Specific Epithelial Cell-Associated Mucin Using Human Recombinant Antibodies Endowed With the Antigen-Specific, Major Histocompatibility Complex-Restricted Specificity of T Cells", Cancer Research, 62(20): 5835-5844, 2002. Abstract.
Cohen et al. "Direct Phenotypic Analysis of Human MHC Class I Antigen Presentation: Visualization, Quantitation, and In Situ Detection of Human Viral Epitopes Using Peptide-Specific, MHC-Restricted Human Recombinant Antibodies", Journal of Immunology, XP002461576, 170(8): 4349-4361, Apr. 15, 2003.
Cohen et al. "Generation of Recombinant Immunotoxins for Specific Targeting of Tumor-Related Peptides Presented by MHC Molecules", Methods in Molecular Biology, 207: 269-282, 2003. Abstract.
Cohen et al. "Recombinant Antibodies With MHC-Restricted, Peptide-Specific, T-Cell Receptor-Like Specificity: New Tools to Study Antigen Presentation and TCR-Peptide-MHC Interactions", Journal of Molecular Recognition, 16(5): 324-332, 2003. Abstract.
Cote et al. "Generation of Human Monoclonal Antibodies Reactive With Cellular Antigens", PNAS, 80: 2026-2030, 1983.
Coulie et al. "A New Gene Coding for a Differentiation Antigen Recognized by Autologous Cytolytic T Lymphocytes on HLA-A2 Melanomas", Journal of Experimental Medicine, 180: 35-42, 1994.

(56) References Cited

OTHER PUBLICATIONS

Counter et al. "Telomerase Activity in Normal Leukocytes and in Hematologic Malignancies", Blood, 85(9): 2315-2320, 1995.
Dadaglio et al. "Characterization and Quantitation of Peptide-MHC Complexes Produced From Hen Egg Lysozyme Using a Monoclonal Antibody", Immunity, 6(6): 727-738, 1997. Abstract.
Daugherty et al. "Polymerase Chain Reaction Facilities the Cloning, CDR-Grafting, and Rapid Expression of a Murine Monoclonal Antibody Directed Against the CD18 Component of Leukocyte Integrins", Nucleic Acids Research, 19(9): 2471-2476, 1991.
Day et al. "Direct Delivery of Exogenous MHC Class I Molecule-Binding Oligopeptides to the Endoplasmic Reticulum of Viable Cells", Proc. Natl. Acad. Sci. USA, 94: 8064-8069, 1997.
De Haard et al. "A Large Non-Immunized Human Fab Fragment Phage Library That Permits Rapid Isolation and Kinetic Analysis of High Affinity Antibodies", The Journal of Biological Chemistry, 274(26): 218-18230, 1999.
Demotz et al. "The Minimal Number of Class II MHC-Antigen Complexes Needed for T Cell Activation", Science, 249: 1028-1030, 1990.
Denkberg et al. "Critical Role for CD8 in Binding of MHC Tetramers to TCR: CD8 Antibodies Block Specific Binding of Human Tumor-Specific MHC-Peptide Tetramers to TCR", The Journal of Immunology, 167: 270-276, 2001.
Denkberg et al. "Direct Visualization of Distinct T Cell Epitopes Derived From a Melanoma Tumor-Associated Antigen by Using Human Recombinant Antibodies With MHC-Restricted T Cell Receptor-Like Specificity", Proc. Natl. Acad. Sci. USA, 99(14): 9421-9426, 2002.
Denkberg et al. "Recombinant Antibodies With T-Cell Receptor-Like Specificity: Novel Tools to Study MHC Class I Presentation", Autoimmunity Reviews, XP024977451, 5(4): 252-257, Apr. 1, 2006. Abstract, Table 1.
Denkberg et al. "Recombinant Human Single-Chain MHC-Peptide Complexes Made From *E. coli* by In Vitro Refolding: Functional Single-Chain MHC-Peptide Complexes and Tetramers With Tumor Associated Antigens", European Journal of Immunology, XP002289070, 30(12): 3522-3532, Dec. 1, 2000. Abstract.
Derby et al. "High Avidity CTL Exploit Two Complementary Mechanisms to Provide Better Protection Against Viral Infection Than Low-Avidity CTL", The Journal of Immunology, 166: 1690-1697, 2001.
Dudley et al. "T-Cell Clones From Melanoma Patients Immunized Against an Anchor-Modified GP100 Peptide Display Discordant Effector Phenotypes", Cancer Journal, 6(2): 69-77, 2000. Abstract.
Dutoit et al. "Heterogenous T-Cell Response to MAGE-A10[254-262]: High Avidity-Specific Cytolytic T Lymphocytes Show Superior Antitumor Activity", Cancer Research, 61: 5850-5856, 2001.
Engberg et al. "Recombinant Antibodies With the Antigen-Specific, MHC Restricted Specifity of T Cells: Novel Reagents for Basic and Clinical Investigations and Immunotherapy", Immunotechnology, XP000989992, 4(3-4): 273-278, Mar. 1999.
Gennaro "Remington's Pharmaceutical Sciences 18th Edition", Mack Printing Co., p. 1579, 1990.
Grassmann et al. "Transformation to Continuous Growth of Primary Human T Lymphocytes by Human T-Cell Leukemia Virus Type I X-Region Genes Tranduced by a Herpesvirus Saimiri Vector", PNAS, 86: 3351-3355, 1989.
Haard et al. "A Large Non-Immunized Human Fab Fragment Phage Library That Permits Rapid Isolation and Kinetic Analysis of High Affinity Antibodies", The Journal of Biological Chemistry, 274(26): 18218-18230, 1999.
Harding et al. "Quantitation of Antigen-Presenting Cell MHC Class II/ Peptide Complexes Necessary for T-Cell Stimulation", Nature, 346: 574-576, 1990.
Harlow et al. "Antibodies, A Laboratory Manual", Cold Spring Harbor Laboratory, USA, p. 287, 1988.
Hoogenboom et al. "By-Passing Immunisation—Human Antibodies From Synthetic Repertoires of Germline VH Gene Segments Rearranged In Vitro", Journal of Molecular Biology, 227: 381-388, 1992.
ISR Apr. 15, 2005.
ISR Jul. 23, 2003.
ISR (not by us) Feb. 24, 2004.
Jones et al. "Replacing the Complementarity-Determining Regions on a Human Antibody With Those From a Mouse", Nature, 321: 522-525,1986.
Kawakami et al. "Identification of a Human Melanoma Antigen Recognized by Tumor-Infiltrating Lymphocytes Associated With In Vivo Tumor Rejection", Proc. Natl. Acad, Sci. USA, 91: 6458-6462, 1994.
Kfir et al. "Antibody-Mediated Targeting of Human Single-Chain Class I MHC With Covalently Linked Peptides Induces Efficient Killing of Tumor Cells by Tumor or Viral-Specific Cytotoxic T Lymphocytes", Cancer Immunology & Immunotherapy, XP019333169, 54(9): 867-879, Sep. 1, 2005. Abstract.
Kim et al. "Specific Association of Human Telomerase Activity With Immortal Cells and Cancer", Science, 266(5193): 2011-2015, 1994. Abstract.
Kirkin et al. "Generation of Human-Melanoma-Specific T Lymphocyte Clones Defining Novel Cytolytic Targets With Panels of Newly Established Melanoma Cell Lines", Cancer Immunology and Immunotherapy, 41(2): 71-81, 1995. Abstract.
Köhler et al. "Continuous Cultures of Fused Cells Secreting Antibody of Predefined Specificity", Nature, 256:495-497, 1975.
Kondo et al. "Activity of Immunotoxins Constructed With Modified Pseudomonas Exotoxin a Lacking the Cell Recognition Domain", The Journal of Biological Chemistry, 263(19): 9470-9475, 1988.
Krogsgaard et al. "Visualization of Myelin Basic Protein (MBP) T Cell Epitopes in Multiple Sclerosis Lesions Using a Monoclonal Antibody Specific for the Human Histocompatibility Leukocyte Antigen (HLA)-DR2-MBP 85-99 Complex", The Journal of Experimental Medicine, 191(8): 1395-1412, 2000.
Kugler et al. "Regression of Human Metastatic Renal Cell Carcinoma After Vaccination With Tumor Cell-Dendritic Cell Hybrids", Nature Medicine, 6(3): 332-336, 2000. Abstract.
Lee et al. "Characterization of Circulating T Cells Specific for Tumor-Associated Antigens in Melanoma Patients", Nature Medicine, 5(6): 677-685, 1999. Abstract.
Lev et al. "Isolation and Characterization of Human Recombinant Antibosies Endowed With the Antigen-Specific, Major Histocompatibility Complex-Restricted Specificity of T Cells Directed Toward the Widely Expressed Tumor T-Cell Epitopes of the Telomerase Catalytic Subunit", Cancer Research, XP007914415, 62(11): 3184-3194, Jun. 1, 2002.
Lode et al. "Targeted Cytokines for Cancer Immunotherapy", Immunology Research, 21(2-3): 279-288, 2000. Abstract.
Lonberg et al. "Antigen-Specific Human Antibodies From Mice Comprising Four Distinct Genetic Modifications", Nature, 368: 856-859, 1994.
Marks et al. "By-Passing Immunization—Human Antibodies From V-Gene Libraries Displayed on Phage", Journal of Molecular Biology, 222: 581-597, 1991.
McEachern et al. "Telomeres and Their Control", Annual Review of Genetics, 34: 331-358, 2000. Abstract.
Minev et al. "Cytotoxic T Cell Immunity Against Telomerase Reverse Transcriptase in Humans", Proc. Natl. Acad. Sci. USA, 97(9): 4796-4801, 2000.
Morrison "Success in Specification", Nature, 368: 812-813, 1994.
Murphy et al. "A Novel MHC Class II Epitope Expressed in Thymic Medulla But Not Cortex", Nature, 338: 765-768, 1989.
Nakamura et al. "Reversing Time: Origin of Telomerase", Cell, 92: 587-590, 1998.
Neuberger "Generating High-Avidity Human Mabs in Mice", Nature Biotechnology, 14: 396, 1996.
Ngo et al. "Computational Complexity, Protein Structure Prediction, and the Levinthal Paradox", The Protein Folding Problem and Tertiary Structure Prediction, p. 491-495, 1994.
Noy et al. "T-Cell Receptor-Like Antibodies: Novel Reagents for Clinical Cancer Immunology and Immunotherapy", Future Drugs, XP009067037, 5(3): 523-536, Jun. 1, 2005. Abstract, Table 1.
OA Sep. 10, 2004.

(56) References Cited

OTHER PUBLICATIONS

Offringa et al. "Design and Evaluation of Antigen-Specific Vaccination Strategies Against Cancer", Current Opinion in Immunology, 12(5): 576-582, 2000. Abstract.
Ogg et al. "Quantitation of HIV-1-Specific Cytotoxic T Lymphocytes and Plasma Load of Viral RNA", Science, 279(5359): 2103-2106, 1998. Abstract.
Parkhurst et al. "Improved Induction of Melanoma-Reactive CTL With Peptides From the Melanoma Antigen Gp100 Modified at HLA-A*0201-Binding Residues", The Journal of Immunology, 157: 2539-2548, 1996. Tables II, III.
Pascolo et al. "HLA-A2.1-Restricted Education and Cytolytic Activity of CD8+ T Lymphocytes From β2 Microglobulin (βm) HLA-A2.1 Monochain Transgenic H-2Db βm Double Knockout Mice", Journal of Experimental Medicine, 185(12): 2043-2051, 1977.
Patamawenu "Generation of Functional HLA-A2 Molecules Covealently Attached to Antigenic Peptides", B.S. ( University of Maryland) Thesis, p. 8-9, 1988. Abstract.
Poiesz et al. "Detection and Isolation of Type C Retrovirus Particles From Fresh and Cultured Lymphocytes of a Patient With Cutaneous T-Cell Lymphoma", PNAS, 77(12): 7415-7419, 1980.
Poljak et al. "Structure and Specificity of Antibody Molecules", Philosophical Transactions of the Royal Society of London, Series B, 272: 43-51, 1975.
Porgador et al. "Localization, Qunatitation, and In Situ Detection of Specific Peptide-HC Class I Complexes Using a Monoclonal Antibody", Immunity, 6(6): 715-726, 1997. Abstract.
Porter "The Hydrolysis of Rabbit γ-Globulin and Antibodies With Crystalline Papain", Biochemical Journal, 73: 119-126, 1959.
Pozzatti et al. "The Human T-Lymphotropic Virus Type I "Tax" Gene Can Cooperate With the "Ras" Oncogene to Induce Neoplastic Transformation of Cells", Molecular and Cellular Biology, 10(1): 413-417, 1990.
Rammensee et al. "MHC Ligands and Peptide Motifs", Molecular Biology Intelligence Unit, Landes Bioscience, p. 235-281, 1997.
Reay et al. "Determination of the Relationship Between T Cell Responsiveness and the Number of MHC-Peptide Complexes Using Specific Monoclonal Antibodies", The Journal of Immunology, 164(11): 5626-5634, 2000.
Reiter et al. "An Antibody Single-Domain Phage Display Library of a Native Heavy Chain Variable Region: Isolation of Functional Single-Domain VH Molecules With a Unique Interface", Journal of Molecular Biology, 290(3): 685-698, 1999. Abstract.
Reiter et al. "Antibody Engineering for Targeted Therapy of Cancer: Recombinant Fv-Immunotoxins", Current Pharmaceutical Biotechnology, 2: 19-46, 2001.
Reiter et al. "Peptide-Specific Killing of Antigen-Presenting Cells by a Recombinant Antibody-Toxin Fusion Protein Targeted to Major Histocompatibility Complex/Peptide Class I Complexes With T Cell Receptor-Like Specificity", Proc. Natl. Acad. Sci. USA, 94(9): 4631-4636, 1997. Abstract.
Reiter et al. "Recombinant Immunotoxins in Targeted Cancer Cell Therapy", Advances in Cancer Research, 81: 93-124, 2001. Abstract.
Renkvist et al. "A Listing of Human Tumor Antigens Recognized by T Cells", Cancer Immunology and Immunotherapy, 50(1): 3-15, 2001. Abstract.
Restifo et al. "Identification of Human Cancers Deficient in Antigen Processing", The Journal of Experimental Medicine, 177: 265-272, 1993.
Riechmann et al. "Reshaping Human Antibodies for Therapy", Nature, 332: 323-327, 1988.
Rivoltini et al. "Recognition of Melanoma-Derived Antigens by CTL: Possible Mechanisms Involved in Down-Regulating Anti-Tumor T-Cell Reactivity", Critical Review in Immunology, 18(1-2): 55-63, 1998. Abstract.
Robert et al. "Antibody-Conjugated MHC Class I Tetramers Can Target Tumor Cells for Specific lysis by T Lumphocytes", European Journal of Immunology, 30: 3165-3170, 2000.
Rosenberg "Insight", Nature, 411: 380-384, 2001.
Rosenberg "Progress in Human Tumour Immunology and Immunotherapy", Nature, 411: 380-384, 2001. Abstract.
Rudikoff et al. "Single Amino Acid Substitution Altering Antigen-Binding Specifity", Proc. Natl. Acad. Sci. USA, 79(6): 1979-1983, Mar. 1982.
Saito et al. "In Vivo Selection of T-Cell Receptor Junctional Region Sequences by HLA-A2 Human T-Cell Lymphotropic Virus Type 1 Tax11-19 Peptide Complexes", Journal of Virology, 75(2): 1065-1071, Jan. 2001.
Seliger et al. "Antigen-Processing Machinery Breakdown and Tumor Growth", Immunology Today, 21(9): 455-464, 2000. Abstract.
Shay et al. "Telomerase and Cancer", Human Molecular Genetics, 10(7): 677-685, 2001.
Shiono et al. "Spontaneous Production of Anti-IFN-Alpha and Anti-IL-12 Autoantibodies by Thymoma Cells From Myasthenia Gravis Patients Suggests Autoimmunization in the Tumor", International Immunology, 15(8): 903-913, 2003. GenPept AAO4555.
Shriner et al. "Comparison of the Human Immune Response to Conjugate and Polysaccharide Pneumococcal Vaccination Using. A Reconstituted SCID Mouse Model", Vaccine, 24(49-50): 7197-7203, 2006. GenPept ABG38407.
Stanislawski et al. "Circumventing Tolerance to a Human MDM2-Derived Tumor Antigen by Tcr Gene Transfer", Nature Immunology, 2(10): 962-970, 2001. Abstract.
Stedman Definition "Fab Fragment", Stedman's Online Medical Dictionary, 27th Edition. Www.stedmans.com.
Stryhn et al. "Shared Fine Specificity Between T-Cell Receptors and an Antibody Recognizing a Peptide/Major Histocompatibility Class I Complex", Proc. Natl. Acad. Sci. USA, 93: 10338-10342, 1996.
Stubbs et al. "Influence of Core Fucosylation on the Flexibility of a Biantennary N-Linked Oligosaccharide", Biochemistry, 35: 937-947, 1996.
Verhoeyen et al. "Reshaping Human Antiodies: Grafting an Antilysozyme Activity", Science, 239: 1534-1536, 1988.
Vonderheide et al. "The Telomerase Catalytic Subunit is a Widely Expressed Tumor-Associated Antigen Recognized by Cytotoxic T Lymphocytes", Immunity, 10(6): 673-679, 1999. Abstract.
Waterhouse et al. "Combinatorial Infection and In Vivo Recombination: A strategy for Making Large Phage Antibody Repertoires", Nucleic Acids Research, 21(9): 2265-2266, 1993.
Winter et al. "Man-Made Antibodies", Nature, 349: 293-299, 1991.
Withoff et al. "Bi-Specific Antibody Therapy for the Treatment of Cancer", Current Opinion in Molecular Therapy, 3(1): 53-62, 2001. Abstract.
Wülling et al. "Correctly Folded T-Cell Receptor Fragments in the Periplasm of *Escherichia coli*", Journal of Molecular Biology, 242(5): 655-669, 1994. Abstract.
Yoshida et al. "Isolation and Characterization of Retrovirus From Cell Lines of Human Adult T-Cell Leukemia and Its Implication in the Disease", PNAS, 79: 2031-2035, 1982.
Zhong et al. "Antigen-Unspecific B Cells and Lymphoid Dendritic Cells Both Show Extensive Surface Expression of Processed Antigen-Major Histocompatibility Complex Class II Complexes After Soluble Protein Exposure In Vivo or In Vitro", The Journal of Experimental Medicine, 186(5): 673-682, 1997.
Zhong et al. "Production, Specificity, and Funtionality of Monoclonal Antibodies to Specific Peptide-Major Histocompatibility Complex Class II Complexes Formed by Processing of Exogenous Protein", Proc. Natl. Acad. Sci. USA, 94: 13856-13861, 1997.
Communication Pursuant to Article 94(3) EPC Dated Jul. 4, 2013 From the European Patent Office Re. Application No. 07777164.0.
Hearing Notice Dated Sep. 25, 2013 From the Government of India, Patent Office, Intellectual Property Building Re. Application No. 2669/MUMNP/2008.
Official Action Dated Sep. 3, 2013 From the US Patent and Trademark Office Re. U.S. Appl. No. 13/163,701.
Official Action Dated Jul. 15, 2013 From the US Patent and Trademark Office Re. U.S. Appl. No. 12/591,336.
Office Action Dated Jun. 26, 2013 From the Israel Patent Office Re. Application No. 160412 and Its Translation Into English.
Applicant-Initialed Interview Summary Dated Nov. 21, 2013 From the US Patent and Trademark Office Re. U.S. Appl. No. 13/163,701.

(56) References Cited

OTHER PUBLICATIONS

Notice of Non-Responsive Amendment Dated Oct. 24, 2013 From the US Patent and Trademark Office Re. U.S. Appl. No. 12/486,794.
Notice to Submit Response Dated Sep. 25, 2013 From the Korean Intellectual Property Office Re. Application No. 10-2008-7030875 and Its Translation Into English.
Requisition by the Examiner Dated Oct. 1, 2013 From the Canadian Intellectual Property Office Re. Application No. 2,404,489.
Requisition by the Examiner Dated Dec. 3, 2013 From the Canadian Intellectual Property Office Re. Application No. 2,652,538.
Requisition by the Examiner Dated Oct. 28, 2013 From the Canadian Intellectual Property Office Re. Application No. 2,476,625.
Chowdhury et al. "ScFv Antibody SS [*Mus musculus*]", NCBI Database [Online], GenBank Assession No. AAC04760.1, Database Accession No. AAC04760, Sep. 30, 1999.
Applicant-Initiated Interview Summary Dated Dec. 13, 2013 From the Patent and Trademark Office Re. U.S. Appl. No. 12/591,421.
Applicant-Initiated interview Summary Dated Dec. 13, 2013 From the US Patent and Trademark Office Re. U.S. Appl. No. 12/591,336.
Requisition by the Examiner Dated Dec. 10, 2013 From the Canadian Intellectual Property Office Re. Application No. 2,474,782.

\* cited by examiner

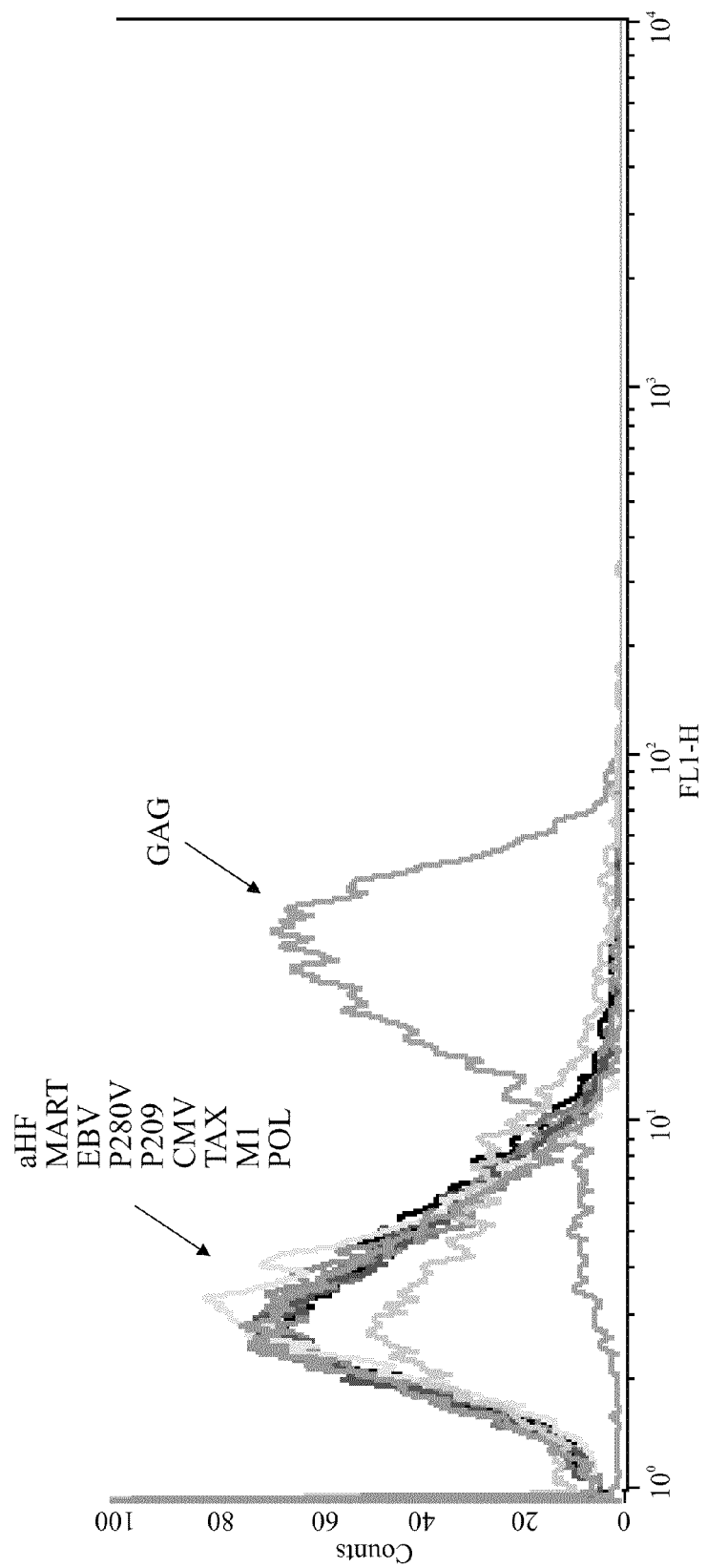

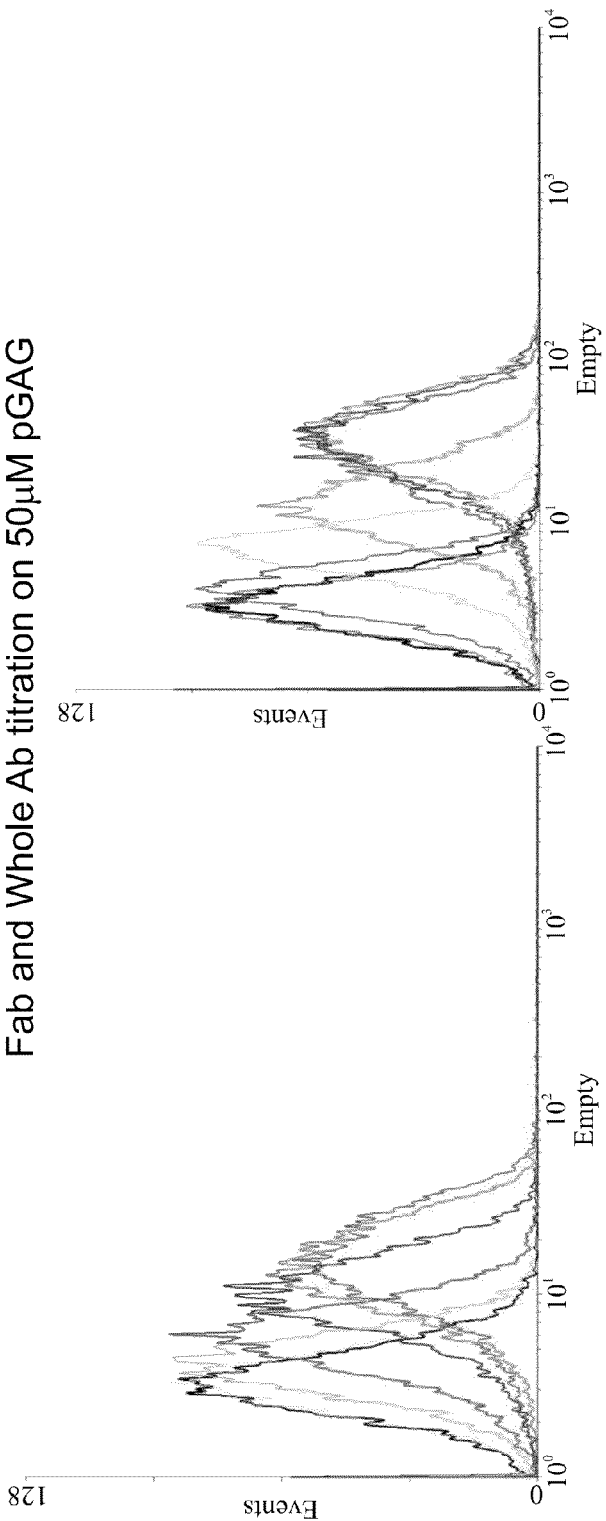

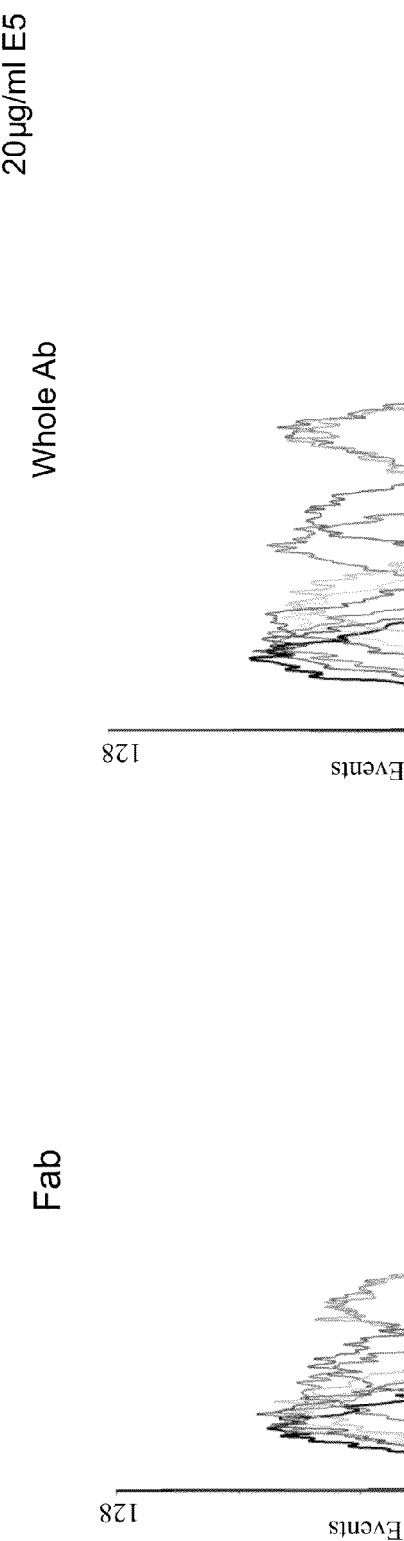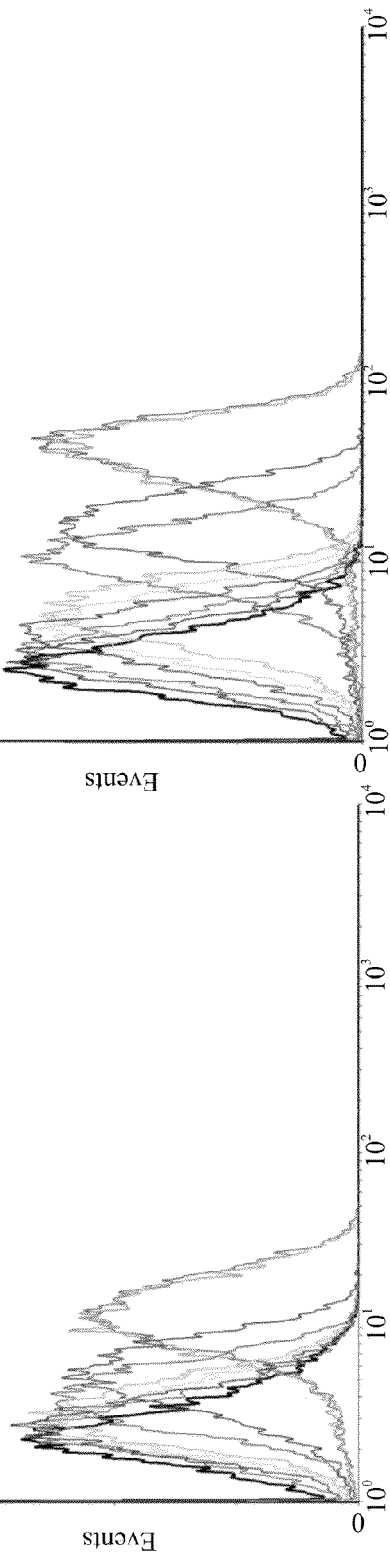

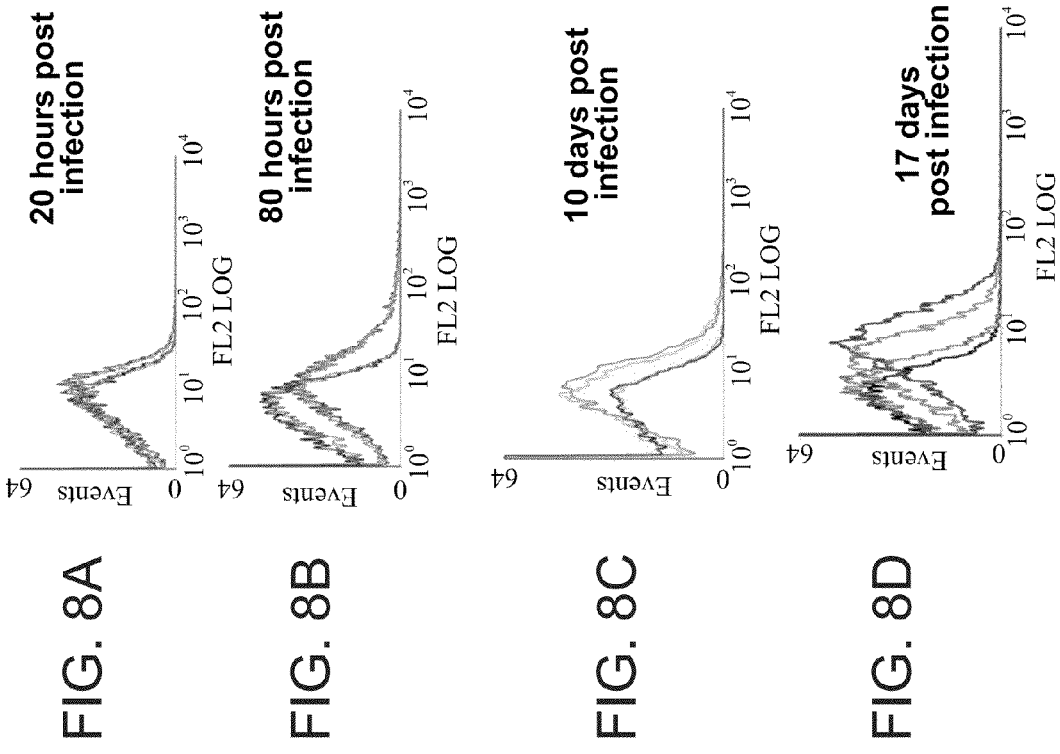

FIG. 9A

E5-HIV antibody Light Chain (Lambda); Amino acid sequence

QSVLTQPPSVSVAPGKTARIPC EGNYIGSSNVHWYQQKPGQAPVLVIH FDSD
RPSGIPDRFSGSNSGNMATLTISRVEAGDEADYYC QVWENHGWVFGGGTKL
TVLSQPKAAPSVTLFPPSSEELQANKATLVCLISDFYPGAVTVAWKADSSPVK
AGVETTTPSKQSNNKYAASSYLSLTPEQWKSHKSYSCQVTHEGSTVEKTVAP
TECS (SEQ ID NO:15)

FIG. 9B

E5-HIV antibody Light Chain (Lambda); Nucleic acid sequence

CAGTCTGTGCTGACTCAGCCACCCTCAGTGTCAGTGGCCCCAGGAAAGAC
GGCCAGGATTCCCTGT GAGGGAAACTACATTGGAAGTAGCAATGTGCA
CTGGTACCAGCAGAAGCCAGGCCA GGCCCCTGTGTTGGTCATCCAT TTTG
ATAGCGACCGGCCCTCA GGGATCCCTGACCGATTTTCTGGCTCCAACTCT
GGCAATATGGCCACCCTGACCATCAGCAGGGTCGAAGCCGGGGATGAGG
CCGACTATTACTGT CAGGTGTGGGAGAATCATGGTTGGGTGTTCGGCG
GAGGGACCAAGCTGACCGTCCTGAGTCAGCCCAAGGCTGCCCCCTCGGTC
ACTCTGTTCCCACCCTCCTCTGAGGAGCTTCAAGCCAACAAGGCCACACT
GGTGTGTCTCATAAGTGACTTCTACCCGGGAGCCGTGACAGTGGCCTGGA
AGGCAGATAGCAGCCCCGTCAAGGCG GGAGTGGAGACCACCACACCCTC
CAAACAAAGCAACAACAAGTACGCGGCCAGCAGCTACCTGAGCCTGACG
CCTGAGCAGTGGAAGTCCCACAAAAGCTACAGCTGCCAGGTCACGCATGA
AGGGAGCACCGTGGAGAAGACAGTGGCCCCTACAGAATGTTCA (SEQ ID NO:16)

FIG. 9C

HIV E5 antibody Heavy Chain; Amino acid sequence

EVQLVETGGGLVQPGESLRLSCAASGFTFS DYEMNWVRQAPGKGLEWVSYI
SSSGSTIYYADSVKG RFTIYRDNAKNSLYLQMNSLRAEDTALYYCAR AWGV
GPPDYWGQGTLVTVSSASTKGPSVFPLAPSSKSTSGGTAALGCLVKDYFPEP
VTVSWNSGALTSGVHTFPAVLQSSGLY SLSSVVTVPSSSLGTQTYICNVNHKP
SNTKVDKKVEPKSCAAAHHHHHHHHGAAEQKLISEEDLNGAA (SEQ ID NO:17)

FIG. 9D

HIV E5 antibody Heavy Chain; Nucleic acid sequence

GAGGTGCAGCTCGTGGAGACTGGGGGAGGCTTGGTACAGCCTGGAGAGT
CCCTGAGACTCTCCTGTGCAGCCTCTGGATTCACCTTCAGTGATTATGAA
ATGAACTGGGTCCGCCAGGCTCCAGGGAAGGGGCTGGAGTGGGTTTCAT
ACATTAGTAGTAGTGGTAGTACCATATACTACGCAGACTCTGTGAAG
GGCCGATTCACCATCTACAGAGACAACGCCAAGAACTCACTGTATCTGCA
AATGAATAGCCTGAGAGCCGAGGACA CGGCTCTTTATTACTGTGCGAGA G
CTTGGGGCGTGGGACCCCCTGACTACTGGGGCCAGGGAACCCTGGTCA
CCGTCTCAAGCGCCTCCACCAAGGGCCCATCGGTCTTCCCCCTGGCACCCT
CCTCCAAGAGCACCTCTGGGGGCACAGCGGCCCTGGGCTGCCTGGTCAAG
GACTACTTCCCCGAACCGGTGACGGTGTCGTGGAACTCAGGCGCCCTGAC
CAGCGGCGTCCACACCTTCCCGGCTGTCCTACAGTCCTCAGGACTCTACTC
CCTCAGCAGCGTAGTGACCGTGCCCTCCAGCAGCTTGGGCACCCAGACCT
ACATCTGCAACGTGAATCACAAGCCCAGCAACACCAAGGTGGACAAGAA
AGTTGAGCCCAAATCTTGTGCGGCCGCACATCATCATCACCATCACGGGG
CCGCAGAACAAAAACTCATCTCAGAAGAGGATCTGAATGGGGCCGCA
(SEQ ID NO:18)

SEQUENCE LISTING

<160> NUMBER OF SEQ ID NOS: 85

<210> SEQ ID NO 1
<211> LENGTH: 500
<212> TYPE: PRT
<213> ORGANISM: Human immunodeficiency virus type 1

<400> SEQUENCE: 1

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60
```

```
Gln Pro Ser Leu Gln Thr Gly Ser Glu Glu Leu Arg Ser Leu Tyr Asn
 65                  70                  75                  80

Thr Val Ala Thr Leu Tyr Cys Val His Gln Arg Ile Glu Ile Lys Asp
                 85                  90                  95

Thr Lys Glu Ala Leu Asp Lys Ile Glu Glu Gln Asn Lys Ser Lys
                100                 105                 110

Lys Lys Ala Gln Gln Ala Ala Ala Asp Thr Gly His Ser Asn Gln Val
            115                 120                 125

Ser Gln Asn Tyr Pro Ile Val Gln Asn Ile Gln Gly Gln Met Val His
        130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
                180                 185                 190

Gly His Gln Ala Ala Met Gln Met Leu Lys Glu Thr Ile Asn Glu Glu
            195                 200                 205

Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
                260                 265                 270

Ile Val Arg Met Tyr Ser Pro Thr Ser Ile Leu Asp Ile Arg Gln Gly
            275                 280                 285

Pro Lys Glu Pro Phe Arg Asp Tyr Val Asp Arg Phe Tyr Lys Thr Leu
        290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
                340                 345                 350

Val Gly Gly Pro Gly His Lys Ala Arg Val Leu Ala Glu Ala Met Ser
            355                 360                 365

Gln Val Thr Asn Ser Ala Thr Ile Met Met Gln Arg Gly Asn Phe Arg
        370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
                420                 425                 430

Phe Leu Gly Lys Ile Trp Pro Ser Tyr Lys Gly Arg Pro Gly Asn Phe
            435                 440                 445

Leu Gln Ser Arg Pro Glu Pro Thr Ala Pro Pro Glu Glu Ser Phe Arg
        450                 455                 460

Ser Gly Val Glu Thr Thr Thr Pro Pro Gln Lys Gln Glu Pro Ile Asp
465                 470                 475                 480

Lys Glu Leu Tyr Pro Leu Thr Ser Leu Arg Ser Leu Phe Gly Asn Asp
                485                 490                 495
```

```
Pro Ser Ser Gln
            500

<210> SEQ ID NO 2
<211> LENGTH: 9
<212> TYPE: PRT
<213> ORGANISM: Artificial sequence
<220> FEATURE:
<223> OTHER INFORMATION: GAG(77-85) peptide

<400> SEQUENCE: 2

Ser Leu Tyr Asn Thr Val Ala Thr Leu
1               5

<210> SEQ ID NO 3
<211> LENGTH: 11
<212> TYPE: PRT
<213> ORGANISM: Artificial sequence
<220> FEATURE:
<223> OTHER INFORMATION: CDR1 amino acid sequence of light chain E5
      antibody

<400> SEQUENCE: 3

Glu Gly Asn Tyr Ile Gly Ser Ser Asn Val His
1               5                   10

<210> SEQ ID NO 4
<211> LENGTH: 7
<212> TYPE: PRT
<213> ORGANISM: Artificial sequence
<220> FEATURE:
<223> OTHER INFORMATION: CDR2 amino acid sequence of light chain E5
      antibody

<400> SEQUENCE: 4

Phe Asp Ser Asp Arg Pro Ser
1               5

<210> SEQ ID NO 5
<211> LENGTH: 9
<212> TYPE: PRT
<213> ORGANISM: Artificial sequence
<220> FEATURE:
<223> OTHER INFORMATION: CDR3 amino acid sequence of light chain E5
      antibody

<400> SEQUENCE: 5

Gln Val Trp Glu Asn His Gly Trp Val
1               5

<210> SEQ ID NO 6
<211> LENGTH: 5
<212> TYPE: PRT
<213> ORGANISM: Artificial sequence
<220> FEATURE:
<223> OTHER INFORMATION: CDR1 amino acid sequence of heavy chain E5
      antibody

<400> SEQUENCE: 6

Asp Tyr Glu Met Asn
1               5

<210> SEQ ID NO 7
<211> LENGTH: 17
<212> TYPE: PRT
<213> ORGANISM: Artificial sequence
<220> FEATURE:
<223> OTHER INFORMATION: CDR2 amino acid sequence of heavy chain E5
```

-continued antibody

<400> SEQUENCE: 7

Tyr Ile Ser Ser Ser Gly Ser Thr Ile Tyr Tyr Ala Asp Ser Val Lys
1               5                   10                  15

Gly

<210> SEQ ID NO 8
<211> LENGTH: 9
<212> TYPE: PRT
<213> ORGANISM: Artificial sequence
<220> FEATURE:
<223> OTHER INFORMATION: CDR3 amino acid sequence of heavy chain E5
      antibody

<400> SEQUENCE: 8

Ala Trp Gly Val Gly Pro Pro Asp Tyr
1               5

<210> SEQ ID NO 9
<211> LENGTH: 33
<212> TYPE: DNA
<213> ORGANISM: Artificial sequence
<220> FEATURE:
<223> OTHER INFORMATION: CDR1 nucleic acid sequence of light chain E5
      antibody

<400> SEQUENCE: 9
gagggaaact acattggaag tagcaatgtg cac                           33

<210> SEQ ID NO 10
<211> LENGTH: 21
<212> TYPE: DNA
<213> ORGANISM: Artificial sequence
<220> FEATURE:
<223> OTHER INFORMATION: CDR2 nucleic acid sequence of light chain E5
      antibody

<400> SEQUENCE: 10
tttgatagcg accggccctc a                                        21

<210> SEQ ID NO 11
<211> LENGTH: 27
<212> TYPE: DNA
<213> ORGANISM: Artificial sequence
<220> FEATURE:
<223> OTHER INFORMATION: CDR3 nucleic acid sequence of light chain E5
      antibody

<400> SEQUENCE: 11
caggtgtggg agaatcatgg ttgggtg                                  27

<210> SEQ ID NO 12
<211> LENGTH: 15
<212> TYPE: DNA
<213> ORGANISM: Artificial sequence
<220> FEATURE:
<223> OTHER INFORMATION: CDR1 nucleic acid sequence of heavy chain E5
      antibody

<400> SEQUENCE: 12
gattatgaaa tgaac                                               15

<210> SEQ ID NO 13
<211> LENGTH: 51
<212> TYPE: DNA
<213> ORGANISM: Artificial sequence -continued
<220> FEATURE:
<223> OTHER INFORMATION: CDR2 nucleic acid sequence of heavy chain E5
      antibody

<400> SEQUENCE: 13
tacattagta gtagtggtag taccatatac tacgcagact ctgtgaaggg c        51

<210> SEQ ID NO 14
<211> LENGTH: 27
<212> TYPE: DNA
<213> ORGANISM: Artificial sequence
<220> FEATURE:
<223> OTHER INFORMATION: CDR3 nucleic acid sequence of heavy chain E5
      antibody

<400> SEQUENCE: 14
gcttggggcg tgggaccccc tgactac        27

<210> SEQ ID NO 15
<211> LENGTH: 212
<212> TYPE: PRT
<213> ORGANISM: Artificial sequence
<220> FEATURE:
<223> OTHER INFORMATION: Amino acid sequence of the Light Chain E5
      antibody

<400> SEQUENCE: 15

Gln Ser Val Leu Thr Gln Pro Pro Ser Val Ser Val Ala Pro Gly Lys
1               5                   10                  15

Thr Ala Arg Ile Pro Cys Glu Gly Asn Tyr Ile Gly Ser Ser Asn Val
            20                  25                  30

His Trp Tyr Gln Gln Lys Pro Gly Gln Ala Pro Val Leu Val Ile His
        35                  40                  45

Phe Asp Ser Asp Arg Pro Ser Gly Ile Pro Asp Arg Phe Ser Gly Ser
    50                  55                  60

Asn Ser Gly Asn Met Ala Thr Leu Thr Ile Ser Arg Val Glu Ala Gly
65                  70                  75                  80

Asp Glu Ala Asp Tyr Tyr Cys Gln Val Trp Glu Asn His Gly Trp Val
                85                  90                  95

Phe Gly Gly Gly Thr Lys Leu Thr Val Leu Ser Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Lys Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 16
<211> LENGTH: 636
<212> TYPE: DNA
<213> ORGANISM: Artificial sequence
<220> FEATURE:

<223> OTHER INFORMATION: nucleic acid sequence of the Light Chain E5
      antibody

<400> SEQUENCE: 16

```
cagtctgtgc tgactcagcc accctcagtg tcagtggccc caggaaagac ggccaggatt      60
ccctgtgagg gaaactacat tggaagtagc aatgtgcact ggtaccagca gaagccaggc     120
caggccctg tgttggtcat ccattttgat agcgaccggc cctcagggat ccctgaccga      180
ttttctggct ccaactctgg caatatggcc accctgacca tcagcagggt cgaagccggg     240
gatgaggccg actattactg tcaggtgtgg gagaatcatg gttgggtgtt cggcggaggg     300
accaagctga ccgtcctgag tcagcccaag gctgccccct cggtcactct gttcccaccc     360
tcctctgagg agcttcaagc caacaaggcc acactggtgt gtctcataag tgacttctac     420
ccgggagccg tgacagtggc ctggaaggca gatagcagcc ccgtcaaggc gggagtggag     480
accaccacac cctccaaaca aagcaacaac aagtacgcgg ccagcagcta cctgagcctg     540
acgcctgagc agtggaagtc cacaaaagc tacagctgcc aggtcacgca tgaagggagc      600
accgtggaga agacagtggc ccctacagaa tgttca                               636
```

<210> SEQ ID NO 17
<211> LENGTH: 247
<212> TYPE: PRT
<213> ORGANISM: Artificial sequence
<220> FEATURE:
<223> OTHER INFORMATION: Amino acid sequence of the Heavy Chain E5
      antibody

<400> SEQUENCE: 17

```
Glu Val Gln Leu Val Glu Thr Gly Gly Gly Leu Val Gln Pro Gly Glu
1               5                   10                  15

Ser Leu Arg Leu Ser Cys Ala Ala Ser Gly Phe Thr Phe Ser Asp Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Tyr Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Ala Trp Gly Val Gly Pro Pro Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Ala Ala Ala
    210                 215                 220
```

His His His His His His Gly Ala Ala Glu Gln Lys Leu Ile Ser Glu
225                 230                 235                 240

Glu Asp Leu Asn Gly Ala Ala
            245

<210> SEQ ID NO 18
<211> LENGTH: 741
<212> TYPE: DNA
<213> ORGANISM: Artificial sequence
<220> FEATURE:
<223> OTHER INFORMATION: Nucleic acid sequence of the Heavy Chain E5
      antibody

<400> SEQUENCE: 18

```
gaggtgcagc tcgtggagac tgggggaggc ttggtacagc ctggagagtc cctgagactc      60
tcctgtgcag cctctggatt caccttcagt gattatgaaa tgaactgggt ccgccaggct     120
ccagggaagg ggctggagtg ggtttcatac attagtagta gtggtagtac catatactac     180
gcagactctg tgaagggccg attcaccatc tacagagaca cgccaagaa ctcactgtat      240
ctgcaaatga atagcctgag agccgaggac acggctcttt attactgtgc gagagcttgg     300
ggcgtgggac ccctgactac tggggccag ggaaccctgg tcaccgtctc aagcgcctcc      360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtccacacc ttcccggctg tcctacagtc ctcaggactc     540
tactccctca gcagcgtagt gaccgtgccc tccagcagct tgggcaccca gacctacatc     600
tgcaacgtga atcacaagcc cagcaacacc aaggtggaca agaaagttga gcccaaatct     660
tgtgcggccg cacatcatca tcaccatcac ggggccgcag aacaaaaact catctcagaa     720
gaggatctga atggggccgc a                                               741
```

<210> SEQ ID NO 19
<211> LENGTH: 238
<212> TYPE: PRT
<213> ORGANISM: Aequorea macrodactyla

<400> SEQUENCE: 19

Met Ser Lys Gly Glu Glu Leu Phe Thr Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
50                  55                  60

Gly Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Phe Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Met
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Met Pro Asp Lys Ala Asn Asn Gly
145                 150                 155                 160

-continued

```
Leu Lys Val Asn Phe Lys Ile Arg His Asn Ile Glu Gly Gly Val
                165                 170                 175

Gln Leu Ala Asp His Tyr Gln Thr Asn Val Pro Leu Gly Asp Gly Pro
                180                 185                 190

Val Leu Ile Pro Ile Asn His Tyr Leu Ser Leu Gln Thr Ala Ile Ser
                195                 200                 205

Lys Asp Arg Asn Glu Thr Arg Asp His Met Val Phe Leu Glu Phe Phe
210                 215                 220

Ser Ala Cys Gly His Thr His Gly Met Asp Glu Leu Tyr Lys
225                 230                 235

<210> SEQ ID NO 20
<211> LENGTH: 1435
<212> TYPE: PRT
<213> ORGANISM: Human immunodeficiency virus type 1

<400> SEQUENCE: 20

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
                20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
        50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
                100                 105                 110

Lys Lys Ala Gln Gln Ala Ala Ala Asp Thr Gly His Ser Asn Gln Val
            115                 120                 125

Ser Gln Asn Tyr Pro Ile Val Gln Asn Ile Gln Gly Gln Met Val His
        130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
                180                 185                 190

Gly His Gln Ala Ala Met Gln Met Leu Lys Glu Thr Ile Asn Glu Glu
            195                 200                 205

Ala Ala Glu Trp Asp Arg Val His Pro Val His Ala Gly Pro Ile Ala
        210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
                260                 265                 270

Ile Val Arg Met Tyr Ser Pro Thr Ser Ile Leu Asp Ile Arg Gln Gly
            275                 280                 285

Pro Lys Glu Pro Phe Arg Asp Tyr Val Asp Arg Phe Tyr Lys Thr Leu
        290                 295                 300
```

```
Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
            325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Arg Glu Asp Leu Ala Phe Leu Gln Gly Lys Ala Arg Glu Phe
        435                 440                 445

Ser Ser Glu Gln Thr Arg Ala Asn Ser Pro Thr Arg Arg Glu Leu Gln
    450                 455                 460

Val Trp Gly Arg Asp Asn Asn Ser Pro Ser Glu Ala Gly Ala Asp Arg
465                 470                 475                 480

Gln Gly Thr Val Ser Phe Asn Phe Pro Gln Val Thr Leu Trp Gln Arg
                485                 490                 495

Pro Leu Val Thr Ile Lys Ile Gly Gly Gln Leu Lys Glu Ala Leu Leu
            500                 505                 510

Asp Thr Gly Ala Asp Asp Thr Val Leu Glu Glu Met Ser Leu Pro Gly
        515                 520                 525

Arg Trp Lys Pro Lys Met Ile Gly Gly Ile Gly Gly Phe Ile Lys Val
    530                 535                 540

Arg Gln Tyr Asp Gln Ile Leu Ile Glu Ile Cys Gly His Lys Ala Ile
545                 550                 555                 560

Gly Thr Val Leu Val Gly Pro Thr Pro Val Asn Ile Ile Gly Arg Asn
                565                 570                 575

Leu Leu Thr Gln Ile Gly Cys Thr Leu Asn Phe Pro Ile Ser Pro Ile
            580                 585                 590

Glu Thr Val Pro Val Lys Leu Lys Pro Gly Met Asp Gly Pro Lys Val
        595                 600                 605

Lys Gln Trp Pro Leu Thr Glu Glu Lys Ile Lys Ala Leu Val Glu Ile
    610                 615                 620

Cys Thr Glu Met Glu Lys Glu Gly Lys Ile Ser Lys Ile Gly Pro Glu
625                 630                 635                 640

Asn Pro Tyr Asn Thr Pro Val Phe Ala Ile Lys Lys Lys Asp Ser Thr
                645                 650                 655

Lys Trp Arg Lys Leu Val Asp Phe Arg Glu Leu Asn Lys Arg Thr Gln
            660                 665                 670

Asp Phe Trp Glu Val Gln Leu Gly Ile Pro His Pro Ala Gly Leu Lys
        675                 680                 685

Lys Lys Lys Ser Val Thr Val Leu Asp Val Gly Asp Ala Tyr Phe Ser
    690                 695                 700

Val Pro Leu Asp Glu Asp Phe Arg Lys Tyr Thr Ala Phe Thr Ile Pro
705                 710                 715                 720

Ser Ile Asn Asn Glu Thr Pro Gly Ile Arg Tyr Gln Tyr Asn Val Leu
```

-continued

```
                725                 730                 735
Pro Gln Gly Trp Lys Gly Ser Pro Ala Ile Phe Gln Ser Met Thr
            740                 745                 750

Lys Ile Leu Glu Pro Phe Arg Lys Gln Asn Pro Asp Ile Val Ile Tyr
        755                 760                 765

Gln Tyr Met Asp Asp Leu Tyr Val Gly Ser Asp Leu Glu Ile Gly Gln
        770                 775                 780

His Arg Thr Lys Ile Glu Glu Leu Arg Gln His Leu Leu Arg Trp Gly
785                 790                 795                 800

Leu Thr Thr Pro Asp Lys Lys His Gln Lys Glu Pro Pro Phe Leu Trp
                805                 810                 815

Met Gly Tyr Glu Leu His Pro Asp Lys Trp Thr Val Gln Pro Ile Val
            820                 825                 830

Leu Pro Glu Lys Asp Ser Trp Thr Val Asn Asp Ile Gln Lys Leu Val
        835                 840                 845

Gly Lys Leu Asn Trp Ala Ser Gln Ile Tyr Pro Gly Ile Lys Val Arg
        850                 855                 860

Gln Leu Cys Lys Leu Leu Arg Gly Thr Lys Ala Leu Thr Glu Val Ile
865                 870                 875                 880

Pro Leu Thr Glu Glu Ala Glu Leu Glu Leu Ala Glu Asn Arg Glu Ile
                885                 890                 895

Leu Lys Glu Pro Val His Gly Val Tyr Tyr Asp Pro Ser Lys Asp Leu
            900                 905                 910

Ile Ala Glu Ile Gln Lys Gln Gly Gln Gly Gln Trp Thr Tyr Gln Ile
        915                 920                 925

Tyr Gln Glu Pro Phe Lys Asn Leu Lys Thr Gly Lys Tyr Ala Arg Met
        930                 935                 940

Arg Gly Ala His Thr Asn Asp Val Lys Gln Leu Thr Glu Ala Val Gln
945                 950                 955                 960

Lys Ile Thr Thr Glu Ser Ile Val Ile Trp Gly Lys Thr Pro Lys Phe
                965                 970                 975

Lys Leu Pro Ile Gln Lys Glu Thr Trp Glu Thr Trp Trp Thr Glu Tyr
            980                 985                 990

Trp Gln Ala Thr Trp Ile Pro Glu Trp Glu Phe Val Asn Thr Pro Pro
        995                 1000                1005

Leu Val Lys Leu Trp Tyr Gln Leu Glu Lys Glu Pro Ile Val Gly
        1010                1015                1020

Ala Glu Thr Phe Tyr Val Asp Gly Ala Ala Asn Arg Glu Thr Lys
        1025                1030                1035

Leu Gly Lys Ala Gly Tyr Val Thr Asn Arg Gly Arg Gln Lys Val
        1040                1045                1050

Val Thr Leu Thr Asp Thr Thr Asn Gln Lys Thr Glu Leu Gln Ala
        1055                1060                1065

Ile Tyr Leu Ala Leu Gln Asp Ser Gly Leu Glu Val Asn Ile Val
        1070                1075                1080

Thr Asp Ser Gln Tyr Ala Leu Gly Ile Ile Gln Ala Gln Pro Asp
        1085                1090                1095

Gln Ser Glu Ser Glu Leu Val Asn Gln Ile Ile Glu Gln Leu Ile
        1100                1105                1110

Lys Lys Glu Lys Val Tyr Leu Ala Trp Val Pro Ala His Lys Gly
        1115                1120                1125

Ile Gly Gly Asn Glu Gln Val Asp Lys Leu Val Ser Ala Gly Ile
        1130                1135                1140
```

```
Arg Lys Val Leu Phe Leu Asp Gly Ile Asp Lys Ala Gln Asp Glu
1145                1150                1155
His Glu Lys Tyr His Ser Asn Trp Arg Ala Met Ala Ser Asp Phe
    1160                1165                1170
Asn Leu Pro Pro Val Val Ala Lys Glu Ile Val Ala Ser Cys Asp
    1175                1180                1185
Lys Cys Gln Leu Lys Gly Glu Ala Met His Gly Gln Val Asp Cys
    1190                1195                1200
Ser Pro Gly Ile Trp Gln Leu Asp Cys Thr His Leu Glu Gly Lys
    1205                1210                1215
Val Ile Leu Val Ala Val His Val Ala Ser Gly Tyr Ile Glu Ala
    1220                1225                1230
Glu Val Ile Pro Ala Glu Thr Gly Gln Glu Thr Ala Tyr Phe Leu
    1235                1240                1245
Leu Lys Leu Ala Gly Arg Trp Pro Val Lys Thr Ile His Thr Asp
    1250                1255                1260
Asn Gly Ser Asn Phe Thr Gly Ala Thr Val Arg Ala Ala Cys Trp
    1265                1270                1275
Trp Ala Gly Ile Lys Gln Glu Phe Gly Ile Pro Tyr Asn Pro Gln
    1280                1285                1290
Ser Gln Gly Val Val Glu Ser Met Asn Lys Glu Leu Lys Lys Ile
    1295                1300                1305
Ile Gly Gln Val Arg Asp Gln Ala Glu His Leu Lys Thr Ala Val
    1310                1315                1320
Gln Met Ala Val Phe Ile His Asn Phe Lys Arg Lys Gly Gly Ile
    1325                1330                1335
Gly Gly Tyr Ser Ala Gly Glu Arg Ile Val Asp Ile Ile Ala Thr
    1340                1345                1350
Asp Ile Gln Thr Lys Glu Leu Gln Lys Gln Ile Thr Lys Ile Gln
    1355                1360                1365
Asn Phe Arg Val Tyr Tyr Arg Asp Ser Arg Asn Pro Leu Trp Lys
    1370                1375                1380
Gly Pro Ala Lys Leu Leu Trp Lys Gly Glu Gly Ala Val Val Ile
    1385                1390                1395
Gln Asp Asn Ser Asp Ile Lys Val Val Pro Arg Arg Lys Ala Lys
    1400                1405                1410
Ile Ile Arg Asp Tyr Gly Lys Gln Met Ala Gly Asp Asp Cys Val
    1415                1420                1425
Ala Ser Arg Gln Asp Glu Asp
    1430                1435

<210> SEQ ID NO 21
<211> LENGTH: 856
<212> TYPE: PRT
<213> ORGANISM: Human immunodeficiency virus type 1

<400> SEQUENCE: 21

Met Arg Val Lys Glu Lys Tyr Gln His Leu Trp Arg Trp Gly Trp
1               5                   10                  15

Trp Gly Thr Met Leu Leu Gly Met Leu Met Ile Cys Ser Ala Thr Glu
                20                  25                  30

Lys Leu Trp Val Thr Val Tyr Tyr Gly Val Pro Val Trp Lys Glu Ala
            35                  40                  45

Thr Thr Thr Leu Phe Cys Ala Ser Asp Ala Lys Ala Tyr Asp Thr Glu
        50                  55                  60
```

-continued

Val His Asn Val Trp Ala Thr His Ala Cys Val Pro Thr Asp Pro Asn
65              70                  75                  80

Pro Gln Glu Val Val Leu Val Asn Val Thr Glu Phe Asn Met Trp
            85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
            115                 120                 125

Leu Lys Cys Thr Asp Leu Lys Asn Asp Thr Asn Thr Asn Ser Ser Ser
130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
            195                 200                 205

Ser Phe Glu Pro Ile Pro Ile His Tyr Cys Ala Pro Ala Gly Phe Ala
210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
            275                 280                 285

Asn Thr Ser Val Glu Ile Asn Cys Thr Arg Pro Asn Asn Asn Thr Arg
290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
            355                 360                 365

Pro Glu Ile Val Thr His Ser Phe Asn Cys Gly Gly Glu Phe Phe Tyr
            370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
            435                 440                 445

Ile Thr Gly Leu Leu Leu Thr Arg Asp Gly Gly Asn Ser Asn Asn Glu
450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

```
Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
        515                 520                 525

Thr Met Gly Ala Ala Ser Met Thr Leu Thr Val Gln Ala Arg Gln Leu
    530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
        595                 600                 605

Pro Trp Asn Ala Ser Trp Ser Asn Lys Ser Leu Glu Gln Ile Trp Asn
    610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
        675                 680                 685

Val Gly Gly Leu Val Gly Leu Arg Ile Val Phe Ala Val Leu Ser Ile
    690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
        755                 760                 765

His Arg Leu Arg Asp Leu Leu Leu Ile Val Thr Arg Ile Val Glu Leu
    770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
        835                 840                 845

Gln Gly Leu Glu Arg Ile Leu Leu
    850                 855

<210> SEQ ID NO 22
<211> LENGTH: 192
<212> TYPE: PRT
<213> ORGANISM: Human immunodeficiency virus type 1

<400> SEQUENCE: 22

Met Glu Asn Arg Trp Gln Val Met Ile Val Trp Gln Val Asp Arg Met
1               5                   10                  15
```

```
Arg Ile Arg Thr Trp Lys Ser Leu Val Lys His His Met Tyr Val Ser
            20                  25                  30

Gly Lys Ala Arg Gly Trp Phe Tyr Arg His His Tyr Glu Ser Pro His
        35                  40                  45

Pro Arg Ile Ser Ser Glu Val His Ile Pro Leu Gly Asp Ala Arg Leu
    50                  55                  60

Val Ile Thr Thr Tyr Trp Gly Leu His Thr Gly Glu Arg Asp Trp His
 65                  70                  75                  80

Leu Gly Gln Gly Val Ser Ile Glu Trp Arg Lys Lys Arg Tyr Ser Thr
                85                  90                  95

Gln Val Asp Pro Glu Leu Ala Asp Gln Leu Ile His Leu Tyr Tyr Phe
            100                 105                 110

Asp Cys Phe Ser Asp Ser Ala Ile Arg Lys Ala Leu Leu Gly His Ile
        115                 120                 125

Val Ser Pro Arg Cys Glu Tyr Gln Ala Gly His Asn Lys Val Gly Ser
    130                 135                 140

Leu Gln Tyr Leu Ala Leu Ala Ala Leu Ile Thr Pro Lys Lys Ile Lys
145                 150                 155                 160

Pro Pro Leu Pro Ser Val Thr Lys Leu Thr Glu Asp Arg Trp Asn Lys
                165                 170                 175

Pro Gln Lys Thr Lys Gly His Arg Gly Ser His Thr Met Asn Gly His
            180                 185                 190

<210> SEQ ID NO 23
<211> LENGTH: 86
<212> TYPE: PRT
<213> ORGANISM: Human immunodeficiency virus type 1

<400> SEQUENCE: 23

Met Glu Pro Val Asp Pro Arg Leu Glu Pro Trp Lys His Pro Gly Ser
 1               5                  10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Ala His Gln Asn Ser Gln Thr
    50                  55                  60

His Gln Ala Ser Leu Ser Lys Gln Pro Thr Ser Gln Pro Arg Gly Asp
 65                  70                  75                  80

Pro Thr Gly Pro Lys Glu
                85

<210> SEQ ID NO 24
<211> LENGTH: 116
<212> TYPE: PRT
<213> ORGANISM: Human immunodeficiency virus type 1

<400> SEQUENCE: 24

Met Ala Gly Arg Ser Gly Asp Ser Asp Glu Glu Leu Ile Arg Thr Val
 1               5                  10                  15

Arg Leu Ile Lys Leu Leu Tyr Gln Ser Asn Pro Pro Asn Pro Glu
            20                  25                  30

Gly Thr Arg Gln Ala Arg Arg Asn Arg Arg Arg Trp Arg Glu Arg
        35                  40                  45

Gln Arg Gln Ile His Ser Ile Ser Glu Arg Ile Leu Gly Thr Tyr Leu
    50                  55                  60
```

```
Gly Arg Ser Ala Glu Pro Val Pro Leu Gln Leu Pro Leu Glu Arg
 65                  70                  75                  80

Leu Thr Leu Asp Cys Asn Glu Asp Cys Gly Thr Ser Gly Thr Gln Gly
                 85                  90                  95

Val Gly Ser Pro Gln Ile Leu Val Glu Ser Pro Thr Val Leu Glu Ser
            100                 105                 110

Gly Thr Lys Glu
        115

<210> SEQ ID NO 25
<211> LENGTH: 96
<212> TYPE: PRT
<213> ORGANISM: Human immunodeficiency virus type 1

<400> SEQUENCE: 25

Met Glu Gln Ala Pro Glu Asp Gln Gly Pro Gln Arg Glu Pro His Asn
 1               5                  10                  15

Glu Trp Thr Leu Glu Leu Leu Glu Leu Lys Asn Glu Ala Val Arg
             20                  25                  30

His Phe Pro Arg Ile Trp Leu His Gly Leu Gly Gln His Ile Tyr Glu
             35                  40                  45

Thr Tyr Gly Asp Thr Trp Ala Gly Val Glu Ala Ile Arg Ile Leu
 50                  55                  60

Gln Gln Leu Leu Phe Ile His Phe Arg Ile Gly Cys Arg His Ser Arg
 65                  70                  75                  80

Ile Gly Val Thr Arg Gln Arg Arg Ala Arg Asn Gly Ala Ser Arg Ser
                 85                  90                  95

<210> SEQ ID NO 26
<211> LENGTH: 82
<212> TYPE: PRT
<213> ORGANISM: Human immunodeficiency virus type 1

<400> SEQUENCE: 26

Met Gln Pro Ile Pro Ile Val Ala Ile Val Ala Leu Val Val Ala Ile
 1               5                  10                  15

Ile Ile Ala Ile Val Val Trp Ser Ile Val Ile Ile Glu Tyr Arg Lys
             20                  25                  30

Ile Leu Arg Gln Arg Lys Ile Asp Arg Leu Ile Asp Arg Leu Ile Glu
             35                  40                  45

Arg Ala Glu Asp Ser Gly Asn Glu Ser Glu Gly Glu Ile Ser Ala Leu
 50                  55                  60

Val Glu Met Gly Val Glu Met Gly His His Ala Pro Trp Asp Val Asp
 65                  70                  75                  80

Asp Leu

<210> SEQ ID NO 27
<211> LENGTH: 206
<212> TYPE: PRT
<213> ORGANISM: Human immunodeficiency virus type 1

<400> SEQUENCE: 27

Met Gly Gly Lys Trp Ser Lys Ser Ser Val Ile Gly Trp Pro Thr Val
 1               5                  10                  15

Arg Glu Arg Met Arg Arg Ala Glu Pro Ala Ala Asp Arg Val Gly Ala
             20                  25                  30

Ala Ser Arg Asp Leu Glu Lys His Gly Ala Ile Thr Ser Ser Asn Thr
             35                  40                  45
```

```
Ala Ala Thr Asn Ala Ala Cys Ala Trp Leu Glu Ala Gln Glu Glu Glu
         50                  55                  60

Glu Val Gly Phe Pro Val Thr Pro Gln Val Pro Leu Arg Pro Met Thr
 65                  70                  75                  80

Tyr Lys Ala Ala Val Asp Leu Ser His Phe Leu Lys Glu Lys Gly Gly
                 85                  90                  95

Leu Glu Gly Leu Ile His Ser Gln Arg Arg Gln Asp Ile Leu Asp Leu
            100                 105                 110

Trp Ile Tyr His Thr Gln Gly Tyr Phe Pro Asp Trp Gln Asn Tyr Thr
            115                 120                 125

Pro Gly Pro Gly Val Arg Tyr Pro Leu Thr Phe Gly Trp Cys Tyr Lys
        130                 135                 140

Leu Val Pro Val Glu Pro Asp Lys Ile Glu Glu Ala Asn Lys Gly Glu
145                 150                 155                 160

Asn Thr Ser Leu Leu His Pro Val Ser Leu His Gly Met Asp Asp Pro
                165                 170                 175

Glu Arg Glu Val Leu Glu Trp Arg Phe Asp Ser Arg Leu Ala Phe His
            180                 185                 190

His Val Ala Arg Glu Leu His Pro Glu Tyr Phe Lys Asn Cys
        195                 200                 205

<210> SEQ ID NO 28
<211> LENGTH: 995
<212> TYPE: PRT
<213> ORGANISM: Human immunodeficiency virus type 1

<400> SEQUENCE: 28

Leu Gln Gly Lys Ala Arg Glu Phe Ser Glu Gln Thr Arg Ala Asn
 1               5                  10                  15

Ser Pro Thr Arg Arg Glu Leu Gln Val Trp Gly Arg Asp Asn Asn Ser
                 20                  25                  30

Pro Ser Glu Ala Gly Ala Asp Arg Gln Gly Thr Val Ser Phe Asn Phe
             35                  40                  45

Pro Gln Val Thr Leu Trp Gln Arg Pro Leu Val Thr Ile Lys Ile Gly
         50                  55                  60

Gly Gln Leu Lys Glu Ala Leu Leu Asp Thr Gly Ala Asp Asp Thr Val
 65                  70                  75                  80

Leu Glu Glu Met Ser Leu Pro Gly Arg Trp Lys Pro Lys Met Ile Gly
                 85                  90                  95

Gly Ile Gly Gly Phe Ile Lys Val Arg Gln Tyr Asp Gln Ile Leu Ile
            100                 105                 110

Glu Ile Cys Gly His Lys Ala Ile Gly Thr Val Leu Val Gly Pro Thr
            115                 120                 125

Pro Val Asn Ile Ile Gly Arg Asn Leu Leu Thr Gln Ile Gly Cys Thr
        130                 135                 140

Leu Asn Phe Pro Ile Ser Pro Ile Glu Thr Val Pro Val Lys Leu Lys
145                 150                 155                 160

Pro Gly Met Asp Gly Pro Lys Val Lys Gln Trp Pro Leu Thr Glu Glu
                165                 170                 175

Lys Ile Lys Ala Leu Val Glu Ile Cys Thr Glu Met Glu Lys Glu Gly
            180                 185                 190

Lys Ile Ser Lys Ile Gly Pro Glu Asn Pro Tyr Asn Thr Pro Val Phe
        195                 200                 205

Ala Ile Lys Lys Lys Asp Ser Thr Lys Trp Arg Lys Leu Val Asp Phe
210                 215                 220
```

-continued

```
Arg Glu Leu Asn Lys Arg Thr Gln Asp Phe Trp Glu Val Gln Leu Gly
225                 230                 235                 240

Ile Pro His Pro Ala Gly Leu Lys Lys Lys Ser Val Thr Val Leu
            245                 250                 255

Asp Val Gly Asp Ala Tyr Phe Ser Val Pro Leu Asp Glu Asp Phe Arg
            260                 265                 270

Lys Tyr Thr Ala Phe Thr Ile Pro Ser Ile Asn Asn Glu Thr Pro Gly
            275                 280                 285

Ile Arg Tyr Gln Tyr Asn Val Leu Pro Gln Gly Trp Lys Gly Ser Pro
            290                 295                 300

Ala Ile Phe Gln Ser Ser Met Thr Lys Ile Leu Glu Pro Phe Arg Lys
305                 310                 315                 320

Gln Asn Pro Asp Ile Val Ile Tyr Gln Tyr Met Asp Asp Leu Tyr Val
            325                 330                 335

Gly Ser Asp Leu Glu Ile Gly Gln His Arg Thr Lys Ile Glu Glu Leu
            340                 345                 350

Arg Gln His Leu Leu Arg Trp Gly Leu Thr Thr Pro Asp Lys Lys His
            355                 360                 365

Gln Lys Glu Pro Pro Phe Leu Trp Met Gly Tyr Glu Leu His Pro Asp
370                 375                 380

Lys Trp Thr Val Gln Pro Ile Val Leu Pro Glu Lys Asp Ser Trp Thr
385                 390                 395                 400

Val Asn Asp Ile Gln Lys Leu Val Gly Lys Leu Asn Trp Ala Ser Gln
            405                 410                 415

Ile Tyr Pro Gly Ile Lys Val Arg Gln Leu Cys Lys Leu Leu Arg Gly
            420                 425                 430

Thr Lys Ala Leu Thr Glu Val Ile Pro Leu Thr Glu Glu Ala Glu Leu
            435                 440                 445

Glu Leu Ala Glu Asn Arg Glu Ile Leu Lys Glu Pro Val His Gly Val
            450                 455                 460

Tyr Tyr Asp Pro Ser Lys Asp Leu Ile Ala Glu Ile Gln Lys Gln Gly
465                 470                 475                 480

Gln Gly Gln Trp Thr Tyr Gln Ile Tyr Gln Glu Pro Phe Lys Asn Leu
            485                 490                 495

Lys Thr Gly Lys Tyr Ala Arg Met Arg Gly Ala His Thr Asn Asp Val
            500                 505                 510

Lys Gln Leu Thr Glu Ala Val Gln Lys Ile Thr Thr Glu Ser Ile Val
            515                 520                 525

Ile Trp Gly Lys Thr Pro Lys Phe Lys Leu Pro Ile Gln Lys Glu Thr
            530                 535                 540

Trp Glu Thr Trp Trp Thr Glu Tyr Trp Gln Ala Thr Trp Ile Pro Glu
545                 550                 555                 560

Trp Glu Phe Val Asn Thr Pro Pro Leu Val Lys Leu Trp Tyr Gln Leu
            565                 570                 575

Glu Lys Glu Pro Ile Val Gly Ala Glu Thr Phe Tyr Val Asp Gly Ala
            580                 585                 590

Ala Asn Arg Glu Thr Lys Leu Gly Lys Ala Gly Tyr Val Thr Asn Arg
            595                 600                 605

Gly Arg Gln Lys Val Val Thr Leu Thr Asp Thr Thr Asn Gln Lys Thr
            610                 615                 620

Glu Leu Gln Ala Ile Tyr Leu Ala Leu Gln Asp Ser Gly Leu Glu Val
625                 630                 635                 640

Asn Ile Val Thr Asp Ser Gln Tyr Ala Leu Gly Ile Ile Gln Ala Gln
            645                 650                 655
```

Pro Asp Gln Ser Glu Ser Glu Leu Val Asn Gln Ile Ile Glu Gln Leu
                660                 665                 670

Ile Lys Lys Glu Lys Val Tyr Leu Ala Trp Val Pro Ala His Lys Gly
        675                 680                 685

Ile Gly Gly Asn Glu Gln Val Asp Lys Leu Val Ser Ala Gly Ile Arg
    690                 695                 700

Lys Val Leu Phe Leu Asp Gly Ile Asp Lys Ala Gln Asp Glu His Glu
705                 710                 715                 720

Lys Tyr His Ser Asn Trp Arg Ala Met Ala Ser Asp Phe Asn Leu Pro
                725                 730                 735

Pro Val Val Ala Lys Glu Ile Val Ala Ser Cys Asp Lys Cys Gln Leu
            740                 745                 750

Lys Gly Glu Ala Met His Gly Gln Val Asp Cys Ser Pro Gly Ile Trp
        755                 760                 765

Gln Leu Asp Cys Thr His Leu Glu Gly Lys Val Ile Leu Val Ala Val
    770                 775                 780

His Val Ala Ser Gly Tyr Ile Glu Ala Glu Val Ile Pro Ala Glu Thr
785                 790                 795                 800

Gly Gln Glu Thr Ala Tyr Phe Leu Leu Lys Leu Ala Gly Arg Trp Pro
                805                 810                 815

Val Lys Thr Ile His Thr Asp Asn Gly Ser Asn Phe Thr Gly Ala Thr
            820                 825                 830

Val Arg Ala Ala Cys Trp Trp Ala Gly Ile Lys Gln Glu Phe Gly Ile
        835                 840                 845

Pro Tyr Asn Pro Gln Ser Gln Gly Val Val Glu Ser Met Asn Lys Glu
850                 855                 860

Leu Lys Lys Ile Ile Gly Gln Val Arg Asp Gln Ala Glu His Leu Lys
865                 870                 875                 880

Thr Ala Val Gln Met Ala Val Phe Ile His Asn Phe Lys Arg Lys Gly
                885                 890                 895

Gly Ile Gly Gly Tyr Ser Ala Gly Glu Arg Ile Val Asp Ile Ile Ala
            900                 905                 910

Thr Asp Ile Gln Thr Lys Glu Leu Gln Lys Gln Ile Thr Lys Ile Gln
        915                 920                 925

Asn Phe Arg Val Tyr Tyr Arg Asp Ser Arg Asn Pro Leu Trp Lys Gly
    930                 935                 940

Pro Ala Lys Leu Leu Trp Lys Gly Glu Gly Ala Val Val Ile Gln Asp
945                 950                 955                 960

Asn Ser Asp Ile Lys Val Val Pro Arg Arg Lys Ala Lys Ile Ile Arg
                965                 970                 975

Asp Tyr Gly Lys Gln Met Ala Gly Asp Asp Cys Val Ala Ser Arg Gln
            980                 985                 990

Asp Glu Asp
        995

<210> SEQ ID NO 29
<211> LENGTH: 440
<212> TYPE: PRT
<213> ORGANISM: Human immunodeficiency virus type 1

<400> SEQUENCE: 29

Pro Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
            20                  25                  30

-continued

```
Ala Leu Val Glu Ile Cys Thr Glu Met Glu Lys Glu Gly Lys Ile Ser
            35                  40                  45
Lys Ile Gly Pro Glu Asn Pro Tyr Asn Thr Pro Val Phe Ala Ile Lys
 50                  55                  60
Lys Lys Asp Ser Thr Lys Trp Arg Lys Leu Val Asp Phe Arg Glu Leu
 65                  70                  75                  80
Asn Lys Arg Thr Gln Asp Phe Trp Glu Val Gln Leu Gly Ile Pro His
                    85                  90                  95
Pro Ala Gly Leu Lys Lys Lys Ser Val Thr Val Leu Asp Val Gly
            100                 105                 110
Asp Ala Tyr Phe Ser Val Pro Leu Asp Glu Asp Phe Arg Lys Tyr Thr
            115                 120                 125
Ala Phe Thr Ile Pro Ser Ile Asn Asn Glu Thr Pro Gly Ile Arg Tyr
            130                 135                 140
Gln Tyr Asn Val Leu Pro Gln Gly Trp Lys Gly Ser Pro Ala Ile Phe
145                 150                 155                 160
Gln Ser Ser Met Thr Lys Ile Leu Glu Pro Phe Arg Lys Gln Asn Pro
                165                 170                 175
Asp Ile Val Ile Tyr Gln Tyr Met Asp Asp Leu Tyr Val Gly Ser Asp
            180                 185                 190
Leu Glu Ile Gly Gln His Arg Thr Lys Ile Glu Glu Leu Arg Gln His
            195                 200                 205
Leu Leu Arg Trp Gly Leu Thr Thr Pro Asp Lys Lys His Gln Lys Glu
            210                 215                 220
Pro Pro Phe Leu Trp Met Gly Tyr Glu Leu His Pro Asp Lys Trp Thr
225                 230                 235                 240
Val Gln Pro Ile Val Leu Pro Glu Lys Asp Ser Trp Thr Val Asn Asp
                245                 250                 255
Ile Gln Lys Leu Val Gly Lys Leu Asn Trp Ala Ser Gln Ile Tyr Pro
            260                 265                 270
Gly Ile Lys Val Arg Gln Leu Cys Lys Leu Leu Arg Gly Thr Lys Ala
            275                 280                 285
Leu Thr Glu Val Ile Pro Leu Thr Glu Glu Ala Glu Leu Glu Leu Ala
            290                 295                 300
Glu Asn Arg Glu Ile Leu Lys Glu Pro Val His Gly Val Tyr Tyr Asp
305                 310                 315                 320
Pro Ser Lys Asp Leu Ile Ala Glu Ile Gln Lys Gln Gly Gln Gly Gln
                325                 330                 335
Trp Thr Tyr Gln Ile Tyr Gln Glu Pro Phe Lys Asn Leu Lys Thr Gly
            340                 345                 350
Lys Tyr Ala Arg Met Arg Gly Ala His Thr Asn Asp Val Lys Gln Leu
            355                 360                 365
Thr Glu Ala Val Gln Lys Ile Thr Thr Glu Ser Ile Val Ile Trp Gly
            370                 375                 380
Lys Thr Pro Lys Phe Lys Leu Pro Ile Gln Lys Glu Thr Trp Glu Thr
385                 390                 395                 400
Trp Trp Thr Glu Tyr Trp Gln Ala Thr Trp Ile Pro Glu Trp Glu Phe
                405                 410                 415
Val Asn Thr Pro Pro Leu Val Lys Leu Trp Tyr Gln Leu Glu Lys Glu
            420                 425                 430
Pro Ile Val Gly Ala Glu Thr Phe
            435                 440
```

-continued

```
<210> SEQ ID NO 30
<211> LENGTH: 288
<212> TYPE: PRT
<213> ORGANISM: Human immunodeficiency virus type 1

<400> SEQUENCE: 30

Phe Leu Asp Gly Ile Asp Lys Ala Gln Asp Glu His Glu Lys Tyr His
1               5                   10                  15

Ser Asn Trp Arg Ala Met Ala Ser Asp Phe Asn Leu Pro Pro Val Val
            20                  25                  30

Ala Lys Glu Ile Val Ala Ser Cys Asp Lys Cys Gln Leu Lys Gly Glu
        35                  40                  45

Ala Met His Gly Gln Val Asp Cys Ser Pro Gly Ile Trp Gln Leu Asp
    50                  55                  60

Cys Thr His Leu Glu Gly Lys Val Ile Leu Val Ala Val His Val Ala
65                  70                  75                  80

Ser Gly Tyr Ile Glu Ala Glu Val Ile Pro Ala Glu Thr Gly Gln Glu
                85                  90                  95

Thr Ala Tyr Phe Leu Leu Lys Leu Ala Gly Arg Trp Pro Val Lys Thr
            100                 105                 110

Ile His Thr Asp Asn Gly Ser Asn Phe Thr Gly Ala Thr Val Arg Ala
        115                 120                 125

Ala Cys Trp Trp Ala Gly Ile Lys Gln Glu Phe Gly Ile Pro Tyr Asn
    130                 135                 140

Pro Gln Ser Gln Gly Val Val Glu Ser Met Asn Lys Glu Leu Lys Lys
145                 150                 155                 160

Ile Ile Gly Gln Val Arg Asp Gln Ala Glu His Leu Lys Thr Ala Val
                165                 170                 175

Gln Met Ala Val Phe Ile His Asn Phe Lys Arg Lys Gly Gly Ile Gly
            180                 185                 190

Gly Tyr Ser Ala Gly Glu Arg Ile Val Asp Ile Ile Ala Thr Asp Ile
        195                 200                 205

Gln Thr Lys Glu Leu Gln Lys Gln Ile Thr Lys Ile Gln Asn Phe Arg
    210                 215                 220

Val Tyr Tyr Arg Asp Ser Arg Asn Pro Leu Trp Lys Gly Pro Ala Lys
225                 230                 235                 240

Leu Leu Trp Lys Gly Glu Gly Ala Val Val Ile Gln Asp Asn Ser Asp
                245                 250                 255

Ile Lys Val Val Pro Arg Arg Lys Ala Lys Ile Ile Arg Asp Tyr Gly
            260                 265                 270

Lys Gln Met Ala Gly Asp Asp Cys Val Ala Ser Arg Gln Asp Glu Asp
        275                 280                 285

<210> SEQ ID NO 31
<211> LENGTH: 56
<212> TYPE: PRT
<213> ORGANISM: Human immunodeficiency virus type 1

<400> SEQUENCE: 31

Phe Leu Arg Glu Asp Leu Ala Phe Leu Gln Gly Lys Ala Arg Glu Phe
1               5                   10                  15

Ser Ser Glu Gln Thr Arg Ala Asn Ser Pro Thr Arg Arg Glu Leu Gln
            20                  25                  30

Val Trp Gly Arg Asp Asn Asn Ser Pro Ser Glu Ala Gly Ala Asp Arg
        35                  40                  45

Gln Gly Thr Val Ser Phe Asn Phe
    50                  55
```

<210> SEQ ID NO 32
<211> LENGTH: 99
<212> TYPE: PRT
<213> ORGANISM: Human immunodeficiency virus type 1

<400> SEQUENCE: 32

Pro Gln Val Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Ser Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 33
<211> LENGTH: 560
<212> TYPE: PRT
<213> ORGANISM: Human immunodeficiency virus type 1

<400> SEQUENCE: 33

Pro Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
            20                  25                  30

Ala Leu Val Glu Ile Cys Thr Glu Met Glu Lys Glu Gly Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Lys Lys Ser Val Thr Val Leu Asp Val Gly
            100                 105                 110

Asp Ala Tyr Phe Ser Val Pro Leu Asp Glu Asp Phe Arg Lys Tyr Thr
        115                 120                 125

Ala Phe Thr Ile Pro Ser Ile Asn Asn Glu Thr Pro Gly Ile Arg Tyr
    130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Arg Lys Gln Asn Pro
                165                 170                 175

Asp Ile Val Ile Tyr Gln Tyr Met Asp Asp Leu Tyr Val Gly Ser Asp
            180                 185                 190

Leu Glu Ile Gly Gln His Arg Thr Lys Ile Glu Glu Leu Arg Gln His
        195                 200                 205

Leu Leu Arg Trp Gly Leu Thr Thr Pro Asp Lys Lys His Gln Lys Glu
    210                 215                 220

Pro Pro Phe Leu Trp Met Gly Tyr Glu Leu His Pro Asp Lys Trp Thr

```
                225                 230                 235                 240
Val Gln Pro Ile Val Leu Pro Glu Lys Asp Ser Trp Thr Val Asn Asp
                245                 250                 255

Ile Gln Lys Leu Val Gly Lys Leu Asn Trp Ala Ser Gln Ile Tyr Pro
            260                 265                 270

Gly Ile Lys Val Arg Gln Leu Cys Lys Leu Leu Arg Gly Thr Lys Ala
        275                 280                 285

Leu Thr Glu Val Ile Pro Leu Thr Glu Glu Ala Glu Leu Glu Leu Ala
    290                 295                 300

Glu Asn Arg Glu Ile Leu Lys Glu Pro Val His Gly Val Tyr Tyr Asp
305                 310                 315                 320

Pro Ser Lys Asp Leu Ile Ala Glu Ile Gln Lys Gln Gly Gln Gly Gln
                325                 330                 335

Trp Thr Tyr Gln Ile Tyr Gln Glu Pro Phe Lys Asn Leu Lys Thr Gly
            340                 345                 350

Lys Tyr Ala Arg Met Arg Gly Ala His Thr Asn Asp Val Lys Gln Leu
        355                 360                 365

Thr Glu Ala Val Gln Lys Ile Thr Thr Glu Ser Ile Val Ile Trp Gly
    370                 375                 380

Lys Thr Pro Lys Phe Lys Leu Pro Ile Gln Lys Glu Thr Trp Glu Thr
385                 390                 395                 400

Trp Trp Thr Glu Tyr Trp Gln Ala Thr Trp Ile Pro Glu Trp Glu Phe
                405                 410                 415

Val Asn Thr Pro Pro Leu Val Lys Leu Trp Tyr Gln Leu Glu Lys Glu
            420                 425                 430

Pro Ile Val Gly Ala Glu Thr Phe Tyr Val Asp Gly Ala Ala Asn Arg
        435                 440                 445

Glu Thr Lys Leu Gly Lys Ala Gly Tyr Val Thr Asn Arg Gly Arg Gln
    450                 455                 460

Lys Val Val Thr Leu Thr Asp Thr Thr Asn Gln Lys Thr Glu Leu Gln
465                 470                 475                 480

Ala Ile Tyr Leu Ala Leu Gln Asp Ser Gly Leu Glu Val Asn Ile Val
                485                 490                 495

Thr Asp Ser Gln Tyr Ala Leu Gly Ile Ile Gln Ala Gln Pro Asp Gln
            500                 505                 510

Ser Glu Ser Glu Leu Val Asn Gln Ile Ile Glu Gln Leu Ile Lys Lys
        515                 520                 525

Glu Lys Val Tyr Leu Ala Trp Val Pro Ala His Lys Gly Ile Gly Gly
    530                 535                 540

Asn Glu Gln Val Asp Lys Leu Val Ser Ala Gly Ile Arg Lys Val Leu
545                 550                 555                 560

<210> SEQ ID NO 34
<211> LENGTH: 1550
<212> TYPE: PRT
<213> ORGANISM: Human immunodeficiency virus type 2

<400> SEQUENCE: 34

Met Gly Ala Arg Asn Ser Val Leu Arg Gly Lys Lys Ala Asp Glu Leu
1               5                   10                  15

Glu Lys Val Arg Leu Arg Pro Gly Gly Lys Lys Lys Tyr Arg Leu Lys
            20                  25                  30

His Ile Val Trp Ala Ala Asn Glu Leu Asp Lys Phe Gly Leu Ala Glu
        35                  40                  45

Ser Leu Leu Glu Ser Lys Glu Gly Cys Gln Lys Ile Leu Arg Val Leu
```

```
                50                   55                   60
Asp Pro Leu Val Pro Thr Gly Ser Glu Asn Leu Lys Ser Leu Phe Asn
65                  70                  75                  80

Thr Val Cys Val Ile Trp Cys Leu His Ala Glu Glu Lys Val Lys Asp
                    85                  90                  95

Thr Glu Glu Ala Lys Lys Leu Ala Gln Arg His Leu Val Ala Glu Thr
                100                 105                 110

Gly Thr Ala Glu Lys Met Pro Asn Thr Ser Arg Pro Thr Ala Pro Pro
                115                 120                 125

Ser Gly Lys Arg Gly Asn Tyr Pro Val Gln Gln Ala Gly Gly Asn Tyr
130                 135                 140

Val His Val Pro Leu Ser Pro Arg Thr Leu Asn Ala Trp Val Lys Leu
145                 150                 155                 160

Val Glu Glu Lys Lys Phe Gly Ala Glu Val Val Pro Gly Phe Gln Ala
                165                 170                 175

Leu Ser Glu Gly Cys Thr Pro Tyr Asp Ile Asn Gln Met Leu Asn Cys
                180                 185                 190

Val Gly Asp His Gln Ala Ala Met Gln Ile Ile Arg Glu Ile Ile Asn
                195                 200                 205

Glu Glu Ala Ala Asp Trp Asp Ser Gln His Pro Ile Pro Gly Pro Leu
210                 215                 220

Pro Ala Gly Gln Leu Arg Asp Pro Arg Gly Ser Asp Ile Ala Gly Thr
225                 230                 235                 240

Thr Ser Thr Val Asp Glu Gln Ile Gln Trp Met Tyr Arg Pro Gln Asn
                245                 250                 255

Pro Val Pro Val Gly Asn Ile Tyr Arg Arg Trp Ile Gln Ile Gly Leu
                260                 265                 270

Gln Lys Cys Val Arg Lys Tyr Asn Pro Thr Asn Ile Leu Asp Ile Lys
                275                 280                 285

Gln Gly Pro Lys Glu Pro Phe Gln Ser Tyr Val Asp Arg Phe Tyr Lys
290                 295                 300

Ser Leu Arg Ala Glu Gln Thr Asp Pro Ala Val Lys Asn Trp Met Thr
305                 310                 315                 320

Gln Thr Leu Leu Ile Gln Asn Ala Asn Pro Asp Cys Lys Leu Val Leu
                325                 330                 335

Lys Gly Leu Gly Met Asn Pro Thr Leu Glu Glu Met Leu Thr Ala Cys
                340                 345                 350

Gln Gly Val Gly Gly Pro Gly Gln Lys Ala Arg Leu Met Ala Glu Ala
                355                 360                 365

Leu Lys Glu Ala Met Gly Pro Ser Pro Ile Pro Phe Ala Ala Ala Gln
370                 375                 380

Gln Arg Lys Ala Ile Arg Tyr Trp Asn Cys Gly Lys Glu Gly His Ser
385                 390                 395                 400

Ala Arg Gln Cys Arg Ala Pro Arg Arg Gln Gly Cys Trp Lys Cys Gly
                405                 410                 415

Lys Pro Gly His Ile Met Ala Asn Cys Pro Glu Arg Gln Ala Gly Phe
                420                 425                 430

Phe Arg Val Gly Pro Thr Gly Lys Glu Ala Ser Gln Leu Pro Arg Asp
                435                 440                 445

Pro Ser Pro Ser Gly Ala Asp Thr Asn Ser Thr Ser Gly Arg Ser Ser
450                 455                 460

Ser Gly Thr Val Gly Glu Ile Tyr Ala Ala Arg Glu Lys Ala Glu Gly
465                 470                 475                 480
```

-continued

```
Ala Glu Gly Glu Thr Ile Gln Arg Gly Asp Gly Gly Leu Ala Ala Pro
                485                 490                 495

Arg Ala Glu Arg Asp Thr Ser Gln Arg Gly Asp Arg Gly Leu Ala Ala
            500                 505                 510

Pro Gln Phe Ser Leu Trp Lys Arg Pro Val Val Thr Ala Tyr Ile Glu
        515                 520                 525

Asp Gln Pro Val Glu Val Leu Leu Asp Thr Gly Ala Asp Asp Ser Ile
    530                 535                 540

Val Ala Gly Ile Glu Leu Gly Asp Asn Tyr Thr Pro Lys Ile Val Gly
545                 550                 555                 560

Gly Ile Gly Gly Phe Ile Asn Thr Lys Glu Tyr Lys Asn Val Glu Ile
                565                 570                 575

Lys Val Leu Asn Lys Arg Val Arg Ala Thr Ile Met Thr Gly Asp Thr
            580                 585                 590

Pro Ile Asn Ile Phe Gly Arg Asn Ile Leu Thr Ala Leu Gly Met Ser
        595                 600                 605

Leu Asn Leu Pro Val Ala Lys Ile Glu Pro Ile Lys Val Thr Leu Lys
    610                 615                 620

Pro Gly Lys Asp Gly Pro Arg Leu Lys Gln Trp Pro Leu Thr Lys Glu
625                 630                 635                 640

Lys Ile Glu Ala Leu Lys Glu Ile Cys Glu Lys Met Glu Lys Glu Gly
                645                 650                 655

Gln Leu Glu Glu Ala Pro Pro Thr Asn Pro Tyr Asn Thr Pro Thr Phe
            660                 665                 670

Ala Ile Lys Lys Lys Asp Lys Asn Lys Trp Arg Met Leu Ile Asp Phe
        675                 680                 685

Arg Glu Leu Asn Lys Val Thr Gln Asp Phe Thr Glu Ile Gln Leu Gly
    690                 695                 700

Ile Pro His Pro Ala Gly Leu Ala Lys Lys Arg Ile Ser Ile Leu
705                 710                 715                 720

Asp Val Gly Asp Ala Tyr Phe Ser Ile Pro Leu His Glu Asp Phe Arg
                725                 730                 735

Gln Tyr Thr Ala Phe Thr Leu Pro Ala Val Asn Asn Met Glu Pro Gly
            740                 745                 750

Lys Arg Tyr Ile Tyr Lys Val Leu Pro Gln Gly Trp Lys Gly Ser Pro
        755                 760                 765

Ala Ile Phe Gln Tyr Thr Met Arg Gln Val Leu Glu Pro Phe Arg Lys
    770                 775                 780

Ala Asn Pro Asp Val Ile Leu Ile Gln Tyr Met Asp Asp Ile Leu Ile
785                 790                 795                 800

Ala Ser Asp Arg Thr Gly Leu Glu His Asp Lys Val Val Leu Gln Leu
                805                 810                 815

Lys Glu Leu Leu Asn Gly Leu Gly Phe Ser Thr Pro Asp Glu Lys Phe
            820                 825                 830

Gln Lys Asp Pro Pro Phe Gln Trp Met Gly Cys Glu Leu Trp Pro Thr
        835                 840                 845

Lys Trp Lys Leu Gln Lys Leu Gln Leu Pro Gln Lys Asp Ile Trp Thr
    850                 855                 860

Val Asn Asp Ile Gln Lys Leu Val Gly Val Leu Asn Trp Ala Ala Gln
865                 870                 875                 880

Ile Tyr Ser Gly Ile Lys Thr Lys His Leu Cys Arg Leu Ile Arg Gly
                885                 890                 895

Lys Met Thr Leu Thr Glu Glu Val Gln Trp Thr Glu Leu Ala Glu Ala
            900                 905                 910
```

```
Glu Leu Glu Glu Asn Lys Ile Ile Leu Ser Gln Glu Gln Glu Gly Tyr
        915                 920                 925
Tyr Tyr Gln Glu Glu Lys Glu Leu Glu Ala Thr Ile Gln Lys Ser Gln
        930                 935                 940
Gly His Gln Trp Thr Tyr Lys Ile His Gln Glu Glu Lys Ile Leu Lys
945                 950                 955                 960
Val Gly Lys Tyr Ala Lys Ile Lys Asn Thr His Thr Asn Gly Val Arg
            965                 970                 975
Leu Leu Ala Gln Val Val Gln Lys Ile Gly Lys Glu Ala Leu Val Ile
                980                 985                 990
Trp Gly Arg Ile Pro Lys Phe His Leu Pro Val Glu Arg Glu Thr Trp
            995                 1000                1005
Glu Gln Trp Trp Asp Asn Tyr Trp Gln Val Thr Trp Ile Pro Glu
    1010                1015                1020
Trp Asp Phe Val Ser Thr Pro Pro Leu Val Arg Leu Thr Phe Asn
    1025                1030                1035
Leu Val Gly Asp Pro Ile Pro Gly Ala Glu Thr Phe Tyr Thr Asp
    1040                1045                1050
Gly Ser Cys Asn Arg Gln Ser Lys Glu Gly Lys Ala Gly Tyr Val
    1055                1060                1065
Thr Asp Arg Gly Lys Asp Lys Val Lys Val Leu Glu Gln Thr Thr
    1070                1075                1080
Asn Gln Gln Ala Glu Leu Glu Val Phe Arg Met Ala Leu Ala Asp
    1085                1090                1095
Ser Gly Pro Lys Val Asn Ile Ile Val Asp Ser Gln Tyr Val Met
    1100                1105                1110
Gly Ile Val Ala Gly Gln Pro Thr Glu Ser Glu Asn Arg Ile Val
    1115                1120                1125
Asn Gln Ile Ile Glu Glu Met Ile Lys Lys Glu Ala Val Tyr Val
    1130                1135                1140
Ala Trp Val Pro Ala His Lys Gly Ile Gly Gly Asn Gln Glu Val
    1145                1150                1155
Asp His Leu Val Ser Gln Gly Ile Arg Gln Val Leu Phe Leu Glu
    1160                1165                1170
Lys Ile Glu Pro Ala Gln Glu Glu His Glu Lys Tyr His Ser Ile
    1175                1180                1185
Ile Lys Glu Leu Thr His Lys Phe Gly Ile Pro Leu Leu Val Ala
    1190                1195                1200
Arg Gln Ile Val Asn Ser Cys Ala Gln Cys Gln Gln Lys Gly Glu
    1205                1210                1215
Ala Ile His Gly Gln Val Asn Ala Glu Ile Gly Val Trp Gln Met
    1220                1225                1230
Asp Tyr Thr His Leu Glu Gly Lys Ile Ile Ile Val Ala Val His
    1235                1240                1245
Val Ala Ser Gly Phe Ile Glu Ala Glu Val Ile Pro Gln Glu Ser
    1250                1255                1260
Gly Arg Gln Thr Ala Leu Phe Leu Leu Lys Leu Ala Ser Arg Trp
    1265                1270                1275
Pro Ile Thr His Leu His Thr Asp Asn Gly Pro Asn Phe Thr Ser
    1280                1285                1290
Gln Glu Val Lys Met Val Ala Trp Trp Val Gly Ile Glu Gln Ser
    1295                1300                1305
Phe Gly Val Pro Tyr Asn Pro Gln Ser Gln Gly Val Val Glu Ala
```

```
                    1310                1315                1320

Met Asn His His Leu Lys Asn Gln Ile Ser Arg Ile Arg Glu Gln
    1325                1330                1335

Ala Asn Thr Ile Glu Thr Ile Val Leu Met Ala Val His Cys Met
    1340                1345                1350

Asn Phe Lys Arg Arg Gly Gly Ile Gly Asp Met Thr Pro Ala Glu
    1355                1360                1365

Arg Leu Ile Asn Met Ile Thr Thr Glu Gln Glu Ile Gln Phe Leu
    1370                1375                1380

Gln Arg Lys Asn Ser Asn Phe Lys Asn Phe Gln Val Tyr Tyr Arg
    1385                1390                1395

Glu Gly Arg Asp Gln Leu Trp Lys Gly Pro Gly Glu Leu Leu Trp
    1400                1405                1410

Lys Gly Glu Gly Ala Val Ile Val Lys Val Gly Thr Asp Ile Lys
    1415                1420                1425

Val Val Pro Arg Arg Lys Ala Lys Ile Ile Arg Asp Tyr Gly Gly
    1430                1435                1440

Arg Gln Glu Leu Asp Ser Ser Pro His Leu Glu Gly Ala Arg Glu
    1445                1450                1455

Asp Gly Glu Met Ala Cys Pro Cys Gln Val Pro Glu Ile Gln Asn
    1460                1465                1470

Lys Arg Pro Arg Gly Gly Ala Leu Cys Ser Pro Pro Gln Gly Gly
    1475                1480                1485

Met Gly Met Val Asp Leu Gln Gln Gly Asn Ile Pro Thr Thr Arg
    1490                1495                1500

Lys Lys Ser Ser Arg Asn Thr Gly Ile Leu Glu Pro Asn Thr Arg
    1505                1510                1515

Lys Arg Met Ala Leu Leu Ser Cys Ser Lys Ile Asn Leu Val Tyr
    1520                1525                1530

Arg Lys Val Leu Asp Arg Cys Tyr Pro Arg Leu Cys Arg His Pro
    1535                1540                1545

Asn Thr
    1550

<210> SEQ ID NO 35
<211> LENGTH: 521
<212> TYPE: PRT
<213> ORGANISM: Human immunodeficiency virus type 2

<400> SEQUENCE: 35

Met Gly Ala Arg Asn Ser Val Leu Arg Gly Lys Lys Ala Asp Glu
1                   5                   10                  15

Glu Lys Val Arg Leu Arg Pro Gly Gly Lys Lys Lys Tyr Arg Leu Lys
                    20                  25                  30

His Ile Val Trp Ala Ala Asn Glu Leu Asp Lys Phe Gly Leu Ala Glu
        35                  40                  45

Ser Leu Leu Glu Ser Lys Glu Gly Cys Gln Lys Ile Leu Arg Val Leu
    50                  55                  60

Asp Pro Leu Val Pro Thr Gly Ser Glu Asn Leu Lys Ser Leu Phe Asn
65                  70                  75                  80

Thr Val Cys Val Ile Trp Cys Leu His Ala Glu Glu Lys Val Lys Asp
                85                  90                  95

Thr Glu Glu Ala Lys Lys Leu Ala Gln Arg His Leu Val Ala Glu Thr
            100                 105                 110

Gly Thr Ala Glu Lys Met Pro Asn Thr Ser Arg Pro Thr Ala Pro Pro
```

```
                115             120              125
Ser Gly Lys Arg Gly Asn Tyr Pro Val Gln Gln Ala Gly Gly Asn Tyr
130                 135                 140

Val His Val Pro Leu Ser Pro Arg Thr Leu Asn Ala Trp Val Lys Leu
145                 150                 155                 160

Val Glu Glu Lys Lys Phe Gly Ala Glu Val Val Pro Gly Phe Gln Ala
                165                 170                 175

Leu Ser Glu Gly Cys Thr Pro Tyr Asp Ile Asn Gln Met Leu Asn Cys
                180                 185                 190

Val Gly Asp His Gln Ala Ala Met Gln Ile Ile Arg Glu Ile Ile Asn
                195                 200                 205

Glu Glu Ala Ala Asp Trp Asp Ser Gln His Pro Ile Pro Gly Pro Leu
210                 215                 220

Pro Ala Gly Gln Leu Arg Asp Pro Arg Gly Ser Asp Ile Ala Gly Thr
225                 230                 235                 240

Thr Ser Thr Val Asp Glu Gln Ile Gln Trp Met Tyr Arg Pro Gln Asn
                245                 250                 255

Pro Val Pro Val Gly Asn Ile Tyr Arg Arg Trp Ile Gln Ile Gly Leu
                260                 265                 270

Gln Lys Cys Val Arg Lys Tyr Asn Pro Thr Asn Ile Leu Asp Ile Lys
                275                 280                 285

Gln Gly Pro Lys Glu Pro Phe Gln Ser Tyr Val Asp Arg Phe Tyr Lys
                290                 295                 300

Ser Leu Arg Ala Glu Gln Thr Asp Pro Ala Val Lys Asn Trp Met Thr
305                 310                 315                 320

Gln Thr Leu Leu Ile Gln Asn Ala Asn Pro Asp Cys Lys Leu Val Leu
                325                 330                 335

Lys Gly Leu Gly Met Asn Pro Thr Leu Glu Glu Met Leu Thr Ala Cys
                340                 345                 350

Gln Gly Val Gly Gly Pro Gly Gln Lys Ala Arg Leu Met Ala Glu Ala
                355                 360                 365

Leu Lys Glu Ala Met Gly Pro Ser Pro Ile Pro Phe Ala Ala Ala Gln
370                 375                 380

Gln Arg Lys Ala Ile Arg Tyr Trp Asn Cys Gly Lys Glu Gly His Ser
385                 390                 395                 400

Ala Arg Gln Cys Arg Ala Pro Arg Arg Gln Gly Cys Trp Lys Cys Gly
                405                 410                 415

Lys Pro Gly His Ile Met Ala Asn Cys Pro Glu Arg Gln Ala Gly Phe
                420                 425                 430

Leu Gly Leu Gly Pro Arg Gly Lys Lys Pro Arg Asn Phe Pro Val Thr
                435                 440                 445

Gln Ala Pro Gln Gly Leu Ile Pro Thr Ala Pro Pro Ala Asp Pro Ala
450                 455                 460

Ala Glu Leu Leu Glu Arg Tyr Met Gln Gln Gly Arg Lys Gln Arg Glu
465                 470                 475                 480

Gln Arg Glu Arg Pro Tyr Lys Glu Val Thr Glu Asp Leu Leu His Leu
                485                 490                 495

Glu Gln Arg Glu Thr Pro His Arg Glu Glu Thr Glu Asp Leu Leu His
                500                 505                 510

Leu Asn Ser Leu Phe Gly Lys Asp Gln
                515                 520

<210> SEQ ID NO 36
<211> LENGTH: 15
```

```
<212> TYPE: PRT
<213> ORGANISM: Artificial sequence
<220> FEATURE:
<223> OTHER INFORMATION: A peptide sequence for site specific
      biotinylation
<220> FEATURE:
<221> NAME/KEY: misc_feature
<222> LOCATION: (9)..(9)
<223> OTHER INFORMATION: lysine residue undergoes biotinylation by the
      BirA biotin ligase enzyme

<400> SEQUENCE: 36

Leu His His Ile Leu Asp Ala Gln Lys Met Val Trp Asn His Arg
1               5                   10                  15

<210> SEQ ID NO 37
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 37
agcggataac aatttcacac agg                                           23

<210> SEQ ID NO 38
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 38
tttgtcgtct ttccagacgt tagt                                          24

<210> SEQ ID NO 39
<211> LENGTH: 8
<212> TYPE: PRT
<213> ORGANISM: Artificial sequence
<220> FEATURE:
<223> OTHER INFORMATION: HLA-A2-restricted Human immunodeficiency virus
      (HIV)-derived peptide (POL)

<400> SEQUENCE: 39

Ile Leu Glu Pro Val His Gly Val
1               5

<210> SEQ ID NO 40
<211> LENGTH: 9
<212> TYPE: PRT
<213> ORGANISM: Artificial sequence
<220> FEATURE:
<223> OTHER INFORMATION: HLA-A2-restricted hTERT (540) peptide

<400> SEQUENCE: 40

Ile Leu Ala Lys Phe Leu His Trp Leu
1               5

<210> SEQ ID NO 41
<211> LENGTH: 9
<212> TYPE: PRT
<213> ORGANISM: Artificial sequence
<220> FEATURE:
<223> OTHER INFORMATION: HLA-A2-restricted hTERT (865) peptide

<400> SEQUENCE: 41

Arg Leu Val Asp Asp Phe Leu Leu Val
1               5
```

```
<210> SEQ ID NO 42
<211> LENGTH: 9
<212> TYPE: PRT
<213> ORGANISM: Artificial sequence
<220> FEATURE:
<223> OTHER INFORMATION: HLA-A2-restricted gp100 derived peptide G9-209

<400> SEQUENCE: 42

Ile Thr Asp Gln Val Pro Phe Ser Val
1               5

<210> SEQ ID NO 43
<211> LENGTH: 10
<212> TYPE: PRT
<213> ORGANISM: Artificial sequence
<220> FEATURE:
<223> OTHER INFORMATION: HLA-A2-restricted XAGE peptide

<400> SEQUENCE: 43

Gly Val Phe Pro Ser Ala Pro Ser Pro Val
1               5                   10

<210> SEQ ID NO 44
<211> LENGTH: 9
<212> TYPE: PRT
<213> ORGANISM: Artificial sequence
<220> FEATURE:
<223> OTHER INFORMATION: HLA-A2-restricted TARP peptide

<400> SEQUENCE: 44

Phe Leu Arg Asn Phe Ser Leu Met Leu
1               5

<210> SEQ ID NO 45
<211> LENGTH: 9
<212> TYPE: PRT
<213> ORGANISM: Artificial sequence
<220> FEATURE:
<223> OTHER INFORMATION: HLA-A2-restricted CMV derived peptide

<400> SEQUENCE: 45

Asn Leu Val Pro Met Val Ala Thr Val
1               5

<210> SEQ ID NO 46
<211> LENGTH: 9
<212> TYPE: PRT
<213> ORGANISM: Artificial sequence
<220> FEATURE:
<223> OTHER INFORMATION: HLA-A2-restricted EBV derived peptide

<400> SEQUENCE: 46

Gly Leu Cys Thr Leu Val Ala Met Leu
1               5

<210> SEQ ID NO 47
<211> LENGTH: 9
<212> TYPE: PRT
<213> ORGANISM: Artificial sequence
<220> FEATURE:
<223> OTHER INFORMATION: HLA-A2-restricted Gp100 peptide (280V)

<400> SEQUENCE: 47

Tyr Leu Glu Pro Gly Pro Val Thr Val
1               5

<210> SEQ ID NO 48
```

```
<211> LENGTH: 717
<212> TYPE: DNA
<213> ORGANISM: Aequorea macrodactyla

<400> SEQUENCE: 48
atgagtaaag gagaagaact tttcactggg attgtcccag ttctcattga gttagacggt      60
gatgtccatg gacataaatt ctctgtcaga ggagaagggg aaggcgatgc agattatgga     120
aaacttgaaa tcaaattcat tgcactact ggaaagctac cagttccatg gccaacactt      180
gttactacac tgggctacgg catccaatgt ttcgcaagat acccagaaca catgaaaatg     240
aatgacttct tcaagagtgc catgcctgag ggttacattc aagaaagaac catcttttc      300
caagatgatg gaaaatacaa gacacgtggt gaagtcaagt ttgaaggtga tactcttgtt     360
aacagaattg agctcaaagg tatggacttt aaagaagatg caatatcct tggacacaag     420
ttggagtaca atttttaattc acataatgta tacattatgc cggacaaagc caataatgga     480
ctcaaagtca atttcaaaat tagacacaat atcgaaggtg tggtgtcca acttgctgat      540
cattaccaaa caaatgttcc ccttggagac ggtcctgtcc ttataccaat caatcactac     600
ctatccttgc aaacagccat ttcaaaagat cgaaatgaga cgagagatca tatggtgttt     660
ctggaattt tctcagcttg tggacataca catggcatgg atgaactata caaataa        717

<210> SEQ ID NO 49
<211> LENGTH: 10
<212> TYPE: PRT
<213> ORGANISM: Artificial sequence
<220> FEATURE:
<223> OTHER INFORMATION: HLA-A2-restricted MART peptide

<400> SEQUENCE: 49

Glu Leu Ala Gly Ile Gly Ile Leu Thr Val
1               5                   10

<210> SEQ ID NO 50
<211> LENGTH: 9
<212> TYPE: PRT
<213> ORGANISM: Artificial sequence
<220> FEATURE:
<223> OTHER INFORMATION: HLA-A2-restricted influenza MI 58-66 peptide

<400> SEQUENCE: 50

Gly Ile Leu Gly Phe Val Phe Thr Leu
1               5

<210> SEQ ID NO 51
<211> LENGTH: 9
<212> TYPE: PRT
<213> ORGANISM: Artificial sequence
<220> FEATURE:
<223> OTHER INFORMATION: HLA-A2-restricted HTLV-1(TAX) peptide

<400> SEQUENCE: 51

Leu Leu Phe Gly Tyr Pro Val Tyr Val
1               5

<210> SEQ ID NO 52
<211> LENGTH: 489
<212> TYPE: PRT
<213> ORGANISM: Artificial sequence
<220> FEATURE:
<223> OTHER INFORMATION: alkaline phosphatase

<400> SEQUENCE: 52

Met Lys Gln Ser Thr Ile Ala Leu Ala Leu Leu Pro Leu Leu Phe Thr
```

-continued

```
1               5                   10                  15
Pro Val Thr Lys Ala Arg Thr Pro Glu Met Pro Leu Gln Gly Thr Ala
                20                  25                  30

Val Asp Gly Gly Gly Ser Met His Ala Ser Leu Glu Val Leu Glu
        35                  40                  45

Asn Arg Ala Ala Gln Gly Asp Ile Thr Ala Pro Gly Gly Ala Arg Arg
        50                  55                  60

Leu Thr Gly Asp Gln Thr Ala Ala Leu Arg Asp Ser Leu Ser Asp Lys
65                  70                  75                  80

Pro Ala Lys Asn Ile Ile Leu Leu Ile Gly Asp Gly Met Gly Asp Ser
                85                  90                  95

Glu Ile Thr Ala Ala Arg Asn Tyr Ala Glu Gly Ala Gly Gly Phe Phe
                100                 105                 110

Lys Gly Ile Asp Ala Leu Pro Leu Thr Gly Gln Tyr Thr His Tyr Ala
                115                 120                 125

Leu Asn Lys Lys Thr Gly Lys Pro Asp Tyr Val Thr Asp Ser Ala Ala
        130                 135                 140

Ser Ala Thr Ala Trp Ser Thr Gly Val Lys Thr Tyr Asn Gly Ala Leu
145                 150                 155                 160

Gly Val Asp Ile His Glu Lys Asp His Pro Thr Ile Leu Glu Met Ala
                165                 170                 175

Lys Ala Ala Gly Leu Ala Thr Gly Asn Val Ser Thr Ala Glu Leu Gln
                180                 185                 190

Asp Ala Thr Pro Ala Ala Leu Val Ala His Val Thr Ser Arg Lys Cys
        195                 200                 205

Tyr Gly Pro Ser Ala Thr Ser Glu Lys Cys Pro Gly Asn Ala Leu Glu
210                 215                 220

Lys Gly Gly Lys Gly Ser Ile Thr Glu Gln Leu Leu Asn Ala Arg Ala
225                 230                 235                 240

Asp Val Thr Leu Gly Gly Gly Ala Lys Thr Phe Ala Glu Thr Ala Thr
                245                 250                 255

Ala Gly Glu Trp Gln Gly Lys Thr Leu Arg Glu Gln Ala Gln Ala Arg
                260                 265                 270

Gly Tyr Gln Leu Val Ser Asp Ala Ala Ser Leu Asn Ser Val Thr Glu
        275                 280                 285

Ala Asn Gln Gln Lys Pro Leu Leu Gly Leu Phe Ala Asp Gly Asn Met
        290                 295                 300

Pro Val Arg Trp Leu Gly Pro Lys Ala Thr Tyr His Gly Asn Ile Asp
305                 310                 315                 320

Lys Pro Ala Val Thr Cys Thr Pro Asn Pro Gln Arg Asn Asp Ser Val
                325                 330                 335

Pro Thr Leu Ala Gln Met Thr Asp Lys Ala Ile Glu Leu Leu Ser Lys
                340                 345                 350

Asn Glu Lys Gly Phe Phe Leu Gln Val Glu Gly Ala Ser Ile Asp Lys
        355                 360                 365

Gln Asp His Ala Ala Asn Pro Cys Gly Gln Ile Gly Glu Thr Val Asp
        370                 375                 380

Leu Asp Glu Ala Val Gln Arg Ala Leu Glu Phe Ala Lys Lys Glu Gly
385                 390                 395                 400

Asn Thr Leu Val Ile Val Thr Ala Asp His Ala His Ala Ser Gln Ile
                405                 410                 415

Val Ala Pro Asp Thr Lys Ala Pro Gly Leu Thr Gln Ala Leu Asn Thr
                420                 425                 430
```

```
Lys Asp Gly Ala Val Met Val Met Ser Tyr Gly Asn Ser Glu Glu Asp
            435                 440                 445

Ser Gln Glu His Thr Gly Ser Gln Leu Arg Ile Ala Ala Tyr Gly Pro
    450                 455                 460

His Ala Ala Asn Val Val Gly Leu Thr Asp Gln Thr Asp Leu Phe Tyr
465                 470                 475                 480

Thr Met Lys Ala Ala Leu Gly Leu Lys
                485

<210> SEQ ID NO 53
<211> LENGTH: 1470
<212> TYPE: DNA
<213> ORGANISM: Artificial sequence
<220> FEATURE:
<223> OTHER INFORMATION: alkaline phosphatase

<400> SEQUENCE: 53
ttatttcagc cccagagcgg ctttcatggt gtagaagaga tcggtctggt cggtcagtcc    60
aacaacattg gcggcatgcg ggccatacgc cgcaatacgc aactgactgc cggtatgttc   120
ttgtgaatcc tcttcggagt tcccgtaact catcaccatc actgcgccat ctttggtatt   180
tagcgcctgg gtgaggcccg gagctttggt atccggcgca acaatctggc tggcgtgggc   240
gtgatcagcg gtgactatga ccagcgtgtt accctccttt ttagcgaatt ccagcgcccg   300
ttgtacggct tcatcgagat cgaccgtctc gccaatttgc ccacaaggat cgcagcatg   360 atcctgttta tcgattgacg caccttcaac ttgcaggaaa aagcctttct cattttact   420 caacaattca atggctttgt cggtcatctg cgccagggtt ggtacactgt cattacgttg   480
cggatttggc gtacaggtga ctgcgggctt atcgatattg ccatggtacg ttgctttcgg   540
tcctagccag cgcactggca tattgccgtc agcaaacagg ccaagcaggg gttttgctg   600 attcgcttcc gtcaccgaat tcagtgaggc agcatcgctc accaactgat aaccacgcgc   660
ctgtgcctgt tcacgcagcg ttttcccctg ccattcacca gcggttgccg tttcagcaaa   720 ggttttgcg ccgccgccaa gcgtaacgtc ggcacgagcg ttaagcagct gttcggtaat   780
cgatcctttt ccgccttttt ccagagcgtt acccggacat tttcactgg tcgcgctcgg   840 accgtagcat ttgcgcgagg tcacatgtgc caccagcgca gcgggcgtgg catcctgcaa   900
ctctgcggta gaaacgttac cggtcgccag acctgcggct tttgccattt ccagaatcgt   960
tgggtgatct ttttcgtgaa tatcgacgcc cagcgcgccg ttataggttt tgacaccggt  1020
tgaccaggcg gttgctgatg cagccgagtc ggtgacgtag tccggtttgc cggttttttt  1080
attcagcgca tagtgagtgt attgcccggt aagcggtaag gcatctatac ctttaaaaaa  1140
gccgcccgca ccttcggcat aattacgtgc ggcagtaatt tccgagtccc catcccatc   1200 gccaatcagc aaaataatat ttttttgcagg tttatcgcta agagaatcac gcagagcggc  1260
agtctgatca cccgttaaac ggcgagcacc gccgggtgca gtaatatcgc cctgagcagc  1320
ccggttttcc agaacctcga ggctagcatg catagaaccg ccaccaccgt cgacagcgt  1380 accctgcaga ggcatttctg gtgtccgggc ttttgtcaca ggggtaaaca gtaacggtaa  1440
gagtgccagt gcaatagtgc tttgtttcac                                   1470

<210> SEQ ID NO 54
<211> LENGTH: 309
<212> TYPE: PRT
<213> ORGANISM: Artificial sequence
<220> FEATURE:
<223> OTHER INFORMATION: Horseradish peroxidase
```

<400> SEQUENCE: 54

```
Met Gln Leu Thr Pro Thr Phe Tyr Asp Asn Ser Cys Pro Asn Val Ser
1               5                   10                  15

Asn Ile Val Arg Asp Thr Ile Val Asn Glu Leu Arg Ser Asp Pro Arg
            20                  25                  30

Ile Ala Ala Ser Ile Leu Arg Leu His Phe His Asp Cys Phe Val Asn
        35                  40                  45

Gly Cys Asp Ala Ser Ile Leu Leu Asp Asn Thr Thr Ser Phe Arg Thr
    50                  55                  60

Glu Lys Asp Ala Phe Gly Asn Ala Asn Ser Ala Arg Gly Phe Pro Val
65                  70                  75                  80

Ile Asp Arg Met Lys Ala Ala Val Glu Ser Ala Cys Pro Arg Thr Val
                85                  90                  95

Ser Cys Ala Asp Leu Leu Thr Ile Ala Ala Gln Gln Ser Val Thr Leu
            100                 105                 110

Ala Gly Gly Pro Ser Trp Arg Val Pro Leu Gly Arg Arg Asp Ser Leu
        115                 120                 125

Gln Ala Phe Leu Asp Leu Ala Asn Ala Asn Leu Pro Ala Pro Phe Phe
130                 135                 140

Thr Leu Pro Gln Leu Lys Asp Ser Phe Arg Asn Val Gly Leu Asn Arg
145                 150                 155                 160

Ser Ser Asp Leu Val Ala Leu Ser Gly Gly His Thr Phe Gly Lys Asn
                165                 170                 175

Gln Cys Arg Phe Ile Met Asp Arg Leu Tyr Asn Phe Ser Asn Thr Gly
            180                 185                 190

Leu Pro Asp Pro Thr Leu Asn Thr Thr Tyr Leu Gln Thr Leu Arg Gly
        195                 200                 205

Leu Cys Pro Leu Asn Gly Asn Leu Ser Ala Leu Val Asp Phe Asp Leu
    210                 215                 220

Arg Thr Pro Thr Ile Phe Asp Asn Lys Tyr Tyr Val Asn Leu Glu Glu
225                 230                 235                 240

Gln Lys Gly Leu Ile Gln Ser Asp Gln Glu Leu Phe Ser Ser Pro Asn
                245                 250                 255

Ala Thr Asp Thr Ile Pro Leu Val Arg Ser Phe Ala Asn Ser Thr Gln
            260                 265                 270

Thr Phe Phe Asn Ala Phe Val Glu Ala Met Asp Arg Met Gly Asn Ile
        275                 280                 285

Thr Pro Leu Thr Gly Thr Gln Gly Gln Ile Arg Leu Asn Cys Arg Val
    290                 295                 300

Val Asn Ser Asn Ser
305
```

<210> SEQ ID NO 55
<211> LENGTH: 955
<212> TYPE: DNA
<213> ORGANISM: Artificial sequence
<220> FEATURE:
<223> OTHER INFORMATION: Horseradish peroxidase

<400> SEQUENCE: 55

```
aagcttaacc atgcagttaa cccctacatt ctacgacaat agctgtccca acgtgtccaa    60
catcgttcgc gacacaatcg tcaacgagct cagatccgat cccaggatcg ctgcttcaat   120
attacgtctg cacttccatg actgcttcgt gaatggttgc gacgctagca tattactgga   180
caacaccacc agtttccgca ctgaaaagga tgcattcggg aacgctaaca gcgccagggg   240
```

```
ctttccagtg atcgatcgca tgaaggctgc cgttgagtca gcatgcccac gaacagtcag    300
ttgtgcagac ctgctgacta tagctgcgca acagagcgtg actcttgcag gcggaccgtc    360
ctggagagtg ccgctcggtc gacgtgactc cctacaggca ttcctagatc tggccaacgc    420
caacttgcct gctccattct tcaccctgcc ccagctgaag gatagcttta gaaacgtggg    480
tctgaatcgc tcgagtgacc ttgtggctct gtccggagga cacacatttg gaaagaacca    540
gtgtaggttc atcatggata ggctctacaa tttcagcaac actgggttac ctgaccccac    600
gctgaacact acgtatctcc agacactgag aggcttgtgc ccactgaatg caacctcag     660 tgcactagtg gactttgatc tgcggacccc aaccatcttc gataacaagt actatgtgaa    720
tctagaggag cagaaaggcc tgatacagag tgatcaagaa ctgtttagca gtccaaacgc    780
cactgacacc atcccactgg tgagaagttt tgctaactct actcaaacct tctttaacgc    840
cttcgtggaa gccatggacc gtatgggtaa cattacccct ctgacgggta cccaaggcca    900
gattcgtctg aactgcagag tggtcaacag caactcttaa taaggatccg aattc         955
```

```
<210> SEQ ID NO 56
<211> LENGTH: 6
<212> TYPE: PRT
<213> ORGANISM: Artificial sequence
<220> FEATURE:
<223> OTHER INFORMATION: poly-histidine tag

<400> SEQUENCE: 56

His His His His His His
1               5

<210> SEQ ID NO 57
<211> LENGTH: 15
<212> TYPE: DNA
<213> ORGANISM: Artificial sequence
<220> FEATURE:
<223> OTHER INFORMATION: poly-histidine tag

<400> SEQUENCE: 57
catcatcatc accat                                                      15

<210> SEQ ID NO 58
<211> LENGTH: 11
<212> TYPE: PRT
<213> ORGANISM: Artificial sequence
<220> FEATURE:
<223> OTHER INFORMATION: c-myc tag

<400> SEQUENCE: 58

Glu Gln Lys Leu Ile Ser Glu Glu Asp Leu Asn
1               5                   10

<210> SEQ ID NO 59
<211> LENGTH: 33
<212> TYPE: DNA
<213> ORGANISM: Artificial sequence
<220> FEATURE:
<223> OTHER INFORMATION: c-myc tag

<400> SEQUENCE: 59
gaacaaaaac tcatctcaga agaggatctg aat                                  33

<210> SEQ ID NO 60
<211> LENGTH: 238
<212> TYPE: PRT
<213> ORGANISM: Artificial sequence
<220> FEATURE:
```

<223> OTHER INFORMATION: orange fluorescent protein

<400> SEQUENCE: 60

```
Met Ser Lys Gly Glu Glu Leu Phe Thr Gly Val Val Pro Ile Leu Val
1               5                   10                  15
Glu Leu Asp Gly Asp Val His Gly His Lys Phe Ser Val Arg Gly Glu
            20                  25                  30
Gly Glu Gly Asp Ala Asp Tyr Gly Lys Leu Glu Ile Lys Phe Ile Cys
        35                  40                  45
Thr Thr Gly Lys Leu Pro Val Pro Trp Pro Thr Leu Val Thr Thr Leu
    50                  55                  60
Gly Tyr Gly Ile Leu Cys Phe Ala Arg Tyr Pro Glu His Met Lys Met
65                  70                  75                  80
Asn Asp Phe Phe Lys Ser Ala Met Pro Glu Gly Tyr Ile Gln Glu Arg
                85                  90                  95
Thr Ile Phe Phe Gln Asp Asp Gly Lys Tyr Lys Thr Arg Gly Glu Val
            100                 105                 110
Lys Phe Glu Gly Asp Thr Leu Val Asn Arg Ile Glu Leu Lys Gly Met
        115                 120                 125
Asp Phe Lys Glu Asp Gly Asn Ile Leu Gly His Lys Leu Glu Tyr Asn
    130                 135                 140
Phe Asn Ser His Asn Val Tyr Ile Met Pro Asp Lys Ala Asn Asn Gly
145                 150                 155                 160
Leu Lys Val Asn Phe Lys Ile Arg His Asn Ile Glu Gly Gly Gly Val
                165                 170                 175
Gln Leu Ala Asp His Tyr Gln Thr Asn Val Pro Leu Gly Asp Gly Pro
            180                 185                 190
Val Leu Ile Pro Ile Asn His Tyr Leu Ser Tyr Gln Thr Ala Ile Ser
        195                 200                 205
Lys Asp Arg Asn Glu Thr Arg Asp His Met Val Phe Leu Glu Phe Phe
    210                 215                 220
Ser Ala Cys Gly His Thr His Gly Met Asp Glu Leu Tyr Lys
225                 230                 235
```

<210> SEQ ID NO 61
<211> LENGTH: 717
<212> TYPE: DNA
<213> ORGANISM: Artificial sequence
<220> FEATURE:
<223> OTHER INFORMATION: orange fluorescent protein

<400> SEQUENCE: 61

| | | |
|---|---|---|
| atgagtaaag gagaagaact tttcactgga gttgtcccaa ttcttgttga attagatggt | 60 |
| gatgtccatg gacataaatt ctctgtcaga ggagaagggg aaggcgatgc agattatgga | 120 |
| aaacttgaaa tcaaattcat ttgcactact ggaaagctac cagttccatg gccaacactt | 180 |
| gttactacac tgggctatgg catcctatgt ttcgcaagat acccagaaca catgaaaatg | 240 |
| aatgacttct tcaagagtgc catgcctgag ggttacattc aagaaagaac catctttttc | 300 |
| caagatgatg gaaaatacaa gacacgtggt gaagtcaagt tgaaggtga tactcttgtt | 360 |
| aacagaattg agctcaaagg tatggacttt aagaagatg gcaatatcct tggacacaag | 420 |
| ttggagtaca attttaactc acataatgta tacattatgc cggacaaagc caataatgga | 480 |
| ctcaaagtca atttcaaaat tagacacaat atcgaaggtg gtggtgtcca actcgctgat | 540 |
| cattaccaaa caaatgttcc ccttggagac ggtcctgtcc ttataccaat caatcactac | 600 |
| ctatcctatc aaacagccat ttcaaaagat cgaaatgaga cgagagatca tatggtgttt | 660 | ctggaatttt tctcagcttg tggacataca catggcatgg atgaactata caaataa 717

<210> SEQ ID NO 62
<211> LENGTH: 1019
<212> TYPE: PRT
<213> ORGANISM: Artificial sequence
<220> FEATURE:
<223> OTHER INFORMATION: Beta galactosidase

<400> SEQUENCE: 62

```
Met Ala Asp Pro Val Val Leu Gln Arg Arg Asp Trp Glu Asn Pro Gly
1               5                   10                  15

Val Thr Gln Leu Asn Arg Leu Ala Ala His Pro Pro Phe Ala Ser Trp
            20                  25                  30

Arg Asn Ser Glu Glu Ala Arg Thr Asp Arg Pro Ser Gln Gln Leu Arg
        35                  40                  45

Ser Leu Asn Gly Glu Trp Arg Phe Ala Trp Phe Pro Ala Pro Glu Ala
    50                  55                  60

Val Pro Glu Ser Trp Leu Glu Cys Asp Leu Pro Glu Ala Asp Thr Val
65                  70                  75                  80

Val Val Pro Ser Asn Trp Gln Met His Gly Tyr Asp Ala Pro Ile Tyr
                85                  90                  95

Thr Asn Val Thr Tyr Pro Ile Thr Val Asn Pro Pro Phe Val Pro Thr
            100                 105                 110

Glu Asn Pro Thr Gly Cys Tyr Ser Leu Thr Phe Asn Val Asp Glu Ser
        115                 120                 125

Trp Leu Gln Glu Gly Gln Thr Arg Ile Ile Phe Asp Gly Val Asn Ser
    130                 135                 140

Ala Phe His Leu Trp Cys Asn Gly Arg Trp Val Gly Tyr Gly Gln Asp
145                 150                 155                 160

Ser Arg Leu Pro Ser Glu Phe Asp Leu Ser Ala Phe Leu Arg Ala Gly
                165                 170                 175

Glu Asn Arg Leu Ala Val Met Val Leu Arg Trp Ser Asp Gly Ser Tyr
            180                 185                 190

Leu Glu Asp Gln Asp Met Trp Arg Met Ser Gly Ile Phe Arg Asp Val
        195                 200                 205

Ser Leu Leu His Lys Pro Thr Thr Gln Ile Ser Asp Phe His Val Ala
    210                 215                 220

Thr Arg Phe Asn Asp Asp Phe Ser Arg Ala Val Leu Glu Ala Glu Val
225                 230                 235                 240

Gln Met Cys Gly Glu Leu Arg Asp Tyr Leu Arg Val Thr Val Ser Leu
                245                 250                 255

Trp Gln Gly Glu Thr Gln Val Ala Ser Gly Thr Ala Pro Phe Gly Gly
            260                 265                 270

Glu Ile Ile Asp Glu Arg Gly Gly Tyr Ala Asp Arg Val Thr Leu Arg
        275                 280                 285

Leu Asn Val Glu Asn Pro Lys Leu Trp Ser Ala Glu Ile Pro Asn Leu
    290                 295                 300

Tyr Arg Ala Val Val Glu Leu His Thr Ala Asp Gly Thr Leu Ile Glu
305                 310                 315                 320

Ala Glu Ala Cys Asp Val Gly Phe Arg Glu Val Arg Ile Glu Asn Gly
                325                 330                 335

Leu Leu Leu Leu Asn Gly Lys Pro Leu Leu Ile Arg Gly Val Asn Arg
            340                 345                 350

His Glu His His Pro Leu His Gly Gln Val Met Asp Glu Gln Thr Met
```

-continued

```
                355                 360                 365
Val Gln Asp Ile Leu Leu Met Lys Gln Asn Asn Phe Asn Ala Val Arg
370                 375                 380
Cys Ser His Tyr Pro Asn His Pro Leu Trp Tyr Thr Leu Cys Asp Arg
385                 390                 395                 400
Tyr Gly Leu Tyr Val Val Asp Glu Ala Asn Ile Glu Thr His Gly Met
            405                 410                 415
Val Pro Met Asn Arg Leu Thr Asp Asp Pro Arg Trp Leu Pro Ala Met
            420                 425                 430
Ser Glu Arg Val Thr Arg Met Val Gln Arg Asp Arg Asn His Pro Ser
            435                 440                 445
Val Ile Ile Trp Ser Leu Gly Asn Glu Ser Gly His Gly Ala Asn His
450                 455                 460
Asp Ala Leu Tyr Arg Trp Ile Lys Ser Val Asp Pro Ser Arg Pro Val
465                 470                 475                 480
Gln Tyr Glu Gly Gly Gly Ala Asp Thr Thr Ala Thr Asp Ile Ile Cys
                485                 490                 495
Pro Met Tyr Ala Arg Val Asp Glu Asp Gln Pro Phe Pro Ala Val Pro
            500                 505                 510
Lys Trp Ser Ile Lys Lys Trp Leu Ser Leu Pro Gly Glu Thr Arg Pro
            515                 520                 525
Leu Ile Leu Cys Glu Tyr Ala His Ala Met Gly Asn Ser Leu Gly Gly
            530                 535                 540
Phe Ala Lys Tyr Trp Gln Ala Phe Arg Gln Tyr Pro Arg Leu Gln Gly
545                 550                 555                 560
Gly Phe Val Trp Asp Trp Val Asp Gln Ser Leu Ile Lys Tyr Asp Glu
                565                 570                 575
Asn Gly Asn Pro Trp Ser Ala Tyr Gly Gly Asp Phe Gly Asp Thr Pro
            580                 585                 590
Asn Asp Arg Gln Phe Cys Met Asn Gly Leu Val Phe Ala Asp Arg Thr
            595                 600                 605
Pro His Pro Ala Leu Thr Glu Ala Lys His Gln Gln Gln Phe Phe Gln
            610                 615                 620
Phe Arg Leu Ser Gly Gln Thr Ile Glu Val Thr Ser Glu Tyr Leu Phe
625                 630                 635                 640
Arg His Ser Asp Asn Glu Leu Leu His Trp Met Val Ala Leu Asp Gly
                645                 650                 655
Lys Pro Leu Ala Ser Gly Glu Val Pro Leu Asp Val Ala Pro Gln Gly
            660                 665                 670
Lys Gln Leu Ile Glu Leu Pro Glu Leu Pro Gln Pro Glu Ser Ala Gly
            675                 680                 685
Gln Leu Trp Leu Thr Val Arg Val Val Gln Pro Asn Ala Thr Ala Trp
            690                 695                 700
Ser Glu Ala Gly His Ile Ser Ala Trp Gln Gln Trp Arg Leu Ala Glu
705                 710                 715                 720
Asn Leu Ser Val Thr Leu Pro Ala Ala Ser His Ala Ile Pro His Leu
                725                 730                 735
Thr Thr Ser Glu Met Asp Phe Cys Ile Glu Leu Gly Asn Lys Arg Trp
            740                 745                 750
Gln Phe Asn Arg Gln Ser Gly Phe Leu Ser Gln Met Trp Ile Gly Asp
            755                 760                 765
Lys Lys Gln Leu Leu Thr Pro Leu Arg Asp Gln Phe Thr Arg Ala Pro
770                 775                 780
```

```
Leu Asp Asn Asp Ile Gly Val Ser Glu Ala Thr Arg Ile Asp Pro Asn
785                 790                 795                 800

Ala Trp Val Glu Arg Trp Lys Ala Ala Gly His Tyr Gln Ala Glu Ala
                805                 810                 815

Ala Leu Leu Gln Cys Thr Ala Asp Thr Leu Ala Asp Ala Val Leu Ile
            820                 825                 830

Thr Thr Ala His Ala Trp Gln His Gln Gly Lys Thr Leu Phe Ile Ser
        835                 840                 845

Arg Lys Thr Tyr Arg Ile Asp Gly Ser Gly Gln Met Ala Ile Thr Val
    850                 855                 860

Asp Val Glu Val Ala Ser Asp Thr Pro His Pro Ala Arg Ile Gly Leu
865                 870                 875                 880

Asn Cys Gln Leu Ala Gln Val Ala Glu Arg Val Asn Trp Leu Gly Leu
                885                 890                 895

Gly Pro Gln Glu Asn Tyr Pro Asp Arg Leu Thr Ala Ala Cys Phe Asp
            900                 905                 910

Arg Trp Asp Leu Pro Leu Ser Asp Met Tyr Thr Pro Tyr Val Phe Pro
        915                 920                 925

Ser Glu Asn Gly Leu Arg Cys Gly Thr Arg Glu Leu Asn Tyr Gly Pro
    930                 935                 940

His Gln Trp Arg Gly Asp Phe Gln Phe Asn Ile Ser Arg Tyr Ser Gln
945                 950                 955                 960

Gln Gln Leu Met Glu Thr Ser His Arg His Leu Leu His Ala Glu Glu
                965                 970                 975

Gly Thr Trp Leu Asn Ile Asp Gly Phe His Met Gly Ile Gly Gly Asp
            980                 985                 990

Asp Ser Trp Ser Pro Ser Val Ser Ala Asp Phe Gln Leu Ser Ala Gly
        995                 1000                1005

Arg Tyr His Tyr Gln Leu Val Trp Cys Gln Lys
    1010                1015

<210> SEQ ID NO 63
<211> LENGTH: 3060
<212> TYPE: DNA
<213> ORGANISM: Artificial sequence
<220> FEATURE:
<223> OTHER INFORMATION: Beta galactosidase

<400> SEQUENCE: 63
ttatttttga caccagacca actggtaatg gtagcgaccg gcgctcagct ggaaatccgc      60
cgatactgac gggctccagg agtcgtcgcc accaatcccc atatggaaac cgtcgatatt     120
cagccatgtg ccttcttccg cgtgcagcag atggcgatgg ctggtttcca tcagttgctg     180
ttgactgtag cggctgatgt tgaactggaa gtcgccgcgc cactggtgtg gccataatt      240 caattcgcgc gtcccgcagc gcagaccgtt tcgctcggg aagacgtacg gggtatacat     300
gtctgacaat ggcagatccc agcggtcaaa acaggcggca gtaaggcggt cgggatagtt     360
ttcttgcggc cctaatccga gccagtttac ccgctctgct acctgcgcca gctggcagtt     420
caggccaatc cgcgccggat gcggtgtatc gctcgccact tcaacatcaa cggtaatcgc     480
catttgacca ctaccatcaa tccggtaggt tttccggctg ataaataagg ttttcccctg     540
atgctgccac gcgtgagcgg tcgtaatcag caccgcatca gcagtgtat ctgccgtgca     600 ctgcaacaac gctgcttcgg cctggtaatg gcccgccgcc ttccagcgtt cgacccaggc     660
gttagggtca atgcgggtcg cttcacttac gccaatgtcg ttatccagcg gtgcacgggt     720
gaactgatcg cgcagcggcg tcagcagttg ttttttatcg ccaatccaca tctgtgaaag     780
```

```
aaagcctgac tggcggttaa attgccaacg cttattaccc agctcgatgc aaaaatccat    840
ttcgctggtg gtcagatgcg ggatggcgtg ggacgcggcg gggagcgtca cactgaggtt    900
ttccgccaga cgccactgct gccaggcgct gatgtgcccg gcttctgacc atgcggtcgc    960
gttcggttgc actacgcgta ctgtgagcca gagttgcccg gcgctctccg gctgcggtag   1020
ttcaggcagt tcaatcaact gtttaccttg tggagcgaca tccagaggca cttcaccgct   1080
tgccagcggc ttaccatcca gcgccaccat ccagtgcagg agctcgttat cgctatgacg   1140
gaacaggtat tcgctggtca cttcgatggt ttgcccggat aaacggaact ggaaaaactg   1200
ctgctggtgt tttgcttccg tcagcgctgg atgcggcgtg cggtcggcaa agaccagacc   1260
gttcatacag aactggcgat cgttcggcgt atcgccaaaa tcaccgccgt aagccgacca   1320
cgggttgccg ttttcatcat atttaatcag cgactgatcc acccagtccc agacgaagcc   1380
gccctgtaaa cggggatact gacgaaacgc ctgccagtat ttagcgaaac cgccaagact   1440
gttacccatc gcgtgggcgt attcgcaaag gatcagcggg cgcgtctctc caggtagcga   1500
aagccatttt ttgatggacc atttcggcac agccgggaag ggctggtctt catccacgcg   1560
cgcgtacatc gggcaaataa tatcggtggc cgtggtgtcg gctccgccgc cttcatactg   1620
caccgggcgg gaaggatcga cagatttgat ccagcgatac agcgcgtcgt gattagcgcc   1680
gtggcctgat tcattcccca gcgaccagat gatcacactc gggtgattac gatcgcgctg   1740
caccattcgc gttacgcgtt cgctcatcgc cggtagccag cgcggatcat cggtcagacg   1800
attcattggc accatgccgt gggtttcaat attggcttca tccaccacat acaggccgta   1860
gcggtcgcac agcgtgtacc acagcggatg gttcggataa tgcgaacagc gcacggcgtt   1920
aaagttgttc tgcttcatca gcaggatatc ctgcaccatc gtctgctcat ccatgacctg   1980
accatgcaga ggatgatgct cgtgacggtt aacgcctcga atcagcaacg gcttgccgtt   2040
cagcagcagc agaccatttt caatccgcac ctcgcggaaa ccgacatcgc aggcttctgc   2100
ttcaatcagc gtgccgtcgg cggtgtgcag ttcaaccacc gcacgataga gattcgggat   2160
ttcggcgctc cacagtttcg ggttttcgac gttcagacgt agtgtgacgc gatcggcata   2220
accaccacgc tcatcgataa tttcaccgcc gaaaggcgcg gtgccgctgg cgacctgcgt   2280
ttcaccctgc cataaagaaa ctgttacccg taggtagtca cgcaactcgc cgcacatctg   2340
aacttcagcc tccagtacag cgcggctgaa atcatcatta aagcgagtgg caacatggaa   2400
atcgctgatt tgtgtagtcg gtttatgcag caacgagacg tcacggaaaa tgccgctcat   2460
ccgccacata tcctgatctt ccagataact gccgtcactc caacgcagca ccatcaccgc   2520
gaggcggttt tctccggcgc gtaaaaatgc gctcaggtca aattcagacg gcaaacgact   2580
gtcctggccg taaccgaccc agcgcccgtt gcaccacaga tgaaacgccg agttaacgcc   2640
atcaaaaata attcgcgtct ggccttcctg tagccagctt tcatcaacat taaatgtgag   2700
cgagtaacaa cccgtcggat tctccgtggg aacaaacggc ggattgaccg taatgggata   2760
ggttacgttg gtgtagatgg gcgcatcgta accgtgcatc tgccagtttg aggggacgac   2820
gacagtatcg gcctcaggaa gatcgcactc cagccagctt ccggcaccg cttctggtgc    2880 cggaaaccag gcaaagcgcc attcgccatt caggctgcgc aactgttggg aagggcgatc   2940
ggtgcgggcc tcttcgctat tacgccagct ggcgaaaggg ggatgtgctg caaggcgatt   3000
aagttgggta acgccagggt tttcccagtc acgacgttgt aaaacgacgg gatcagccat   3060
```

<210> SEQ ID NO 64
<211> LENGTH: 159

```
<212> TYPE: PRT
<213> ORGANISM: Artificial sequence
<220> FEATURE:
<223> OTHER INFORMATION: streptavidin

<400> SEQUENCE: 64

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ser Ile Asp Ala Ala Lys
    130                 135                 140

Lys Ala Gly Val Asn Asn Gly Asn Pro Leu Asp Ala Val Gln Gln
145                 150                 155

<210> SEQ ID NO 65
<211> LENGTH: 483
<212> TYPE: DNA
<213> ORGANISM: Artificial sequence
<220> FEATURE:
<223> OTHER INFORMATION: streptavidin

<400> SEQUENCE: 65
gacccgagca aagattctaa agcacaagta tctgctgcag aagcaggaat tacaggcaca      60
tggtataatc agctgggatc tacatttatt gttacagccg gcgcagatgg agctcttaca    120
ggaacatatg aatctgctgt tggaaatgca gaatctagat acgtgcttac aggaagatat    180
gattctgcac ctgcaacaga tggatccgga acagcacttg gatggacagt tgcatggaaa    240
aacaattata gaaacgcaca tagcgctaca acatggtctg gccaatatgt gggaggtgca    300
gaagcaagaa ttaacacaca atggctttta acatctggaa caacagaagc aaatgcatgg    360
aaaagtactc ttgttggaca tgatacattt acaaaagtta aacctagcgc agcatctatc    420
gatgcagcga aaaagcagg agttaacaat ggcaatcctt tagatgcagt tcaacaataa    480
tga                                                                  483

<210> SEQ ID NO 66
<211> LENGTH: 216
<212> TYPE: PRT
<213> ORGANISM: Artificial sequence
<220> FEATURE:
<223> OTHER INFORMATION: Pseudomonas exotoxin A

<400> SEQUENCE: 66

Ala Glu Phe Leu Gly Asp Gly Gly Asp Val Ser Phe Ser Thr Arg Gly
1               5                   10                  15

Thr Gln Asn Trp Thr Val Glu Arg Leu Leu Gln Ala His Arg Gln Leu
            20                  25                  30
```

```
Glu Glu Arg Gly Tyr Val Phe Val Gly Tyr His Gly Thr Phe Leu Glu
        35                  40                  45

Ala Ala Gln Ser Ile Val Phe Gly Gly Val Arg Ala Arg Ser Gln Asp
    50                  55                  60

Leu Asp Ala Ile Trp Arg Gly Phe Tyr Ile Ala Gly Asp Pro Ala Leu
65                  70                  75                  80

Ala Tyr Gly Tyr Ala Gln Asp Gln Glu Pro Asp Ala Arg Gly Arg Ile
                85                  90                  95

Arg Asn Gly Ala Leu Leu Arg Val Tyr Val Pro Arg Ser Ser Leu Pro
            100                 105                 110

Gly Phe Tyr Arg Thr Gly Leu Thr Leu Ala Ala Pro Glu Ala Ala Gly
        115                 120                 125

Glu Val Glu Arg Leu Ile Gly His Pro Leu Pro Leu Arg Leu Asp Ala
    130                 135                 140

Ile Thr Gly Pro Glu Glu Glu Gly Gly Arg Leu Glu Thr Ile Leu Gly
145                 150                 155                 160

Trp Pro Leu Ala Glu Arg Thr Val Val Ile Pro Ser Ala Ile Pro Thr
                165                 170                 175

Asp Pro Arg Asn Val Gly Gly Asp Leu Ala Pro Ser Ser Ile Pro Asp
            180                 185                 190

Gln Glu Gln Ala Ile Ser Ala Leu Pro Asp Tyr Ala Ser Gln Pro Gly
        195                 200                 205

Lys Pro Ser Arg Glu Asp Leu Lys
    210                 215
```

<210> SEQ ID NO 67
<211> LENGTH: 651
<212> TYPE: DNA
<213> ORGANISM: Artificial sequence
<220> FEATURE:
<223> OTHER INFORMATION: Pseudomonas exotoxin A

<400> SEQUENCE: 67

```
gcggagttcc tcggcgacgg cggcgacgtc agcttcagca cccgcggcac gcagaactgg     60
acggtggagc ggctgctcca ggcgcaccgc caactggagg agcgcggcta tgtgttcgtc    120
ggctaccacg gcaccttcct cgaagcggcg caaagcatcg tcttcggcgg ggtgcgcgcg    180
cgcagccagg accttgacgc gatctggcgc ggtttctata tcgccggcga tccggcgctg    240
gcctacggct acgcccagga ccaggaaccc gacgcgcgcg gccggatccg caacggtgcc    300
ctgctgcggg tctatgtgcc gcgctcgagt ctgccgggct tctaccgcac cggcctgacc    360
ctggccgcgc cggaggcggc gggcgaggtc gaacggctga tcggccatcc gctgccgctg    420
cgcctggacg ccatcaccgg ccccgaggag gaaggcgggc gcctggagac cattctcggc    480
tggccgctgg ccgagcgcac cgtggtgatt ccctcggcga tccccaccga cccacgcaac    540
gtcggcggcg acctcgcccc gtccagcatc cccgaccagg aacaggcgat cagcgccctg    600
ccggactacg ccagccagcc cggcaaaccg tcgcgcgagg acctgaagta a             651
```

<210> SEQ ID NO 68
<211> LENGTH: 536
<212> TYPE: PRT
<213> ORGANISM: Artificial sequence
<220> FEATURE:
<223> OTHER INFORMATION: diphtheria toxin

<400> SEQUENCE: 68

```
Met Gly Ala Asp Asp Val Val Asp Ser Ser Lys Ser Phe Val Met Glu
```

-continued

```
          1               5              10              15
Asn Phe Ser Ser Tyr His Gly Thr Lys Pro Gly Tyr Val Asp Ser Ile
                    20                  25                  30

Gln Lys Gly Ile Gln Lys Pro Lys Ser Gly Thr Gln Gly Asn Tyr Asp
                    35                  40                  45

Asp Asp Trp Lys Gly Phe Tyr Ser Thr Asp Asn Lys Tyr Asp Ala Ala
 50                          55                  60

Gly Tyr Ser Val Asp Asn Glu Asn Pro Leu Ser Gly Lys Ala Gly Gly
 65                      70                  75                  80

Val Val Lys Val Thr Tyr Pro Gly Leu Thr Lys Val Leu Ala Leu Lys
                    85                  90                  95

Val Asp Asn Ala Glu Thr Ile Lys Lys Glu Leu Gly Leu Ser Leu Thr
                    100                 105                 110

Glu Pro Leu Met Glu Gln Val Gly Thr Glu Phe Ile Lys Arg Phe
                    115                 120                 125

Gly Asp Gly Ala Ser Arg Val Val Leu Ser Leu Pro Phe Ala Glu Gly
                    130                 135                 140

Ser Ser Ser Val Glu Tyr Ile Asn Asn Trp Glu Gln Ala Lys Ala Leu
145                     150                 155                 160

Ser Val Glu Leu Glu Ile Asn Phe Glu Thr Arg Gly Lys Arg Gly Gln
                    165                 170                 175

Asp Ala Met Tyr Glu Tyr Met Ala Gln Ala Cys Ala Gly Asn Arg Val
                    180                 185                 190

Arg Arg Ser Val Gly Ser Ser Leu Ser Cys Ile Asn Leu Asp Trp Asp
                    195                 200                 205

Val Ile Arg Asp Lys Thr Lys Thr Lys Ile Glu Ser Leu Lys Glu His
                    210                 215                 220

Gly Pro Ile Lys Asn Lys Met Ser Glu Ser Pro Asn Lys Thr Val Ser
225                     230                 235                 240

Glu Glu Lys Ala Lys Gln Tyr Leu Glu Glu Phe His Gln Thr Ala Leu
                    245                 250                 255

Glu His Pro Glu Leu Ser Glu Leu Lys Thr Val Thr Gly Thr Asn Pro
                    260                 265                 270

Val Phe Ala Gly Ala Asn Tyr Ala Ala Trp Ala Val Asn Val Ala Gln
                    275                 280                 285

Val Ile Asp Ser Glu Thr Ala Asp Asn Leu Glu Lys Thr Thr Ala Ala
                    290                 295                 300

Leu Ser Ile Leu Pro Gly Ile Gly Ser Val Met Gly Ile Ala Asp Gly
305                     310                 315                 320

Ala Val His His Asn Thr Glu Glu Ile Val Ala Gln Ser Ile Ala Leu
                    325                 330                 335

Ser Ser Leu Met Val Ala Gln Ala Ile Pro Leu Val Gly Glu Leu Val
                    340                 345                 350

Asp Ile Gly Phe Ala Ala Tyr Asn Phe Val Glu Ser Ile Ile Asn Leu
                    355                 360                 365

Phe Gln Val Val His Asn Ser Tyr Asn Arg Pro Ala Tyr Ser Pro Gly
                    370                 375                 380

His Lys Thr Gln Pro Phe Leu His Asp Gly Tyr Ala Val Ser Trp Asn
385                     390                 395                 400

Thr Val Glu Asp Ser Ile Ile Arg Thr Gly Phe Gln Gly Glu Ser Gly
                    405                 410                 415

His Asp Ile Lys Ile Thr Ala Glu Asn Thr Pro Leu Pro Ile Ala Gly
                    420                 425                 430
```

```
Val Leu Leu Pro Thr Ile Pro Gly Lys Leu Asp Val Asn Lys Ser Lys
        435                 440                 445

Thr His Ile Ser Val Asn Gly Arg Lys Ile Arg Met Arg Cys Arg Ala
        450                 455                 460

Ile Asp Gly Asp Val Thr Phe Cys Arg Pro Lys Ser Pro Val Tyr Val
465                 470                 475                 480

Gly Asn Gly Val His Ala Asn Leu His Val Ala Phe His Arg Ser Ser
                485                 490                 495

Ser Glu Lys Ile His Ser Asn Glu Ile Ser Ser Asp Ser Ile Gly Val
                500                 505                 510

Leu Gly Tyr Gln Lys Thr Val Asp His Thr Lys Val Asn Ser Lys Leu
        515                 520                 525

Ser Leu Phe Phe Glu Ile Lys Ser
        530                 535

<210> SEQ ID NO 69
<211> LENGTH: 1611
<212> TYPE: DNA
<213> ORGANISM: Artificial sequence
<220> FEATURE:
<223> OTHER INFORMATION: diphtheria toxin

<400> SEQUENCE: 69
atgggcgctg atgatgttgt tgattcttct aaatcttttg tgatggaaaa cttttcttcg      60
taccacggga ctaaacctgg ttatgtagat tccattcaaa aaggtataca aaagccaaaa     120
tctggtacac aaggaaatta tgacgatgat tggaaagggt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta gaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtgtcaggc gatcagtagg tagctcattg     600
tcatgcataa atcttgattg ggatgtcata agggataaaa ctaagacaaa gatagagtct     660
ttgaaagagc atggccctat caaaaataaa atgagcgaaa gtcccaataa aacagtatct     720
gaggaaaaag ctaaacaata cctagaagaa tttcatcaaa cggcattaga gcatcctgaa     780
ttgtcagaac ttaaaaccgt tactgggacc aatcctgtat tcgctggggc taactatgcg     840
gcgtgggcag taaacgttgc gcaagttatc gatagcgaaa cagctgataa tttggaaaag     900
acaactgctg ctcttttcga cttcctggt atcggtagcg taatgggcat tgcagacggt     960
gccgttcacc acaatacaga agagatagtg cacaatcaa tagctttatc atctttaatg    1020
gttgctcaag ctattccatt ggtaggagag ctagttgata ttggtttcgc tgcatataat    1080
tttgtagaga gtattatcaa tttatttcaa gtagttcata attcgtataa tcgtcccgcg    1140
tattctccgg ggcataaaac gcaaccattt cttcatgacg gtatgctgt cagttggaac    1200 actgttgaag attcgataat ccgaactggt tttcaagggg agagtgggca cgacataaaa    1260
attactgctg aaaataccc gcttccaatc gcgggtgtcc tactaccgac tattcctgga    1320
aagctggacg ttaataagtc caagactcat atttccgtaa atggtcggaa aataaggatg    1380
cgttgcagag ctagacggg tgatgtaact ttttgtcgcc ctaaatctcc tgtttatgtt    1440
ggtaatggtg tgcatgcgaa tcttcacgtg gcatttcaca gaagcagctc ggagaaaatt    1500
```

-continued

```
cattctaatg aaatttcatc ggattccata ggcgttcttg ggtaccagaa aacagtagat      1560
cacaccaagg ttaattctaa gctatcgcta tttttgaaa tcaaaagctg a                1611
```

<210> SEQ ID NO 70
<211> LENGTH: 127
<212> TYPE: PRT
<213> ORGANISM: Artificial sequence
<220> FEATURE:
<223> OTHER INFORMATION: interleukin 2 (IL-2)

<400> SEQUENCE: 70

```
Thr Lys Lys Thr Gln Leu Gln Leu Glu His Leu Leu Asp Leu Gln
1               5                   10                  15

Met Ile Leu Asn Gly Ile Asn Asn Tyr Lys Asn Pro Lys Leu Thr Arg
            20                  25                  30

Met Leu Thr Phe Lys Phe Tyr Met Pro Lys Lys Ala Thr Glu Leu Lys
        35                  40                  45

His Leu Gln Cys Leu Glu Glu Glu Leu Lys Pro Leu Glu Glu Val Leu
    50                  55                  60

Asn Leu Ala Gln Ser Lys Asn Phe His Leu Arg Pro Arg Asp Leu Ile
65                  70                  75                  80

Ser Asn Ile Asn Val Ile Val Leu Glu Leu Lys Gly Ser Glu Thr Thr
                85                  90                  95

Phe Met Cys Glu Tyr Ala Asp Glu Thr Ala Thr Ile Val Glu Phe Leu
            100                 105                 110

Asn Arg Trp Ile Thr Phe Cys Gln Ser Ile Ile Ser Thr Leu Thr
        115                 120                 125
```

<210> SEQ ID NO 71
<211> LENGTH: 698
<212> TYPE: DNA
<213> ORGANISM: Artificial sequence
<220> FEATURE:
<223> OTHER INFORMATION: interleukin 2 (IL-2)
<220> FEATURE:
<221> NAME/KEY: misc_feature
<222> LOCATION: (4)..(4)
<223> OTHER INFORMATION: n is a, c, g, or t

<400> SEQUENCE: 71

```
gggngggga caaagaaaac acagctacaa ctggagcatt tacttctgga tttacagatg       60
attttgaatg gaattaataa ttacaagaat cccaaactca ccaggatgct cacatttaag     120
ttttacatgc ccaagaaggc cacagaactg aaacatcttc agtgtctaga agaagaactc     180
aaacctctgg aggaagtgct aaatttagct caaagcaaaa actttcactt aagacccagg     240
gacttaatca gcaatatcaa cgtaatagtt ctggaactaa agggatctga acaacattc      300 atgtgtgaat atgctgatga cagcaacc attgtagaat ttctgaacag atggattacc       360
ttttgtcaaa gcatcatctc aacactgact tgataattaa gtgcttccca cttaaaacat     420
atcaggcctt ctatttattt aaatatttaa attttatatt tattgttgaa tgtatggttt     480
gctacctatt gtaactatta ttcttaatct taaaactata aatatggatc ttttatgatt     540 cttttttgtaa gccctagggg ctctaaaatg gtttcactta tttatcccaa aatatttatt    600
attatgttga atgttaaata tagtatctat gtagattggt tagtaaaact atttaataaa     660
tttgataaat ataaacaaaa aaaaaaaac ccccccc                                698
```

<210> SEQ ID NO 72
<211> LENGTH: 207

<212> TYPE: PRT
<213> ORGANISM: Artificial sequence
<220> FEATURE:
<223> OTHER INFORMATION: CD3

<400> SEQUENCE: 72

```
Met Gln Ser Gly Thr His Trp Arg Val Leu Gly Leu Cys Leu Leu Ser
1               5                   10                  15
Val Gly Val Trp Gly Gln Asp Gly Asn Glu Glu Met Gly Gly Ile Thr
            20                  25                  30
Gln Thr Pro Tyr Lys Val Ser Ile Ser Gly Thr Thr Val Ile Leu Thr
        35                  40                  45
Cys Pro Gln Tyr Pro Gly Ser Glu Ile Leu Trp Gln His Asn Asp Lys
    50                  55                  60
Asn Ile Gly Gly Asp Glu Asp Asp Lys Asn Ile Gly Ser Asp Glu Asp
65                  70                  75                  80
His Leu Ser Leu Lys Glu Phe Ser Glu Leu Glu Gln Ser Gly Tyr Tyr
                85                  90                  95
Val Cys Tyr Pro Arg Gly Ser Lys Pro Glu Asp Ala Asn Phe Tyr Leu
            100                 105                 110
Tyr Leu Arg Ala Arg Val Cys Glu Asn Cys Met Glu Met Asp Val Met
        115                 120                 125
Ser Val Ala Thr Ile Val Ile Val Asp Ile Cys Ile Thr Gly Gly Leu
    130                 135                 140
Leu Leu Leu Val Tyr Tyr Trp Ser Lys Asn Arg Lys Ala Lys Ala Lys
145                 150                 155                 160
Pro Val Thr Arg Gly Ala Gly Ala Gly Gly Arg Gln Arg Gly Gln Asn
                165                 170                 175
Lys Glu Arg Pro Pro Pro Val Pro Asn Pro Asp Tyr Glu Pro Ile Arg
            180                 185                 190
Lys Gly Gln Arg Asp Leu Tyr Ser Gly Leu Asn Gln Arg Arg Ile
        195                 200                 205
```

<210> SEQ ID NO 73
<211> LENGTH: 1311
<212> TYPE: DNA
<213> ORGANISM: Artificial sequence
<220> FEATURE:
<223> OTHER INFORMATION: CD3

<400> SEQUENCE: 73

| | | | | |
|---|---|---|---|---|
| gtaagtctgc tggcctccgc catcttagta aagtaacagt cccatgaaac aaagatgcag | 60 |
| tcgggcactc actggagagt tctgggcctc tgcctcttat cagttggcgt ttgggggcaa | 120 |
| gatggtaatg aagaaatggg tggtattaca cagacaccat ataaagtctc catctctgga | 180 |
| accacagtaa tattgacatg ccctcagtat cctggatctg aaatactatg gcaacacaat | 240 |
| gataaaaaca taggcggtga tgaggatgat aaaaacatag cagtgatga ggatcacctg | 300 |
| tcactgaagg aattttcaga attggagcaa agtggttatt atgtctgcta ccccagagga | 360 |
| agcaaaccag aagatgcgaa cttttatctc tacctgaggg caagagtgtg tgagaactgc | 420 |
| atggagatgg atgtgatgtc ggtggccaca attgtcatag tggacatctg catcactggg | 480 |
| ggcttgctgc tgctggttta ctactggagc aagaatagaa aggccaaggc caagcctgtg | 540 |
| acacgaggag cgggtgctgg cggcaggcaa aggggacaaa acaaggagag gccaccacct | 600 |
| gttcccaacc cagactatga gcccatccgg aaaggccagc gggacctgta ttctggcctg | 660 |
| aatcagagac gcatctgacc ctctggagaa cactgcctcc cgctggccca ggtctcctct | 720 |

```
ccagtccccc tgcgactccc tgtttcctgg gctagtcttg accccacga gagagaatcg    780 ttcctcagcc tcatggtgaa ctcgcgccct ccagcctgat ccccgctcc ctcctccctg    840 ccttctctgc tggtacccag tcctaaaata ttgctgcttc ctcttccttt gaagcatcat    900
cagtagtcac accctcacag ctggcctgcc ctcttgccag gatatttatt tgtgctattc    960
actcccttcc ctttggatgt aacttctccg ttcagttccc tccttttctt gcatgtaagt   1020
tgtcccccat cccaaagtat tccatctact tttctatcgc cgtcccctt tgcagccctc   1080 tctggggatg gactgggtaa atgttgacag aggccctgcc ccgttcacag atcctggccc   1140
tgagccagcc ctgtgctcct ccctccccca acactcccta ccaaccccct aatccctac    1200 tccctccaac ccccctccc actgtaggcc actggatggt catttggcat ctccgtatat   1260
gtgctctggc tcctcagctg agagagaaaa aaataaactg tatttggctg c            1311
```

<210> SEQ ID NO 74
<211> LENGTH: 290
<212> TYPE: PRT
<213> ORGANISM: Artificial sequence
<220> FEATURE:
<223> OTHER INFORMATION: CD16

<400> SEQUENCE: 74

Met Gly Gly Gly Ala Gly Glu Arg Leu Phe Thr Ser Ser Cys Leu Val
1               5                   10                  15

Gly Leu Val Pro Leu Gly Leu Arg Ile Ser Leu Val Thr Cys Pro Leu
            20                  25                  30

Gln Cys Gly Ile Met Trp Gln Leu Leu Pro Thr Ala Leu Leu Leu
        35                  40                  45

Leu Val Ser Ala Gly Met Arg Thr Glu Asp Leu Pro Lys Ala Val Val
50                  55                  60

Phe Leu Glu Pro Gln Trp Tyr Arg Val Leu Glu Lys Asp Ser Val Thr
65                  70                  75                  80

Leu Lys Cys Gln Gly Ala Tyr Ser Pro Glu Asp Asn Ser Thr Gln Trp
                85                  90                  95

Phe His Asn Glu Ser Leu Ile Ser Ser Gln Ala Ser Ser Tyr Phe Ile
            100                 105                 110

Asp Ala Ala Thr Val Asp Asp Ser Gly Glu Tyr Arg Cys Gln Thr Asn
        115                 120                 125

Leu Ser Thr Leu Ser Asp Pro Val Gln Leu Glu Val His Ile Gly Trp
130                 135                 140

Leu Leu Leu Gln Ala Pro Arg Trp Val Phe Lys Glu Glu Asp Pro Ile
145                 150                 155                 160

His Leu Arg Cys His Ser Trp Lys Asn Thr Ala Leu His Lys Val Thr
                165                 170                 175

Tyr Leu Gln Asn Gly Lys Gly Arg Lys Tyr Phe His His Asn Ser Asp
            180                 185                 190

Phe Tyr Ile Pro Lys Ala Thr Leu Lys Asp Ser Gly Ser Tyr Phe Cys
        195                 200                 205

Arg Gly Leu Phe Gly Ser Lys Asn Val Ser Ser Glu Thr Val Asn Ile
    210                 215                 220

Thr Ile Thr Gln Gly Leu Ala Val Ser Thr Ile Ser Ser Phe Phe Pro
225                 230                 235                 240

Pro Gly Tyr Gln Val Ser Phe Cys Leu Val Met Val Leu Leu Phe Ala
                245                 250                 255

Val Asp Thr Gly Leu Tyr Phe Ser Val Lys Thr Asn Ile Arg Ser Ser
            260                 265                 270

```
Thr Arg Asp Trp Lys Asp His Lys Phe Lys Trp Arg Lys Asp Pro Gln
    275                 280                 285
Asp Lys
    290

<210> SEQ ID NO 75
<211> LENGTH: 2406
<212> TYPE: DNA
<213> ORGANISM: Artificial sequence
<220> FEATURE:
<223> OTHER INFORMATION: CD16

<400> SEQUENCE: 75
gattctgtgt gtgtcctcag atgctcagcc acagaccttt gagggagtaa aggggggcaga      60 cccacccacc ttgcctccag gctctttcct tcctggtcct gttctatggt ggggctccct     120
tgccagactt cagactgaga agtcagatga agtttcaaga aaaggaaatt ggtgggtgac     180
agagatgggt ggaggggctg ggaaaaggct gtttacttcc tcctgtctag tcggtttggt     240 cccttttaggg ctccggatat ctttggtgac ttgtccactc cagtgtggca tcatgtggca     300
gctgctcctc ccaactgctc tgctacttct agtttcagct ggcatgcgga ctgaagatct     360
cccaaaggct gtggtgttcc tggagcctca atggtacagg gtgctcgaga aggacagtgt     420
gactctgaag tgccagggag cctactcccc tgaggacaat tccacacagt ggtttcacaa     480
tgagagcctc atctcaagcc aggcctcgag ctacttcatt gacgctgcca cagtcgacga     540
cagtggagag tacaggtgcc agacaaacct ctccacccct agtgacccgg tgcagctaga     600
agtccatatc ggctggctgt tgctccaggc ccctcggtgg gtgttcaagg aggaagaccc     660
tattcacctg aggtgtcaca gctgaagaa cactgctctg cataaggtca catatttaca     720
gaatggcaaa ggcaggaagt attttcatca taattctgac ttctacattc caaaagccac     780
actcaaagac agcggctcct acttctgcag ggggcttttt gggagtaaaa atgtgtcttc     840
agagactgtg aacatcacca tcactcaagg tttggcagtg tcaaccatct catcattctt     900
tccacctggg taccaagtct cttttctgctt ggtgatggta ctcctttttg cagtggacac     960
aggactatat ttctctgtga agacaaacat tcgaagctca acaagagact ggaaggacca    1020
taaatttaaa tggagaaagg accctcaaga caaatgaccc ccatcccatg ggggtaataa    1080
gagcagtagc agcagcatct ctgaacattt ctctggattt gcaaccccat catcctcagg    1140
cctctctaca agcagcagga aacatagaac tcagagccag atcccttatc caactctcga    1200
cttttccttg gtctccagtg aagggaaaa gcccatgatc ttcaagcagg gaagccccag    1260
tgagtagctg cattcctaga aattgaagtt tcagagctac acaaacactt tttctgtccc    1320
aaccgttccc tcacagcaaa gcaacaatac aggctaggga tggtaatcct ttaaacatac    1380
aaaaattgct cgtgttataa attacccagt ttagagggga aaaaaaaaca attattccta    1440
aataaatgga taagtagaat taatggttga ggcaggacca tacagagtgt gggaactgct    1500
ggggatctag ggaattcagt gggaccaatg aaagcatggc tgagaaatag caggtagtcc    1560
aggatagtct aagggaggtg ttcccatctg agcccagaga taagggtgtc ttcctagaac    1620
attagccgta gtggaattaa caggaaatca tgagggtgac gtagaattga gtcttccagg    1680
ggactctatc agaactggac catctccaag tatataacga tgagtcctct taatgctagg    1740
agtagaaaat ggtcctagga aggggactga ggattgcggt ggggggtggg gtggaaaaga    1800
aagtacagaa caaaccctgt gtcactgtcc caagttgcta agtgaacaga actatctcag    1860
catcagaatg agaaagcctg agaagaaaga accaaccaca agcacacagg aaggaaagcg    1920
```

```
caggaggtga aaatgctttc ttggccaggg tagtaagaat tagaggttaa tgcagggact    1980
gtaaaaccac cttttctgct tcaatatcta attcctgtgt agctttgttc attgcattta    2040
ttaaacaaat gttgtataac caatactaaa tgtactactg agcttcgctg agttaagtta    2100
tgaaactttc aaatccttca tcatgtcagt tccaatgagg tggggatgga gaagacaatt    2160
gttgcttatg aaagaaagct ttagctgtct ctgttttgta agctttaagc gcaacatttc    2220
ttggttccaa taaagcattt tacaagatct tgcatgctac tcttagatag aagatgggaa    2280
aaccatggta ataaaatatg aatgataaaa aaaaaaaaa aaaaaaaaaa aaaaaaaaaa    2340
aaaaaaaaaa aaaaaaaaaa aaaaaaaaaa aaaaaaaaaa aaaaaaaaaa aaaaaaaaaa    2400
aaaaaa                                                               2406

<210> SEQ ID NO 76
<211> LENGTH: 153
<212> TYPE: PRT
<213> ORGANISM: Artificial sequence
<220> FEATURE:
<223> OTHER INFORMATION: IL-4

<400> SEQUENCE: 76

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150

<210> SEQ ID NO 77
<211> LENGTH: 921
<212> TYPE: DNA
<213> ORGANISM: Artificial sequence
<220> FEATURE:
<223> OTHER INFORMATION: IL-4

<400> SEQUENCE: 77
ttctatgcaa agcaaaaagc cagcagcagc cccaagctga taagattaat ctaaagagca      60
aattatggtg taatttccta tgctgaaact ttgtagttaa ttttttaaaa aggtttcatt     120
ttcctattgg tctgatttca caggaacatt ttacctgttt gtgaggcatt ttttctcctg     180
gaagagaggt gctgattggc cccaagtgac tgacaatctg gtgtaacgaa atttccaat      240 gtaaactcat tttccctcgg tttcagcaat tttaaatcta tatatagaga tatctttgtc     300
agcattgcat cgttagcttc tcctgataaa ctaattgcct cacattgtca ctgcaaatcg     360
```

```
acacctatta atgggtctca cctcccaact gcttccccct ctgttcttcc tgctagcatg    420
tgccggcaac tttgtccacg gacacaagtg cgatatcacc ttacaggaga tcatcaaaac    480
tttgaacagc ctcacagagc agaagactct gtgcaccgag ttgaccgtaa cagacatctt    540
tgctgcctcc aagaacacaa ctgagaagga aaccttctgc agggctgcga ctgtgctccg    600
gcagttctac agccaccatg agaaggacac tcgctgcctg ggtgcgactg cacagcagtt    660
ccacaggcac aagcagctga tccgattcct gaaacggctc gacaggaacc tctggggcct    720
ggcgggcttg aattcctgtc ctgtgaagga agccaaccag agtacgttgg aaaacttctt    780
ggaaaggcta aagacgatca tgagagagaa atattcaaag tgttcgagct gaatatttta    840
atttatgagt ttttgatagc tttattttt aagtatttat atatttataa ctcatcataa    900
aataaagtat atatagaatc t                                              921
```

<210> SEQ ID NO 78
<211> LENGTH: 365
<212> TYPE: PRT
<213> ORGANISM: Artificial sequence
<220> FEATURE:
<223> OTHER INFORMATION: HLA class I histocompatibility antigen, A-2
      alpha chain

<400> SEQUENCE: 78

```
Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Val Gln Arg Met Tyr Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255
```

-continued

```
Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
        355                 360                 365

<210> SEQ ID NO 79
<211> LENGTH: 4000
<212> TYPE: DNA
<213> ORGANISM: Artificial sequence
<220> FEATURE:
<223> OTHER INFORMATION: HLA class I histocompatibility antigen, A-2
      alpha chain

<400> SEQUENCE: 79
aagcttactc tctggcacca aactccatgg gatgattttt ccttcctaga agagtccagg      60
tggacaggta aggagtggga gtcagggagt ccagttccag ggacagagat tacgggataa    120
aaagtgaaag gagagggacg gggcccatgc cgagggtttc tcccttgttt ctcagacagc    180
tcttgggcca agactcaggg agacattgag acagagcgct tggcacagaa gcagaggggt    240
cagggcgaag tccagggccc caggcgttgg ctctcagggt tcaggcccc gaaggcggtg     300 tatggattgg ggagtcccag ccttggggat tccccaactc cgcagtttct tttctcccttc   360 tcccaaccta tgtagggtcc ttcttcctgg atactcacga cgcggaccca gttctcactc    420
ccattgggtg tcgggtttcc agagaagcca atcagtgtcg tcgcggtcgc ggttctaaag    480
tccgcacgca cccaccggga ctcagattct ccccagacgc cgaggatggc cgtcatggcg    540
ccccgaaccc tcgtcctgct actctcgggg gctctggccc tgacccagac ctgggcgggt    600
gagtgcgggg tcgggaggga aacggcctct gtggggagaa gcaacgggcc gcctggcggg    660
ggcgcaggac ccgggaagcc gcgccgggag agggtcggg cgggtctcag ccactcctcg     720
tccccaggct ctcactccat gaggtatttc ttcacatccg tgtcccggcc cggccgcggg    780
gagccccgct tcatcgcagt gggctacgtg gacgacacgc agttcgtgcg gttcgacagc    840
gacgccgcga gccagaggat ggagccgcgg gcgccgtgga tagagcagga gggtccggag    900
tattgggacg gggagacacg gaaagtgaag gcccactcac agactcaccg agtggacctg    960
gggaccctgc gcggctacta caaccagagc gaggccggtg agtgacccccg cccggggcg  1020 caggtcacga cctctcatcc cccacggacg ggccaggtcg cccacagtct ccgggtccga   1080
gatccgcccc gaagccgcgg gaccccgaga cccttgcccc gggagaggcc caggcgcctt   1140
tacccggttt cattttcagt ttaggccaaa aatcccccca ggttggtcgg ggcggggcgg   1200
ggctcggggg accgggctga ccgcgggtc cgggccaggt tctcacaccg tccagaggat    1260
gtatggctgc gacgtggggt cggactggcg cttcctccgc gggtaccacc agtacgccta   1320
cgacggcaag gattacatcg ccctgaaaga ggacctgcgc tcttggaccg cggcggacat   1380
ggcagctcag accaccaagc acaagtggga ggcggcccat gtggcggagc agttgagagc   1440
```

```
ctacctggag ggcacgtgcg tggagtggct ccgcagatac ctggagaacg ggaaggagac    1500
gctgcagcgc acgggtacca ggggccacgg ggcgcctccc tgatcgcctg tagatctccc    1560
gggctggcct cccacaagga ggggagacaa ttgggaccaa cactagaata tcgccctccc    1620
tctggtcctg agggagagga atcctcctgg gtttccagat cctgtaccag agagtgactc    1680
tgaggttccg ccctgctctc tgacacaatt aagggataaa atctctgaag gaatgacggg    1740
aagacgatcc ctcgaatact gatgagtggt tcccttgac acacacaggc agcagccttg    1800
ggcccgtgac ttttcctctc aggccttgtt ctctgcttca cactcaatgt gtgtgggggt    1860
ctgagtccag cacttctgag tccttcagcc tccactcagg tcaggaccag aagtcgctgt    1920
tccctcttca gggactagaa tttccacgga ataggagatt atcccaggtg cctgtgtcca    1980
ggctggtgtc tgggttctgt gctcccttcc ccatcccagg tgtcctgtcc attctcaaga    2040
tagccacatg tgtgctggag gagtgtccca tgacagatcg aaaatgcctg aatgatctga    2100
ctcttcctga cagacgcccc caaaacgcat atgactcacc acgctgtctc tgaccatgaa    2160
gccaccctga ggtgctgggc cctgagcttc taccctgcgg agatcacact gacctggcag    2220
cgggatgggg aggaccagac ccaggacacg gagctcgtgg agaccaggcc tgcaggggat    2280
ggaaccttcc agaagtgggc ggctgtggtg gtgccttctg acaggagca gagatacacc    2340 tgccatgtgc agcatgaggg tttgcccaag cccctcaccc tgagatgggg taaggaggga    2400
gacgggggtg tcatgtcttt tagggaaagc aggagcctct ctgacccttta gcagggtcag    2460 ggcccctcac cttcccctct ttttcccagag ccgtcttccc agcccaccat ccccatcgtg    2520
ggcatcattg ctggcctggt tctctttgga gctgtgatca ctggagctgt ggtcgctgct    2580
gtgatgtgga ggaggaagag ctcaggtggg aagggggtga aggtgggtc tgagatttct    2640 tgtctcactg aggggttccaa gacccaggta gaagtgtgcc ctgcctcgtt actgggaagc    2700
accacccaca attatgggcc tacccagcct gggccctgtg tgccagcact tactcttttg    2760
taaagcacct gttaaaatga aggacagatt tatcaccttg attacagcgg tgatgggacc    2820
tgatcccagc agtcacaagt cacagggaa ggtccctgag gaccttcagg agggcggttg    2880
gtccaggacc cacacctgct ttcttcatgt ttcctgatcc cgccctgggt ctgcagtcac    2940
acatttctgg aaacttctct gaggtccaag acttggaggt tcctctagga ccttaaggcc    3000
ctgactcttt tctggtatct cacaggacat tttcttccca cagatagaaa aggagggagc    3060
tactctcagg ctgcaagtaa gtatgaagga ggctgatgcc tgaggtcctt gggatattgt    3120
gtttgggagc ccatggggga gctcacccac cccacaattc ctcctctagc cacatcttct    3180
gtgggatctg accaggttct gttttttgttc taccccaggc agtgacagtg cccagggctc    3240
tgatgtgtct ctcacagctt gtaaaggtga gagcctggag ggcctgatgt gtgttgggtg    3300
ttgggcggaa cagtggacac agctgtgcta tgggggtttct ttccattgga tgtattgagc    3360
atgcgatggg ctgtttaaag tgtgacccct cactgtgaca gatacgaatt tgttcatgaa    3420
tatttttttc tatagtgtga dacagctgcc ttgtgtggga ctgagaggca agagttgttc    3480
ctgcccttcc ctttgtgact tgaagaaccc tgactttgtt tctgcaaagg cacctgcatg    3540
tgtctgtgtt cgtgtaggca taatgtgagg aggtggggag accacccccac ccccatgtcc    3600 accatgaccc tcttcccacg ctgacctgtg ctccctcccc aatcatcttt cctgttccag    3660
agaggtgggg ctgaggtgtc tccatctctg tctcaacttc atggtgcact gagctgtaac    3720
ttcttccttc cctattaaaa ttagaacctg agtataaatt tactttctca aattcttgcc    3780
atgagaggtt gatgagttaa ttaaaggaga agattcctaa aatttgagag acaaaataaa    3840
```

-continued

```
tggaacacat gagaaccttc cagagtccac gtgttgctta tgctgatttg ttgcagggga    3900
ggagagtaga tggggctgtg cccagtttct gttccggcca ctatgggctt tatgtggtca    3960
ctgcttggct gggtcatctt tgctgctcca ttgtccttgg                          4000
```

<210> SEQ ID NO 80
<211> LENGTH: 178
<212> TYPE: PRT
<213> ORGANISM: Artificial sequence
<220> FEATURE:
<223> OTHER INFORMATION: Interleukin-10

<400> SEQUENCE: 80

```
Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```

<210> SEQ ID NO 81
<211> LENGTH: 1601
<212> TYPE: DNA
<213> ORGANISM: Artificial sequence
<220> FEATURE:
<223> OTHER INFORMATION: Interleukin-10

<400> SEQUENCE: 81

```
aaaccacaag acagacttgc aaaagaaggc atgcacagct cagcactgct ctgttgcctg     60
gtcctcctga ctggggtgag ggccagccca ggccagggca cccagtctga aacagctgc    120 acccacttcc caggcaacct gcctaacatg cttcgagatc tccgagatgc cttcagcaga    180
gtgaagactt tctttcaaat gaaggatcag ctggacaact tgttgttaaa ggagtccttg    240
ctggaggact taagggtta cctgggttgc caagccttgt ctgagatgat ccagttttac    300
ctggaggagg tgatgcccca agctgagaac caagacccag acatcaaggc gcatgtgaac    360
tccctggggg agaacctgaa gaccctcagg ctgaggctac ggcgctgtca tcgatttctt    420
ccctgtgaaa acaagagcaa ggccgtggag caggtgaaga atgcctttaa taagctccaa    480
gagaaaggca tctacaaagc catgagtgag tttgacatct tcatcaacta catagaagcc    540
tacatgacaa tgaagatacg aaactgagac atcagggtgg cgactctata gactctagga    600
```

-continued

```
cataaattag aggtctccaa aatcggatct ggggctctgg gatagctgac ccagcccctt    660
gagaaacctt attgtacctc tcttatagaa tatttattac ctctgatacc tcaacccccca   720 tttctattta tttactgagc ttctctgtga acgatttaga aagaagccca atattataat    780
ttttttcaat atttattatt ttcacctgtt tttaagctgt ttccataggg tgacacacta    840
tggtatttga gtgttttaag ataaattata agttacataa gggaggaaaa aaaatgttct    900
ttggggagcc aacagaagct tccattccaa gcctgaccac gctttctagc tgttgagctg    960
ttttccctga cctccctcta atttatcttg tctctgggct tggggcttcc taactgctac   1020
aaatactctt aggaagagaa accagggagc ccctttgatg attaattcac cttccagtgt   1080
ctcggaggga ttcccctaac ctcattcccc aaccacttca ttcttgaaag ctgtggccag   1140
cttgttattt ataacaacct aaatttggtt ctaggccggg cgcggtggct cacgcctgta   1200
atcccagcac tttgggaggc tgaggcgggt ggatcacttg aggtcaggag ttcctaacca   1260
gcctggtcaa catggtgaaa ccccgtctct actaaaaata caaaaattag ccgggcatgg   1320
tggcgcgcac ctgtaatccc agctacttgg gaggctgagg caagagaatt gcttgaaccc   1380
aggagatgga agttgcagtg agctgatatc atgcccctgt actccagcct gggtgacaga   1440
gcaagactct gtctcaaaaa aataaaaata aaaataaatt tggttctaat agaactcagt   1500
tttaactaga atttattcaa ttcctctggg aatgttacat tgtttgtctg tcttcatagc   1560
agattttaat tttgaataaa taaatgtatc ttattcacat c                       1601
```

<210> SEQ ID NO 82
<211> LENGTH: 576
<212> TYPE: PRT
<213> ORGANISM: Artificial sequence
<220> FEATURE:
<223> OTHER INFORMATION: Ricin

<400> SEQUENCE: 82

```
Met Lys Pro Gly Gly Asn Thr Ile Val Ile Trp Met Tyr Ala Val Ala
1               5                   10                  15

Thr Trp Leu Cys Phe Gly Ser Thr Ser Gly Trp Ser Phe Thr Leu Glu
            20                  25                  30

Asp Asn Asn Ile Phe Pro Lys Gln Tyr Pro Ile Ile Asn Phe Thr Thr
        35                  40                  45

Ala Gly Ala Thr Val Gln Ser Tyr Thr Asn Phe Ile Arg Ala Val Arg
    50                  55                  60

Gly Arg Leu Thr Thr Gly Ala Asp Val Arg His Glu Ile Pro Val Leu
65                  70                  75                  80

Pro Asn Arg Val Gly Leu Pro Ile Asn Gln Arg Phe Ile Leu Val Glu
                85                  90                  95

Leu Ser Asn His Ala Glu Leu Ser Val Thr Leu Ala Leu Asp Val Thr
            100                 105                 110

Asn Ala Tyr Val Val Gly Tyr Arg Ala Gly Asn Ser Ala Tyr Phe Phe
        115                 120                 125

His Pro Asp Asn Gln Glu Asp Ala Glu Ala Ile Thr His Leu Phe Thr
    130                 135                 140

Asp Val Gln Asn Arg Tyr Thr Phe Ala Phe Gly Gly Asn Tyr Asp Arg
145                 150                 155                 160

Leu Glu Gln Leu Ala Gly Asn Leu Arg Glu Asn Ile Glu Leu Gly Asn
                165                 170                 175

Gly Pro Leu Glu Glu Ala Ile Ser Ala Leu Tyr Tyr Tyr Ser Thr Gly
            180                 185                 190
```

Gly Thr Gln Leu Pro Thr Leu Ala Arg Ser Phe Ile Ile Cys Ile Gln
            195                 200                 205

Met Ile Ser Glu Ala Ala Arg Phe Gln Tyr Ile Glu Gly Glu Met Arg
    210                 215                 220

Thr Arg Ile Arg Tyr Asn Arg Arg Ser Ala Pro Asp Pro Ser Val Ile
225                 230                 235                 240

Thr Leu Glu Asn Ser Trp Gly Arg Leu Ser Thr Ala Ile Gln Glu Ser
                245                 250                 255

Asn Gln Gly Ala Phe Ala Ser Pro Ile Gln Leu Gln Arg Arg Asn Gly
            260                 265                 270

Ser Lys Phe Ser Val Tyr Asp Val Ser Ile Leu Ile Pro Ile Ile Ala
        275                 280                 285

Leu Met Val Tyr Arg Cys Ala Pro Pro Ser Ser Gln Phe Ser Leu
    290                 295                 300

Leu Ile Arg Pro Val Val Pro Asn Phe Asn Ala Asp Val Cys Met Asp
305                 310                 315                 320

Pro Glu Pro Ile Val Arg Ile Val Gly Arg Asn Gly Leu Cys Val Asp
                325                 330                 335

Val Arg Asp Gly Arg Phe His Asn Gly Asn Ala Ile Gln Leu Trp Pro
            340                 345                 350

Cys Lys Ser Asn Thr Asp Ala Asn Gln Leu Trp Thr Leu Lys Arg Asp
        355                 360                 365

Asn Thr Ile Arg Ser Asn Gly Lys Cys Leu Thr Thr Tyr Gly Tyr Ser
    370                 375                 380

Pro Gly Val Tyr Val Met Ile Tyr Asp Cys Asn Thr Ala Ala Thr Asp
385                 390                 395                 400

Ala Thr Arg Trp Gln Ile Trp Asp Asn Gly Thr Ile Ile Asn Pro Arg
                405                 410                 415

Ser Ser Leu Val Leu Ala Ala Thr Ser Gly Asn Ser Gly Thr Thr Leu
            420                 425                 430

Thr Val Gln Thr Asn Ile Tyr Ala Val Ser Gln Gly Trp Leu Pro Thr
        435                 440                 445

Asn Asn Thr Gln Pro Phe Val Thr Thr Ile Val Gly Leu Tyr Gly Leu
    450                 455                 460

Cys Leu Gln Ala Asn Ser Gly Gln Val Trp Ile Glu Asp Cys Ser Ser
465                 470                 475                 480

Glu Lys Ala Glu Gln Gln Trp Ala Leu Tyr Ala Asp Gly Ser Ile Arg
                485                 490                 495

Pro Gln Gln Asn Arg Asp Asn Cys Leu Thr Ser Asp Ser Asn Ile Arg
            500                 505                 510

Glu Thr Val Val Lys Ile Leu Ser Cys Gly Pro Ala Ser Ser Gly Gln
        515                 520                 525

Arg Trp Met Phe Lys Asn Asp Gly Thr Ile Leu Asn Leu Tyr Ser Gly
    530                 535                 540

Leu Val Leu Asp Val Arg Ala Ser Asp Pro Ser Leu Lys Gln Ile Ile
545                 550                 555                 560

Leu Tyr Pro Leu His Gly Asp Pro Asn Gln Ile Trp Leu Pro Leu Phe
                565                 570                 575

<210> SEQ ID NO 83
<211> LENGTH: 1887
<212> TYPE: DNA
<213> ORGANISM: Artificial sequence
<220> FEATURE:
<223> OTHER INFORMATION: Ricin

<400> SEQUENCE: 83

```
atgaaaccgg gaggaaatac tattgtaata tggatgtatg cagtggcaac atggctttgt      60
tttggatcca cctcagggtg gtctttcaca ttagaggata caacatatt ccccaaacaa     120
tacccaatta taaactttac cacagcgggt gccactgtgc aaagctacac aaactttatc    180
agagctgttc gcggtcgttt aacaactgga gctgatgtga acatgaaat accagtgttg     240
ccaaacagag ttggtttgcc tataaaccaa cggtttattt tagttgaact ctcaaatcat    300
gcagagcttt ctgttacatt agcgctggat gtcaccaatg catatgtggt cggctaccgt    360
gctggaaata gcgcatattt cttcatcct gacaatcagg aagatgcaga agcaatcact    420
catcttttca ctgatgttca aaatcgtat acattcgcct tggtggtaa ttatgataga     480
cttgaacaac ttgctggtaa tctgagagaa aatatcgagt gggaaatgg tccactagag    540
gaggctatct cagcgcttta ttattacagt actggtggca ctcagcttcc aactctggct    600
cgttccttta taatttgcat ccaaatgatt tcagaagcag caagattcca atatattgag    660
ggagaaatgc gcacgagaat taggtacaac cggagatctg caccagatcc tagcgtaatt    720
acacttgaga atagttgggg gagacttcc actgcaattc aagagtctaa ccaaggagcc    780
tttgctagtc caattcaact gcaaagacgt aatggttcca aattcagtgt gtacgatgtg    840
agtatattaa tccctatcat agctctcatg gtgtatagat gcgcacctcc accatcgtca    900
cagttttctt tgcttataag gccagtggta ccaaattta atgctgatgt ttgtatggat    960
cctgagccca tagtgcgtat cgtaggtcga atggtctat gtgttgatgt tagggatgga    1020
agattccaca acggaaacgc aatacagttg tggccatgca agtctaatac agatgcaaat   1080
cagctctgga ctttgaaaag agacaatact attcgatcta atggaaagtg tttaactact    1140
tacgggtaca gtccgggagt ctatgtgatg atctatgatt gcaatactgc tgcaactgat    1200
gccacccgct ggcaaatatg ggataatgga accatcataa atcccagatc tagtctagtt    1260
ttagcagcga catcagggaa cagtggtacc acacttacag tgcaaaccaa catttatgcc    1320
gttagtcaag gttggcttcc tactaataat acacaacctt ttgtgacaac cattgttggg   1380
ctatatggtc tgtgcttgca agcaaatagt ggacaagtat ggatagagga ctgtagcagt   1440
gaaaaggctg aacaacagtg ggctctttat gcagatggtt caatacgtcc tcagcaaaac   1500
cgagataatt gccttacaag tgattctaat atacgggaaa cagttgtcaa gatcctctct   1560
tgtggccctg catcctctgg ccaacgatgg atgttcaaga tgatggaac cattttaaat    1620
ttgtatagtg ggttggtgtt agatgtgagg gcatcggatc cgagccttaa acaaatcatt   1680
ctttacccctc tccatggtga cccaaaccaa atatggttac cattatttg atagacagat   1740
tactctcttg cagtgtgtat gtcctgccat gaaaatagat ggcttaaata aaaaggacat   1800
tgtaaatttt gtaactgaaa ggacagcaag ttattgcagt ccagtatcta ataagagcac    1860
aactattgtc ttgtgcattc taaattt                                       1887
```

<210> SEQ ID NO 84
<211> LENGTH: 353
<212> TYPE: PRT
<213> ORGANISM: Artificial sequence
<220> FEATURE:
<223> OTHER INFORMATION: PE38KDEL polypeptide

<400> SEQUENCE: 84

Ala Ala Ala Ser Gly Gly Pro Glu Gly Gly Ser Leu Ala Ala Leu Thr
1 5 10 15

-continued

| | | | | | | | | | | | |
|---|---|---|---|---|---|---|---|---|---|---|---|
|Ala|His|Gln|Ala|Cys|His|Leu|Pro|Leu|Glu|Thr|Phe|Thr|Arg|His|Arg|
| |  |20 | | | |25 | | | |30 | | | | | |

Ala His Gln Ala Cys His Leu Pro Leu Glu Thr Phe Thr Arg His Arg
                20              25              30

Gln Pro Arg Gly Trp Glu Gln Leu Glu Gln Cys Gly Tyr Pro Val Gln
        35              40              45

Arg Leu Val Ala Leu Tyr Leu Ala Ala Arg Leu Ser Trp Asn Gln Val
50              55              60

Asp Gln Val Ile Arg Asn Ala Leu Ala Ser Pro Gly Ser Gly Gly Asp
65              70              75              80

Leu Gly Glu Ala Ile Arg Glu Gln Pro Glu Gln Ala Arg Leu Ala Leu
                85              90              95

Thr Leu Ala Ala Ala Glu Ser Glu Arg Phe Val Arg Gln Gly Thr Gly
                100             105             110

Asn Asp Glu Ala Gly Ala Ala Asn Gly Pro Ala Asp Ser Gly Asp Ala
                115             120             125

Leu Leu Glu Arg Asn Tyr Pro Thr Gly Ala Glu Phe Leu Gly Asp Gly
130             135             140

Gly Asp Val Ser Phe Ser Thr Arg Gly Thr Gln Asn Trp Thr Val Glu
145             150             155             160

Arg Leu Leu Gln Ala His Arg Gln Leu Glu Glu Arg Gly Tyr Val Phe
                165             170             175

Val Gly Tyr His Gly Thr Phe Leu Glu Ala Ala Gln Ser Ile Val Phe
                180             185             190

Gly Gly Val Arg Ala Arg Ser Gln Asp Leu Asp Ala Ile Trp Arg Gly
                195             200             205

Phe Tyr Ile Ala Gly Asp Pro Ala Leu Ala Tyr Gly Tyr Ala Gln Asp
210             215             220

Gln Glu Pro Asp Ala Arg Gly Arg Ile Arg Asn Gly Ala Leu Leu Arg
225             230             235             240

Val Tyr Val Pro Arg Ser Ser Leu Pro Gly Phe Tyr Arg Thr Ser Leu
                245             250             255

Thr Leu Ala Ala Pro Glu Ala Ala Gly Glu Val Glu Arg Leu Ile Gly
                260             265             270

His Pro Leu Pro Leu Arg Leu Asp Ala Ile Thr Gly Pro Glu Glu Glu
                275             280             285

Gly Gly Arg Leu Glu Thr Ile Leu Gly Trp Pro Leu Ala Glu Arg Thr
290             295             300

Val Val Ile Pro Ser Ala Ile Pro Thr Asp Pro Arg Asn Val Gly Gly
305             310             315             320

Asp Leu Asp Pro Ser Ser Ile Pro Asp Lys Glu Gln Ala Ile Ser Ala
                325             330             335

Leu Pro Asp Tyr Ala Ser Gln Pro Gly Lys Pro Pro Arg Glu Asp Leu
                340             345             350

Lys

<210> SEQ ID NO 85
<211> LENGTH: 1059
<212> TYPE: DNA
<213> ORGANISM: Artificial sequence
<220> FEATURE:
<223> OTHER INFORMATION: PE38KDEL nucleotide sequence

<400> SEQUENCE: 85
gcggccgctt ccggaggtcc cgagggcggc agcctggccg cgctgaccgc gcaccaggct    60
tgccacctgc cgctggagac tttcacccgt catcgccagc cgcgcggctg gaacaactg    120 gagcagtgcg gctatccggt gcagcggctg gtcgccctct acctggcggc gcggctgtcg    180

```
tggaaccagg tcgaccaggt gatccgcaac gccctggcca gccccggcag cggcggcgac    240
ctgggcgaag cgatccgcga gcagccggag caggcccgtc tggccctgac cctggccgcc    300
gccgagagcg agcgcttcgt ccggcagggc accggcaacg acgaggccgg cgcggccaac    360
ggcccggcgg acagcggcga cgccctgctg gagcgcaact atcccactgg cgcggagttc    420
ctcggcgacg gcggcgacgt cagcttcagc acccgcggca cgcagaactg gacggtggag    480
cggctgctcc aggcgcaccg ccaactggag gagcgcggct atgtgttcgt cggctaccac    540
ggcaccttcc tcgaagcggc gcaaagcatc gtcttcggcg gggtgcgcgc gcgcagccag    600
gacctcgacg cgatctggcg cggttttctat atcgccggcg atccggcgct ggcctacggc    660
tacgcccagg accaggaacc cgacgcacgc ggccggatcc gcaacggtgc cctgctgcgg    720
gtctatgtgc cgcgctcgag cctgccgggc ttctaccgca ccagcctgac cctggccgcg    780
ccggaggcgg cgggcgaggt cgaacggctg atcggccatc cgctgccgct gcgcctggac    840
gccatcaccg gccccgagga ggaaggcggg cgcctggaga ccattctcgg ctggccgctg    900
gccgagcgca ccgtggtgat tccctcggcg atccccaccg acccgcgcaa cgtcggcggc    960
gacctcgacc cgtccagcat ccccgacaag gaacaggcga tcagcgccct gccggactac   1020
gccagccagc ccggcaaacc gccgcgcgag gacctgaag                          1059
```

US 8,747,855 B2

ANTI HUMAN IMMUNODEFICIENCY ANTIBODIES AND USES THEREOF

RELATED APPLICATIONS

This Application is a National Phase of PCT Patent Application No. PCT/IL2009/000379 having International filing date of Apr. 5, 2009, which claims the benefit of U.S. Provisional Patent Application No. 61/071,043 filed on Apr. 9, 2008. The contents of the above Applications are all incorporated herein by reference.

FIELD AND BACKGROUND OF THE INVENTION

The present invention, in some embodiments thereof, relates to antibodies which can specifically bind complexes of MHC and an MHC-restricted HIV antigenic peptide and uses thereof in the diagnosis and treatment of HIV/AIDS in a subject.

Acquired immune deficiency syndrome (AIDS), a disease that severely compromises the human immune system, is caused by the human immunodeficiency virus (HIV). Global statistics indicated that in 1998 as many as 33 million people worldwide were infected with the virus.

HIV testing, and especially early diagnosis of infection, is integral to HIV prevention, treatment and care efforts. Screening provides an opportunity for people to receive counseling and information about risk reduction. Early knowledge of HIV status, particularly for those who are serologically HIV positive, can link them to medical care and services that can reduce morbidity and mortality and improve their quality of life.

Detection of HIV antibodies in the blood continues to be the gold standard. However, due to the lag phase, which elapses between HIV exposure and initiation of HIV antibody response, early diagnosis of HIV infection is currently limited.

Therapeutic intervention for control of HIV infection include competitive inhibitors of apartyl protease such as, saquinavir, indinavir, ritonavir, nelfinavir and amprenavir; inhibitors of reverse transcriptase such as zidovudine, didanosine, stavudine, lamivudine, zalcitabine and abacavir; and non-nucleoside reverse transcriptase inhibitors, nevaripine, delavaridine and efavirenz, which inhibit the synthesis of viral cDNA via a non-competitive mechanism. However, although such drugs have been separately employed to reduce viral replication, the HIV virus rapidly evolves and develops resistance thereagainst.

Peptides derived from cytosolic-proteins which are mainly endogenously synthesized proteins are bound to class I major histocompatibility complex (MHC) molecules that are expressed on the surface of nearly all cells and are recognized by CD8+ cytotoxic T lymphocytes (CTLs)

The immune system is capable of mounting potent attacks on invading viruses and eliminating many of them. Those that persist have often evolved strategies to interfere with the pathway that presents viral peptide antigens bound to class I MHC molecules so that they can evade attack by CTL. Significance progress has been achieved, in recent years, in the understanding of cellular immune response against viral infected-cells and tumor cells. This is mainly due to the use of polyvalent, soluble peptide-HLA complexes that specifically bind the T-cell receptor (TCR), and enable the identification and characterization of antigen-specific T lymphocytes.

PCT Publication No. WO 03/068201 discloses antibodies having a T-cell receptor-like specificity, yet higher affinity, and the use of same in the detection and treatment of cancer, viral infection and autoimmune disease.

U.S. patent application Ser. Nos. 10/371,942 and 11/582,416 disclose MHC-peptide complex binding ligands.

PCT Publication No. WO 04/084798 discloses antigen-presenting complex-binding compositions and uses thereof.

SUMMARY OF THE INVENTION

According to an aspect of some embodiments of the present invention there is provided an isolated antibody comprising an antigen recognition domain capable of binding an MHC molecule being complexed with a human immunodeficiency virus (HIV) peptide derived from an HIV polypeptide selected from the group consisting of Pr55(Gag) (SEQ ID NO:1), envelope surface glycoprotein gp160 (SEQ ID NO:21), Vif (SEQ ID NO:22), Tat (SEQ ID NO:23), Rev (SEQ ID NO:24), Vpr (SEQ ID NO:25), Vpu (SEQ ID NO:26), Nef (SEQ ID NO:27), integrase (SEQ ID NO:30), Gag-Pol Transframe peptide (SEQ ID NO:31), Retropepsin (SEQ ID NO:32), gag-pol fusion polyprotein (HIV2) (SEQ ID NO:34) and gag polyprotein (HIV2) (SEQ ID NO:35), wherein the antibody does not bind the MHC molecule in an absence of the complexed peptide, and wherein the antibody does not bind the peptide in an absence of the MHC molecule.

According to an aspect of some embodiments of the present invention there is provided a molecule comprising the antibody of the invention conjugated to a therapeutic moiety.

According to an aspect of some embodiments of the present invention there is provided a molecule comprising the antibody of the invention conjugated to a detectable moiety.

According to an aspect of some embodiments of the present invention there is provided a multivalent composition comprising the isolated antibody of the invention or the molecule of the invention.

According to an aspect of some embodiments of the present invention there is provided an isolated polynucleotide comprising a nucleic acid sequence encoding the isolated antibody of the invention, or the molecule of the invention.

According to an aspect of some embodiments of the present invention there is provided a nucleic acid construct comprising the isolated polynucleotide of the invention and a promoter for directing expression of the nucleic acid sequence in a host cell.

According to an aspect of some embodiments of the present invention there is provided a pharmaceutical composition comprising as an active ingredient the isolated antibody of the invention, the molecule of the invention, the multivalent composition of the invention, the isolated polynucleotide of the invention and/or the nucleic acid construct of the invention.

According to an aspect of some embodiments of the present invention there is provided a method of detecting a cell expressing a human immunodeficiency virus (HIV) antigen, comprising contacting the cell with the isolated antibody of the invention, the molecule of the invention and/or the multivalent composition of the invention under conditions which allow immunocomplex formation, wherein a presence or a level above a predetermined threshold of the immunocomplex is indicative of HIV expression in the cell.

According to an aspect of some embodiments of the present invention there is provided a method of diagnosing a human immunodeficiency virus (HIV) infection in a subject in need thereof, comprising contacting a biological sample of the subject with the isolated antibody of the invention, the molecule of the invention and/or the multivalent composition of the invention under conditions which allow immunocomplex formation, wherein a presence or a level above a predetermined threshold of the immunocomplex in the biological sample is indicative of HIV-infected cells in the subject, thereby diagnosing the HIV infection in the subject.

According to an aspect of some embodiments of the present invention there is provided a method of treating acquired immune deficiency syndrome (AIDS), comprising administering to a subject in need thereof a therapeutically effective amount of the isolated antibody of the invention, the molecule of the invention, the multivalent composition of the invention, the isolated polynucleotide of the invention and/or the nucleic acid construct of the invention, thereby treating the AIDS.

According to an aspect of some embodiments of the present invention there is provided use of the isolated antibody of the invention, the molecule of the invention and/or the multivalent composition of the invention, for the manufacture of a medicament for treating AIDS.

According to an aspect of some embodiments of the present invention there is provided use of the isolated polynucleotide of the invention and/or the nucleic acid construct of the invention, for the manufacture of a medicament for treating AIDS.

According to some embodiments of the invention, the human immunodeficiency virus (HIV) peptide is set forth by SEQ ID NO:2.

According to some embodiments of the invention, the antigen recognition domain comprises complementarity determining region (CDR) amino acid sequences as set forth in SEQ ID NOs:3-8.

According to some embodiments of the invention, the isolated antibody of the invention, being multivalent.

According to some embodiments of the invention, the isolated antibody of the invention, being of an IgG class.

According to some embodiments of the invention, the nucleic acid sequence comprises SEQ ID NOs:9-14.

According to some embodiments of the invention, the isolated antibody, the molecule, the multivalent composition, the isolated polynucleotide and/or the nucleic acid construct is capable of killing HIV-infected cells in the subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
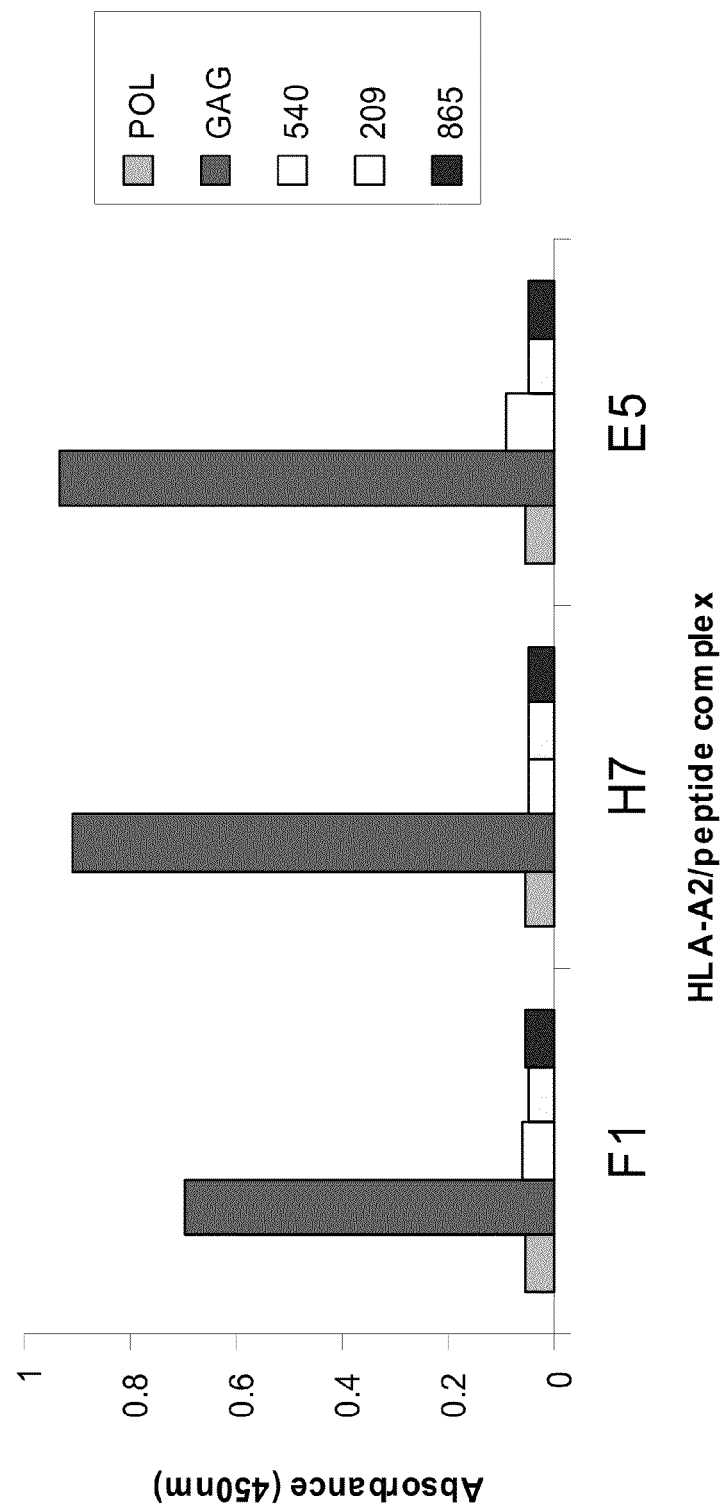
Figure 1B:
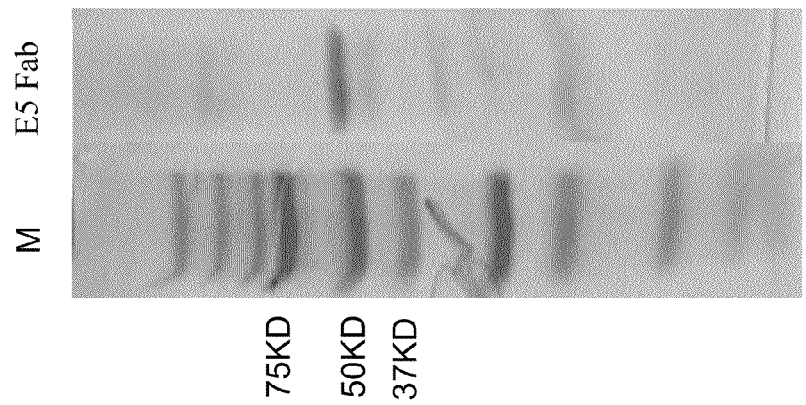

FIGS. 1A-B depict isolation of GAG/HLA-A2 specific TCR-like antibodies. FIG. 1A-A histogram depicting binding of Fab clones (measured by absorbance) to various MHC/peptide complexes. ScHLA-A2/peptide complexes were generated by in vitro refolding as described under Materials and Experimental Methods and the detection of bound antibodies was performed using peroxidase-labeled anti-human Fab. Note the specific reactivity of the F1, H7 and E5 Fab antibody clones with recombinant purified $GAG_{77\text{-}85}$/HLA-A2 as compared to the absence of binding to the control HLA-A2/peptide complexes [in which the control peptides were POL (SEQ ID NO:39), $hTERT_{540}$ (SEQ ID NO:40), $gp100_{209}$ (SEQ ID NO:42) and $hTERT_{865}$ (SEQ ID NO:41)]. FIG. 1B is an SDS-PAGE analysis of purified E5 Fab. Expression and purification of TCR-like E5 Fab clone capable of specifically binding the HLA-A2/$Gag_{77\text{-}85}$ peptide complex. Fab E5 clone was expressed in *E. coli* and purified by metal affinity chromatography as described.

Figure 2A:
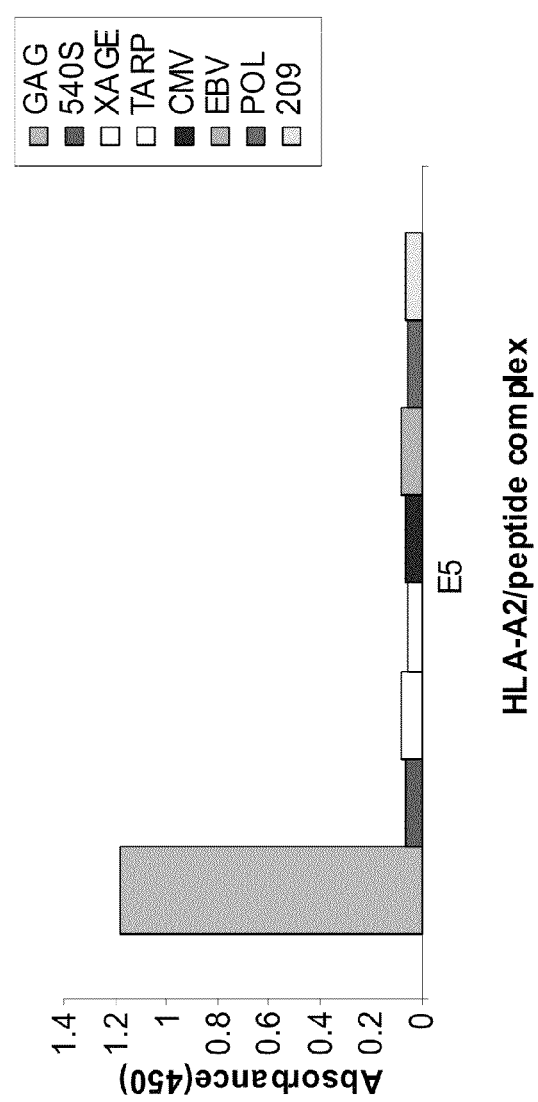
Figure 2B:
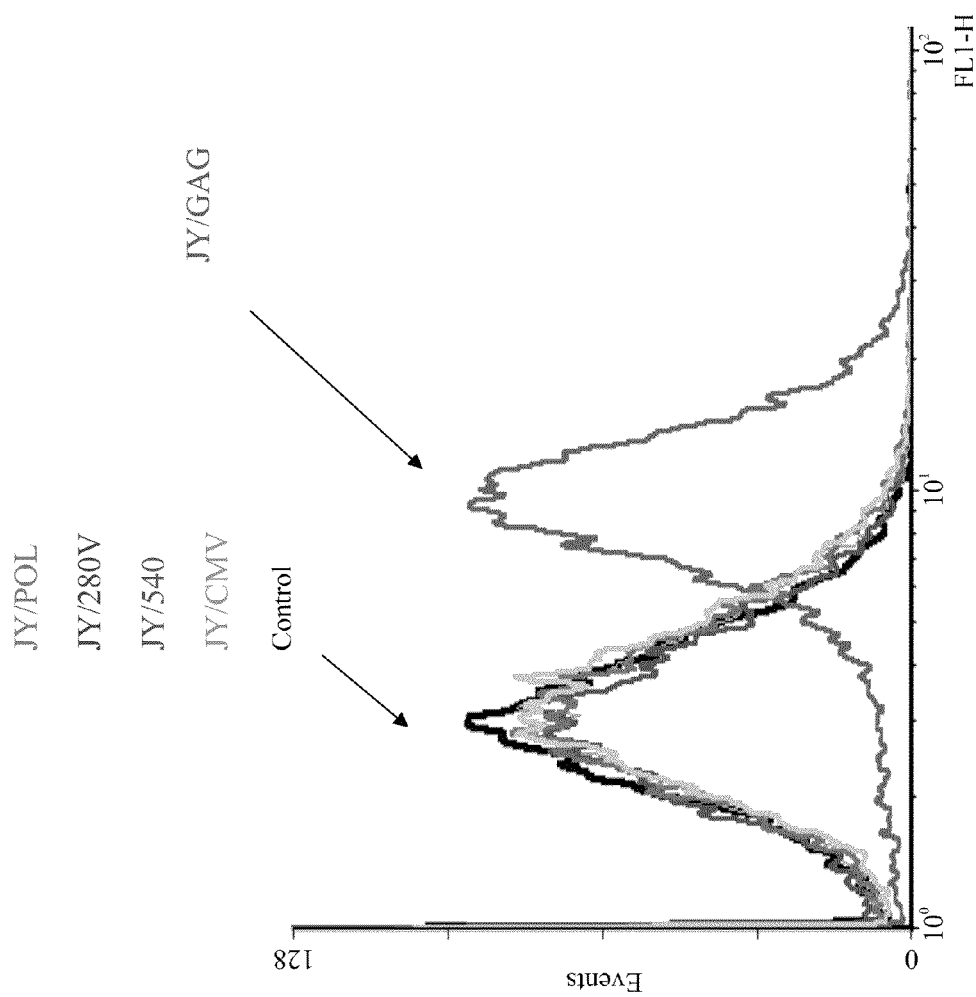

FIGS. 2A-B depict characterization of the reactivity of TCR-like E5 Fab to purified complexes (FIG. 2A) or complexes presented on cells (FIG. 2B). FIG. 2A—An ELISA of the E5 Fab to recombinant purified MHC/peptide complexes. Detection was with Peroxidase-labeled anti-human Fab. Note the binding of E5 Fab to the recombinant purified complex of HLA-A2/$GAG_{77\text{-}85}$ but not to other control recombinant purified complexes of HLA-A2 with Pol (HIV; SEQ ID NO:39), hTERT-540 (SEQ ID NO:41), XAGE (SEQ ID NO:43), TARP (SEQ ID NO:44), Cytomegalovirus (CMV; SEQ ID NO:45), EBV (SEQ ID NO:46), gp100-derived peptide G9-209 (SEQ ID NO:42) peptides. FIG. 2B—FACS analysis of the E5 Fab to peptide-loaded antigen presenting cells (APCs). JY EBV-transformed HLA-A2 positive B cells were loaded with the $Gag_{77\text{-}85}$ and control HLA-A2-restricted peptides [POL (SEQ ID NO:39), Gp100-280V (SEQ ID NO:47), HTERT-540 (SEQ ID NO:40) and CMV (SEQ ID NO:45)] and the reactivity with the purified E5 Fab (20 µg/ml) was detected. Data are representative of 6 experiments. Note that the E5 Fab binds only to cells loaded with the $Gag_{77\text{-}85}$ peptide but not to cells loaded with a control peptide.

Figure 3:
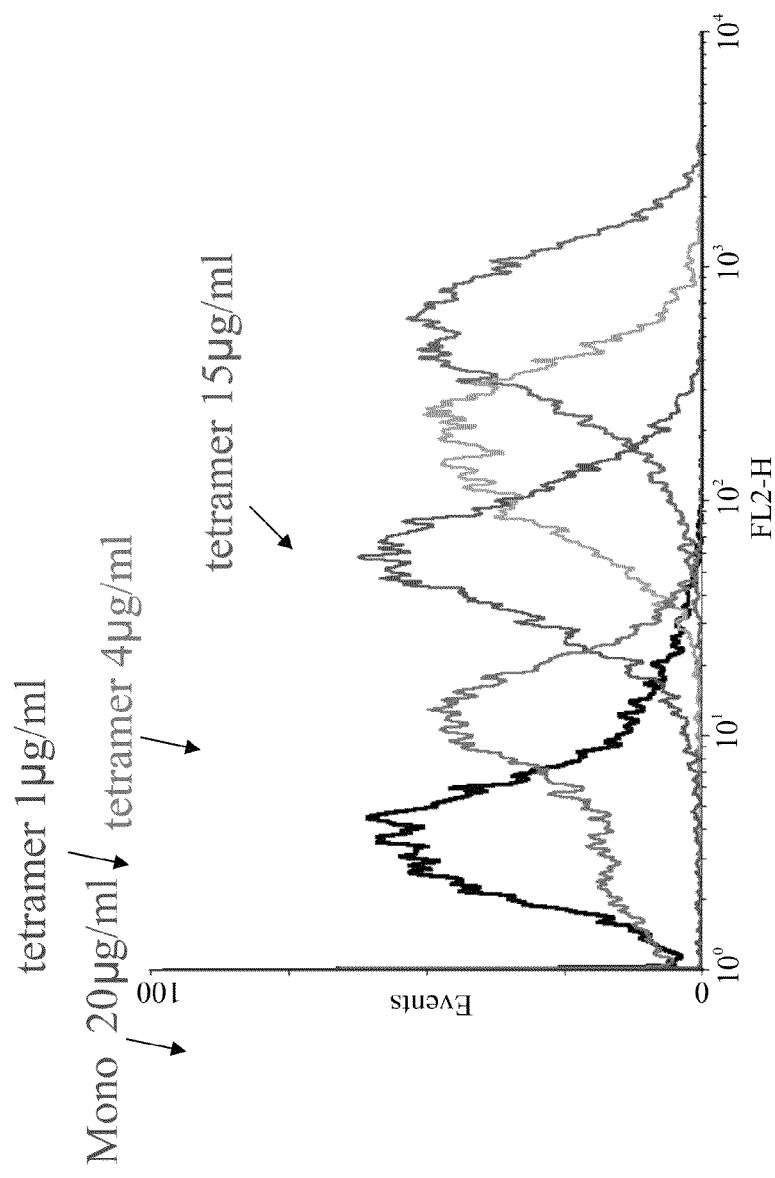

FIG. 3 depicts binding of the E5 Fab monomer or E5 Fab-tetramer to peptide-pulsed APCs. JY APCs were pulsed with $Gag_{77\text{-}85}$ and control peptides (as described in FIGS. 2A-B) and incubated with the HLA-A2/Gag specific, PE-labeled E5 Fab-tetramer [at concentrations of 1 µg/ml (blue line), 4 µg/ml (green line) or 15 µg/ml (red line)] or with the HLA-A2/Gag specific Fab monomer [20 µg/ml (purple line)]. Fab monomer binding was detected with PE-labeled anti-human Fab. Control unloaded cells were stained with the E5 Fab monomer and tetramer. Note the increased avidity of the Fab-tetramers as compared to that of the Fab-monomer.

Figure 4A:
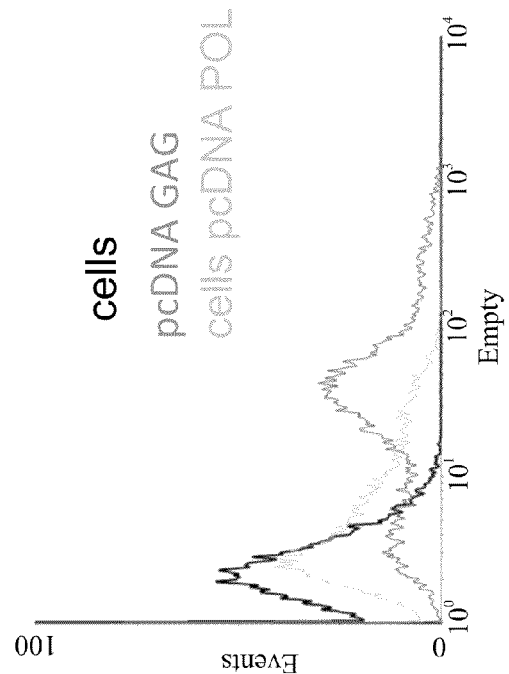
Figure 4B:
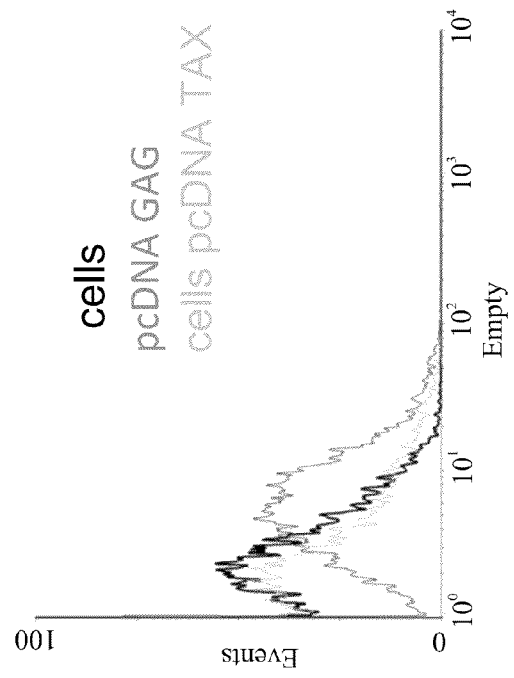
Figure 4C:
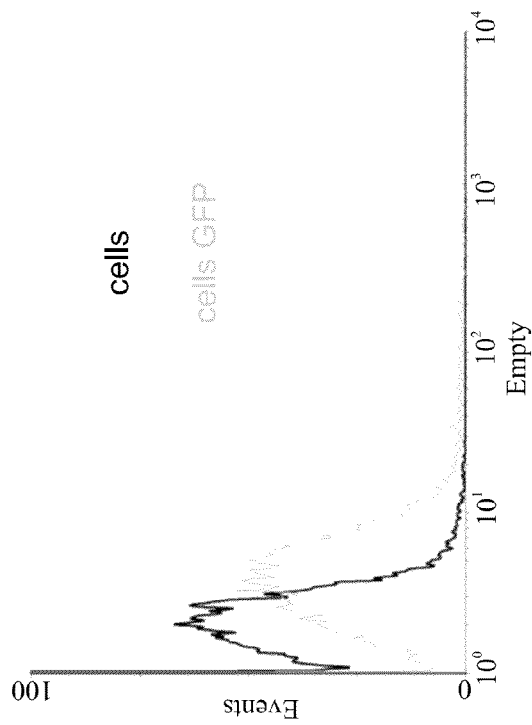

FIGS. 4A-C depict binding of E5 Fab to Gag/HLA-A2 complexes generated by active intracellular processing. JY HLA-A2$^+$ APCs were transfected with pCDNA containing the intact full length Gag gene [pVR1012X/S Gag/h (pVRC 3900); Yue Huang, et al., Journal of Virology, 2001, Vol. 75, p. 4947-4951], full length Human T cells lymphotropic virus type 1 (HTLV-1) TAX gene, or full length HIV Pol gene (pVR1012x/s Pol/h pVRC4100), or with an empty pCDNA control vector, and 24 hours after transfection the cells were stained by flow cytometry using the HLA-A2/Gag-specific E5 Fab tetramer (1 µg/ml). FIG. 4A—Flow cytometry analysis showing the binding of the E5 Fab-tetramer to cells expressing GAG but not to cells expressing TAX. FIG. 4B—Flow cytometry analysis showing the binding of the E5 Fab-tetramer to cells expressing GAG but not to cells expressing POL. FIG. 4C—Flow cytometry analysis depicting the efficiency of Gag gene transduction into JY cells as monitored by transfection of the pCDNA vector carrying the green fluorescent protein (GFP) gene.

Figure 5A:
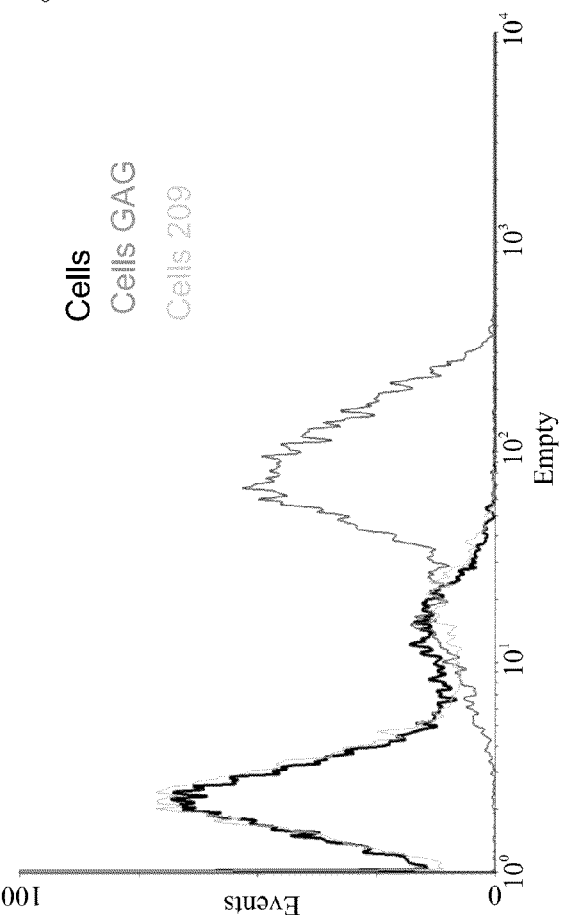
Figure 5B:
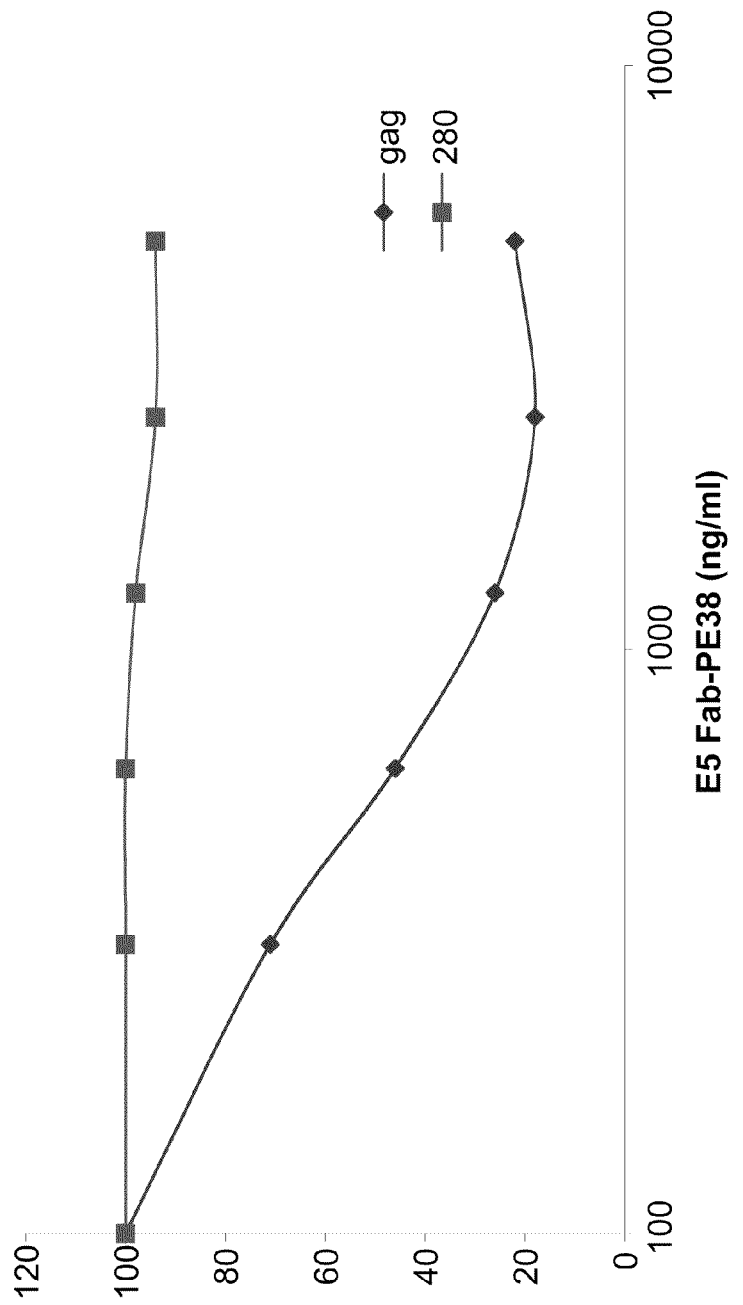

FIGS. 5A-B depict characterization of E5 Fab-PE38. FIG. 5A—Flow cytometry analysis depicting the binding of E5

Fab-PE38 fusion molecule to peptide-pulsed APCs. JY APCs were loaded with Gag$_{77-85}$ (SEQ ID NO:2) and control G9-209 (SEQ ID NO:42) peptides and the reactivity of the E5 Fab-PE38 fusion molecule was determined by using anti-PE38 antibodies. Detection was with FITC-anti rabbit IgG. FIG. 5B—Cytotoxic activity of E5 Fab-PE38 fusion on APCs. Gag positive and control tumor cells were incubated with increasing concentrations of E5 Fab-PE38. Protein synthesis was determined by incorporation of $^3$H-Leucine into cellular proteins. Note that while no change in protein synthesis is observed when the E5 Fab-PE38 is administered to APCs loaded with control peptides (e.g., G9-209), APCs loaded with the GAG$_{77-85}$ peptide undergo a significant reduction in protein synthesis, demonstrating the specific cytotoxicity of the E5 Fab to cells presenting the MHC/GAG$_{77-85}$ complex.

Figure 6A:
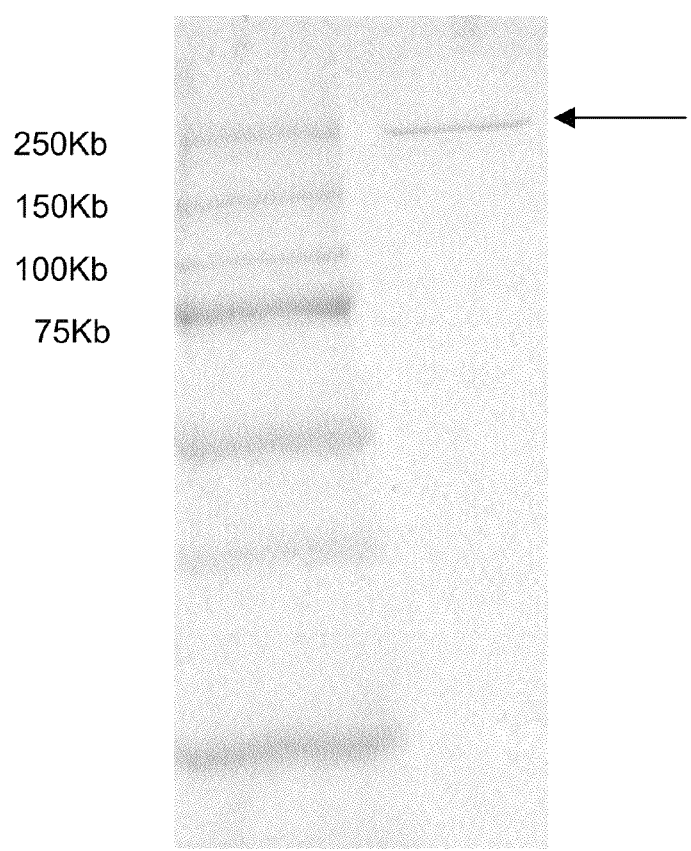

FIGS. 6A-B depict characterization of the reactivity of TCR-like E5 whole Ab. FIG. 6A—SDS-PAGE analysis of purified soluble E5 whole Ab. E5 whole antibody plasmids were co transfected to HEK293 and purified by protein A affinity chromatography as described. Left lane—protein marker; right lane—purified antibody. The results demonstrate the expression and purification of TCR-like E5 whole Ab (purified antibody, marked by the arrow). FIG. 6B—Flow cytometry analysis depicting binding of E5 whole Ab to peptide-loaded APCs. JY EBV-transformed HLA-A2 positive B cells were loaded with the Gag$_{77-85}$ and control HLA-A2-restricted peptides and the reactivity with purified E5 whole Ab (0.2 µg/ml) was measured. Control peptides were: MART (SEQ ID NO:49), EBV (SEQ ID NO:46), gp100-derived peptide G9-280V (SEQ ID NO:47), gp100-derived peptide G9-209 (SEQ ID NO:42), Cytomegalovirus (CMV)-derived peptide (SEQ ID NO:45), influenza MI$_{58-66}$ peptide (SEQ ID NO:50), POL (HIV) (SEQ ID NO:39) and HTLV-1(TAX) (SEQ ID NO:51). Another control was the use of the secondary antibody anti human Fab, labeled with FITC (aHF, black line).

FIGS. 7A-D depict comparative flow cytometric analysis. FIGS. 7A-B—Broad range of Ab concentration on peptide pulsed JY cells. JY cells were pulsed with 50 µM of the Gag$_{77-85}$ and interacted with increasing concentrations of E5 Fab Ab (FIG. 7A) or whole IgG E5 Ab (FIG. 7B). Black—Cells with αHF (anti human Fab, labeled with FITC); Red—cells with 100 µg/ml antibody; Light green—cells with 50 mg/ml antibody; Blue—cells with 10 µg/ml antibody; Purple—cells with 2 µg/ml antibody; Aqua—cells with 0.4 µg/ml antibody; Yellow—cells with 0.08 µg/ml antibody; Brown—cells with 0.016 µg/ml antibody; and Dark green—cells with 3.2×10$^{-3}$ µg/ml antibody. Quantification of the results is presented in Table 3 in Example 5 of the Examples section which follows. Note that the staining intensity is 25 times stronger with the whole IgG E5 Ab on cells loaded with 50 µM peptide comparing to Fab E5 Ab. FIGS. 7C-D—Flow cytometry analysis using 20 µg/ml of the Fab (FIG. 7C) or whole IgG (FIG. 7D) E5 antibody using decreasing amounts of the Gag$_{77-85}$ peptide loaded on APCs. Black—200 µM of the 280V (SEQ ID NO:47) peptide; Red—200 µM of the Gag$_{77-85}$ peptide; Light green—100 µM of the Gag$_{77-85}$ peptide; Dark blue—12.5 µM of the Gag$_{77-85}$ peptide; Purple—6.25 µM of the Gag$_{77-85}$ peptide; Aqua—1.56 µM of the Gag$_{77-85}$ peptide; Yellow—0.78 µM of the Gag$_{77-85}$ peptide; Brown—0.39 µM of the Gag$_{77-85}$ peptide; Dark green—0.29 µM of the Gag$_{77-85}$ peptide; and Pigment blue—0.09 µM of the Gag$_{77-85}$ peptide. Quantification of the results is presented in Table 4 in Example 5 of the Examples section which follows. Note that the staining intensity at the low mM range was sufficient to detect binding with the whole IgG E5 Ab. Specific ligand detection sensitivity was observed with as low as 4 times lower peptide concentration for the whole E5 IgG Ab.

Figure 8E:
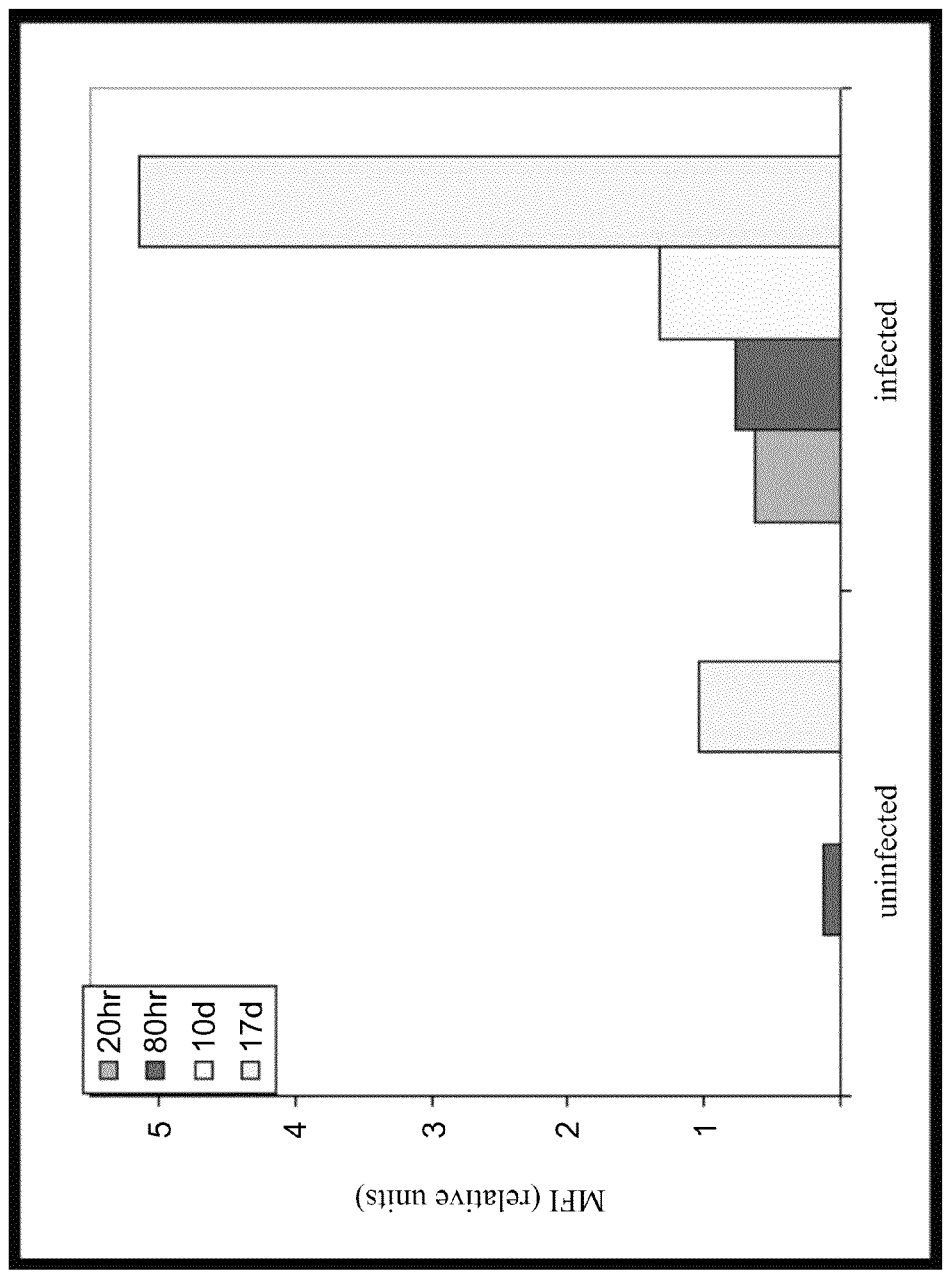

FIGS. 8A-E depict binding of E5 IgG antibody to T-1 cells infected with HXB-2 virus. T-1 cells were infected with HXB2 virus at multiplicity of infection (MOI) of 1 Infectious Unit (IU)/ml. The efficiency of infection, measured using FACS by staining the cells with αp24 (anti p24) Ag+αmFITC (anti mouse FITC), was found to be 80-100% (data are not shown). FIGS. 8A-D—FACS analyses with the E5 IgG antibody (5 or 10 µg/ml) depicting the processing of the Gag$_{77-85}$ epitope and its presentation on the cell-membrane as function of time post infection. FIG. 8A—20 hours post infection; FIG. 8B—80 hours post infection; FIG. 8C—10 days post infection; FIG. 8D—17 days post infection. Black lines—uninfected cells in the absence of the E5 antibody (marked by PBS) or the anti-human PE (αHPE) secondary antibody (marked by PBS); Red lines—uninfected cells in the presence of the E5 antibody and the αHPE antibody; Green line—infected cells in the absence of the E5 antibody (PBS) but in the presence of the αHPE antibody; Blue lines—infected cells in the presence of the E5 antibody and the αHPE antibody. FIG. 8E—a histogram depicting the binding of the E5 IgG antibody to uninfected or infected cells with the HIV virus following 20 hours, 80 hours, 10 days and 17 days based on the FACS graphs in FIGS. 8A-D. The values of the binding in infected cells was obtained by subtracting the values of the green plots from those of the blue plots. The values of the binding in uninfected cells was obtained by subtracting the values of the black plots from those of the red plots. The staining pattern revealed that 10, 17 days after infection a specific staining on virus infected cells is observed, but not on the uninfected cells. Data are representative of 3 experiments.

FIGS. 9A-D depict the sequences of the E5 antibody which is specific to the HLA-A2/GAG$_{77-85}$ complex. FIG. 9A—amino acid sequence of the light chain (SEQ ID NO:15); FIG. 9B—nucleic acid sequence of the light chain (SEQ ID NO:16); FIG. 9C—amino acid sequence of the heavy chain (SEQ ID NO:17); FIG. 9D—nucleic acid sequence of the heavy chain (SEQ ID NO:18). CDRs are marked in red; Constant region sequences are highlighted in yellow; Connector sequence is highlighted in green; His tag is highlighted in purple; Myc tag is highlighted in aqua.

DESCRIPTION OF SPECIFIC EMBODIMENTS OF THE INVENTION

The present invention, in some embodiments thereof, relates to isolated antibodies which specifically bind a complex of an MHC and an HIV antigen, and more particularly, but not exclusively, to methods of using same for detecting cells infected with the HIV virus and diagnosing and treating HIV infection or AIDS in a subject.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While reducing the invention to practice, the present inventors have isolated antibodies which can specifically bind to a complex of an MHC heavy chain and an HIV MHC-restricted antigen but not to the MHC heavy chain or the HIV antigen when not in complex.

Thus, as described in the Examples section which follows, the present inventors have isolated antibodies (e.g., clones F1, H7 and E5) which specifically bind the complex of HLA-A2/

Gag$_{77-85}$ (SEQ ID NO:2) but not complexes of the HLA-A2 and control antigenic peptides nor to the antigenic peptide alone (FIG. 1A, Example 1; FIG. 2A and data not shown, Example 2). Further analysis with the recombinant soluble Fab E5 antibody revealed a very selective binding to cells presenting the MHC-peptide complex against which the antibodies were selected but not to other MHC-peptide complexes (FIG. 2B; Example 2). Moreover, Fab-tetramers generated from the E5 Fab antibody (sequences thereof are shown in FIGS. 9A-D) were found to exhibit increased avidity and specificity to cells displaying the MHC/GAG$_{77-85}$ complex as compared with the Fab monomer (FIG. 3; Example 3). The multivalent composition (e.g., the E5 Fab tetramers) was also capable of binding the authentic HLA-A2/GAG$_{77-85}$ complex after naturally occurring intracellular processing of the gene in virus-infected cells (FIGS. 4A and B; Example 3). Furthermore, when conjugated to a toxin, the Fab E5 antibody maintained its specificity to the HLA-A2/GAG$_{77-85}$ complex and was shown to specifically kill cells presenting the HLA-A2/GAG$_{77-85}$ complex (FIGS. 5A-B; Example 4). As is further shown in Example 5 of the Examples section which follows, the present inventors have generated whole antibodies with the specificity of the E5 Fab to the MHC/HIV complex, yet, with higher avidity (FIGS. 6A-B, and FIGS. 7A-D, Example 5). The E5 IgG antibody was capable of detecting the complex of HLA-A2/GAG$_{77-85}$ on cells infected with the virus at 10 and 17 days after infection (FIGS. 8A-D, Example 5). These highly selective antibodies can be used to diagnose and treat HIV/AIDS in a subject.

Thus, according to an aspect of some embodiments of the present invention there is provided an isolated antibody comprising an antigen recognition domain capable of binding an MHC molecule being complexed with a human immunodeficiency virus (HIV) peptide derived from an HIV polypeptide selected from the group consisting of Pr55(Gag) (SEQ ID NO:1), envelope surface glycoprotein gp160 (SEQ ID NO:21), Vif (SEQ ID NO:22), Tat (SEQ ID NO:23), Rev (SEQ ID NO:24), Vpr (SEQ ID NO:25), Vpu (SEQ ID NO:26), Nef (SEQ ID NO:27), integrase (SEQ ID NO:30), Gag-Pol Transframe peptide (SEQ ID NO:31), Retropepsin (SEQ ID NO:32), gag-pol fusion polyprotein (HIV2) (SEQ ID NO:34) and gag polyprotein (HIV2) (SEQ ID NO:35), wherein the antibody does not bind the MHC molecule in an absence of the complexed peptide, and wherein the antibody does not bind the peptide in an absence of the MHC molecule.

As used herein the term "isolated" refers to at least partially separated from the natural environment e.g., the human body.

According to some embodiments the term "isolated" refers to a soluble molecule (e.g., a soluble antibody).

According to some embodiments of the invention, the antigen recognition domain of the isolated antibody of the invention comprises complementarity determining region (CDR) amino acid sequences SEQ ID NOs:3-8. The light chain of the antibody comprises CDR amino acid sequences SEQ ID NOs:3 (CDR1), 4 (CDR2) and 5 (CDR3); and the heavy chain of the antibody comprises CDR amino acid sequences SEQ ID NOs:6 (CDR1), 7 (CDR2) and 8 (CDR3).

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligo-nucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

According to some embodiments of the invention, the antibodies are multivalent forms such as tetrameric Fabs, IgM or IgG1 antibodies, thus forming a multivalent composition with higher avidity to the target. Exemplary methods for generating tetrameric Fabs or IgG1 antibodies are described in the general materials and experimental methods of the Examples section herein below.

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including screening of phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

For in vivo use (for administering in a subject, e.g., human), the human or humanized antibody will generally tend to be better tolerated immunologically than one of non human origin since non variable portions of non human antibodies will tend to trigger xenogeneic immune responses more potent than the allogeneic immune responses triggered by human antibodies which will typically be allogeneic with the individual. It will be preferable to minimize such immune responses since these will tend to shorten the half-life, and hence the effectiveness, of the antibody in the individual. Furthermore, such immune responses may be pathogenic to the individual, for example by triggering harmful inflammatory reactions.

Alternately, an antibody of a human origin, or a humanized antibody, will also be advantageous for applications (such as targeted cell killing) in which a functional physiological effect, for example an immune response against a target cell, activated by a constant region of the antibody in the individual is desired. In these cases, an optimal functional interaction occurs when the functional portion of the antibody, such as the Fc region, and the molecule interacting therewith such as the Fc receptor or the Fc-binding complement component are of a similar origin (e.g., human origin).

Depending on the application and purpose, the antibody of the invention, which includes a constant region, or a portion thereof of any of various isotypes, may be employed. According to some embodiments of the invention, the isotype is selected so as to enable or inhibit a desired physiological effect, or to inhibit an undesired specific binding of the antibody via the constant region or portion thereof. For example, for inducing antibody-dependent cell mediated cytotoxicity (ADCC) by a natural killer (NK) cell, the isotype can be IgG; for inducing ADCC by a mast cell/basophil, the isotype can be IgE; and for inducing ADCC by an eosinophil, the isotype can be IgE or IgA. For inducing a complement cascade the antibody may comprise a constant region or portion thereof capable of initiating the cascade. For example, the antibody may advantageously comprise a Cgamma2 domain of IgG or Cmu3 domain of IgM to trigger a C1q-mediated complement cascade.

Conversely, for avoiding an immune response, such as the aforementioned one, or for avoiding a specific binding via the constant region or portion thereof, the antibody of the invention may not comprise a constant region (be devoid of a constant region), a portion thereof or specific glycosylation moieties (required for complement activation) of the relevant isotype.

As mentioned above, the antibody fragment can be a CDR peptide. Once the CDRs of an antibody are identified, using conventional genetic engineering techniques, expressible polynucleotides encoding any of the forms or fragments of antibodies described herein can be synthesized and modified in one of many ways in order to produce a spectrum of related-products.

For example, to generate the antibody of the invention, an isolated polynucleotide sequence [e.g., SEQ ID NOs:9 (encoding CDR1 of the E5 light chain), 10 (encoding CDR2 of the E5 light chain), 11 (encoding CDR3 of the E5 light chain), 12 (encoding CDR1 of the E5 heavy chain), 13 (encoding CDR2 of the E5 heavy chain), 14 (encoding CDR3 of the E5 heavy chain), 16 (encoding the E5 light chain) or 18 (encoding the E5 heavy chain)] is preferably ligated into a nucleic acid construct (expression vector) suitable for expression in a host cell. Such a nucleic acid construct includes a promoter sequence for directing transcription of the polynucleotide sequence in the cell in a constitutive or inducible manner The nucleic acid construct of the invention may also include an enhancer, a transcription and translation initiation sequence, transcription and translation terminator and a polyadenylation signal, a 5' LTR, a tRNA binding site, a packaging signal, an origin of second-strand DNA synthesis, and a 3' LTR or a portion thereof; a signal sequence for secretion of the antibody polypeptide from a host cell; additional polynucleotide sequences that allow, for example, the translation of several proteins from a single mRNA such as an internal ribosome entry site (IRES) and sequences for genomic integration of the promoter-chimeric polypeptide; sequences engineered to enhance stability, production, purification, yield or toxicity of the expressed peptide.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Various methods can be used to introduce the nucleic acid construct of the invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Recombinant viral vectors are useful for in vivo expression since they offer advantages such as lateral infection and targeting specificity. Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses.

As mentioned hereinabove, a variety of prokaryotic or eukaryotic cells can be used as host-expression systems to express the antibody of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the antibody of the invention.

Recovery of the recombinant antibody polypeptide is effected following an appropriate time in culture. The phrase "recovering the recombinant polypeptide" refers to collecting the whole fermentation medium containing the polypeptide and need not imply additional steps of separation or purification. Not withstanding the above, antibody polypeptides of the invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

As used herein, the phrase "major histocompatibility complex (MHC)" refers to a complex of antigens encoded by a group of linked loci, which are collectively termed H-2 in the mouse and human leukocyte antigen (HLA) in humans. The two principal classes of the MHC antigens, class I and class II, each comprise a set of cell surface glycoproteins which play a role in determining tissue type and transplant compatibility. In transplantation reactions, cytotoxic T-cells (CTLs) respond mainly against foreign class I glycoproteins, while helper T-cells respond mainly against foreign class II glycoproteins.

MHC class I molecules are expressed on the surface of nearly all cells. These molecules function in presenting peptides which are mainly derived from endogenously synthesized proteins to CD8+ T cells via an interaction with the αβ T-cell receptor. The class I MHC molecule is a heterodimer composed of a 46-kDa heavy chain, which is non-covalently associated with the 12-kDa light chain β-2 microglobulin. In humans, there are several MHC haplotypes, such as, for example, HLA-A2, HLA-A1, HLA-A3, HLA-A24, HLA-A28, HLA-A31, HLA-A33, HLA-A34, HLA-B7, HLA-B45 and HLA-Cw8, their sequences can be found at the kabbat data base [hyper text transfer protocol://immuno (dot) bme (dot) nwu (dot) edu]. Further information concerning MHC haplotypes can be found in Paul, B. Fundamental Immunology Lippincott-Rven Press.

Recombinant soluble MHC class I and class II complexes can be produced in large quantities are described in, for example, Denkberg, G. et al. 2002, and further in U.S. patent application Ser. No. 09/534,966 and PCT/IL01/00260 (published as WO 01/72768), all of which are incorporated herein by reference. Such soluble MHC class I molecules can be loaded with suitable HLA-restricted epitopes and used for vaccination (immunization) of non-human mammal having cells expressing the human MHC class I molecule (see Pascolo et al., J. Exp. Med. 185: 2043-2051, 1997) or be further used for screening antibodies libraries (e.g., the phage display Fab library described in the Examples section which follows).

The HIV MHC-restricted peptide can be derived from any polypeptide produced by the HIV virus. These include, but not limited to Pr55(Gag) [e.g., of Human immunodeficiency virus 1, GenBank Accession No. NP_057850.1; SEQ ID NO:1, Gag-Pol precursor [e.g., of human immunodeficiency virus 1, GenBank Accession No. NP_057849.4; SEQ ID NO:20], Envelope surface glycoprotein gp160 [e.g., of human immunodeficiency virus 1, GenBank Accession No. NP_057856.1; SEQ ID NO:21], Vif [e.g., of Human immunodeficiency virus 1, GenBank Accession No. NP_057851.1; SEQ ID NO:22], Tat [e.g., of human immunodeficiency virus 1, GenBank Accession No. NP_057853.1; SEQ ID NO:23], Rev [e.g., of Human immunodeficiency virus 1, GenBank Accession No. NP_057854.1, SEQ ID NO:24], Vpr [e.g., of Human immunodeficiency virus 1, GenBank Accession No. NP_057852.2, SEQ ID NO:25], Vpu [e.g., of Human immunodeficiency virus 1, GenBank Accession No. NP_057855.1; SEQ ID NO:26], Nef [e.g., of Human immunodeficiency virus 1, GenBank Accession No. NP_057857.2; SEQ ID NO:27], Pol [e.g., of Human immunodeficiency virus 1, GenBank Accession No. NP_789740.1; SEQ ID NO:28], reverse transcriptase p66 protein [e.g., of Human immunodeficiency virus 1, GenBank Accession No. NP_705927.1 (SEQ ID NO:33)], reverse transcriptase p51 subunit [e.g., of Human immunodeficiency virus 1, GenBank Accession No. NP_789739.1; SEQ ID NO:29], integrase [e.g., of Human immunodeficiency virus 1, GenBank Accession No. NP_705928.1; SEQ ID NO:30], Gag-Pol Transframe peptide [e.g., of Human immunodeficiency virus 1, GenBank Accession No. NP_787043.1; SEQ ID NO:31], Retropepsin (aspartic peptidase) [e.g., of Human immunodeficiency virus 1, GenBank Accession No. NP_705926.1; SEQ ID NO:32], gag-pol fusion polyprotein [e.g., of Human immunodeficiency virus 2, GenBank Accession No. NP_663784.1; SEQ ID NO:34], and gag polyprotein [e.g., of Human immunodeficiency virus 2, GenBank Accession No. NP_056837.1; SEQ ID NO:35]. Additional sequences of the HIV polypeptides are available through the National Center for Biotechnology Information [Hypertext Transfer Protocol://World Wide Web (dot) ncbi (dot) nlm (dot) nih (dot) gov/].

According to some embodiments of the invention, the HIV peptide is derived from an HIV polypeptide selected from the group consisting of SEQ ID NOs:1, 21, 22, 23, 24, 25, 26, 27, 30, 31, 32, 34 and 35.

According to some embodiments of the invention, the HIV peptide is set forth by SEQ ID NO:2.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time. According to some embodiments of the invention, but not in all cases necessary, these modifications should exclude anchor amino acids.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

The peptides of the invention are preferably utilized in a linear form, although it will be appreciated that in cases where cyclicization does not severely interfere with peptide characteristics, cyclic forms of the peptide can also be utilized.

The peptides of the invention may include one or more non-natural or natural polar amino acids, including but not limited to serine and threonine which are capable of increasing peptide solubility due to their hydroxyl-containing side chain.

The peptides of the invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965. Large scale peptide synthesis is described by Andersson Biopolymers 2000; 55(3):227-50.

Based on accumulated experimental data, it is nowadays possible to predict which of the peptides of a protein will bind to MHC class I. The HLA-A2 MHC class I has been so far characterized better than other HLA haplotypes, yet predictive and/or sporadic data is available for all other haplotypes.

With respect to HLA-A2 binding peptides, assume the following positions (P1-P9) in a 9-mer peptide: P1-P2-P3-P4-P5-P6-P7-P8-P9.

The P2 and P2 positions include the anchor residues which are the main residues participating in binding to MHC molecules. Amino acid resides engaging positions P2 and P9 are hydrophilic aliphatic non-charged natural amino (examples being Ala, Val, Leu, Ile, Gln, Thr, Ser, Cys, preferably Val and Leu) or of a non-natural hydrophilic aliphatic non-charged amino acid [examples being norleucine (Nle), norvaline (Nva), α-aminobutyric acid]. Positions P1 and P3 are also known to include amino acid residues which participate or assist in binding to MHC molecules, however, these positions can include any amino acids, natural or non-natural. The other positions are engaged by amino acid residues which typically do not participate in binding, rather these amino acids are presented to the immune cells. Further details relating to the binding of peptides to MHC molecules can be found in Parker, K. C., Bednarek, M. A., Coligan, J. E., Scheme for ranking potential HLA-A2 binding peptides based on independent binding of individual peptide side-chains. J Immunol. 152, 163-175, 1994, see Table V, in particular. Hence, scoring of HLA-A2.1 binding peptides can be performed using the HLA Peptide Binding Predictions software approachable through a worldwide web interface at hypertexttransferprotocol://worldwideweb (dot) bimas (dot) dcrt (dot) nih (dot) gov/molbio/hla_bind/index. This software is based on accumulated data and scores every possible peptide in an analyzed protein for possible binding to MHC HLA-A2.1 according to the contribution of every amino acid in the peptide. Theoretical binding scores represent calculated half-life of the HLA-A2.1-peptide complex.

Hydrophilic aliphatic natural amino acids at P2 and P9 can be substituted by synthetic amino acids, preferably Nleu, Nval and/or α-aminobutyric acid. P9 can be also substituted by aliphatic amino acids of the general formula —HN(CH2)nCOOH, wherein n=3-5, as well as by branched derivatives thereof, such as, but not limited to,

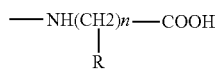

wherein R is, for example, methyl, ethyl or propyl, located at any one or more of the n carbons.

The amino terminal residue (position P1) can be substituted by positively charged aliphatic carboxylic acids, such as, but not limited to, H2N(CH2)nCOOH, wherein n=2-4 and H2N—C(NH)—NH(CH2)nCOOH, wherein n=2-3, as well as by hydroxy Lysine, N-methyl Lysine or ornithine (Orn). Additionally, the amino terminal residue can be substituted by enlarged aromatic residues, such as, but not limited to, H2N—(C6H6)-CH2-COOH, p-aminophenyl alanine, H2N—F(NH)—NH—(C6H6)-CH2-COOH, p-guanidinophenyl alanine or pyridinoalanine (Pal). These latter residues may form hydrogen bonding with the OH— moieties of the HIV residues at the MHC-1 N-terminal binding pocket, as well as to create, at the same time aromatic-aromatic interactions.

Derivatization of amino acid residues at positions P4-P8, should these residues have a side-chain, such as, OH, SH or NH2, like Ser, Tyr, Lys, Cys or Orn, can be by alkyl, aryl, alkanoyl or aroyl. In addition, OH groups at these positions may also be derivatized by phosphorylation and/or glycosylation. These derivatizations have been shown in some cases to enhance the binding to the T cell receptor.

Longer derivatives in which the second anchor amino acid is at position P10 may include at P9 most L amino acids. In some cases shorter derivatives are also applicable, in which the C terminal acid serves as the second anchor amino residue.

Cyclic amino acid derivatives can engage position P4-P8, preferably positions P6 and P7. Cyclization can be obtained through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N((CH2)n-COOH)—C(R)H—COOH or H—N((CH2)n-COOH)—C(R)H—NH2, wherein n=1-4, and further wherein R is any natural or non-natural side chain of an amino acid.

Cyclization via formation of S—S bonds through incorporation of two Cys residues is also possible. Additional side-chain to side chain cyclization can be obtained via formation of an interaction bond of the formula —(—CH2-)n-S—CH2-C—, wherein n=1 or 2, which is possible, for example, through incorporation of Cys or homoCys and reaction of its free SH group with, e.g., bromoacetylated Lys, Orn, Dab or Dap.

According to an aspect of some embodiments of the invention, there is provided a molecule comprising the antibody of the invention being conjugated to a functional moiety (also referred to as an "immunoconjugate") such as a detectable or a therapeutic moiety. The immunoconjugate molecule can be an isolated molecule such as a soluble and/or a synthetic molecule.

Various types of detectable or reporter moieties may be conjugated to the antibody of the invention. These include, but not are limited to, a radioactive isotope (such as [125] iodine), a phosphorescent chemical, a chemiluminescent chemical, a fluorescent chemical (fluorophore), an enzyme, a fluorescent polypeptide, an affinity tag, and molecules (contrast agents) detectable by Positron Emission Tomagraphy (PET) or Magnetic Resonance Imaging (MRI).

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like. For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350,466 to Targesome, Inc.]. Fluorescence detection methods which can be used to detect the antibody when conjugated to a fluorescent detectable moiety include, for example, fluorescence activated flow cytometry (FACS), immunofluorescence confocal microscopy, fluorescence in-situ hybridization (FISH) and fluorescence resonance energy transfer (FRET).

Numerous types of enzymes may be attached to the antibody of the invention [e.g., horseradish peroxidase (HPR), beta-galactosidase, and alkaline phosphatase (AP)] and detection of enzyme-conjugated antibodies can be performed using ELISA (e.g., in solution), enzyme-linked immunohistochemical assay (e.g., in a fixed tissue), enzyme-linked chemiluminescence assay (e.g., in an electrophoretically separated protein mixture) or other methods known in the art [see e.g., Khatkhatay M I. and Desai M., 1999. J Immunoassay 20:151-83; Wisdom G B., 1994. Methods Mol Biol. 32:433-40; Ishikawa E. et al., 1983. J Immunoassay 4:209-327; Oellerich M., 1980. J Clin Chem Clin Biochem. 18:197-208; Schuurs A H. and van Weemen B K., 1980. J Immunoassay 1:229-49).

The affinity tag (or a member of a binding pair) can be an antigen identifiable by a corresponding antibody [e.g., digoxigenin (DIG) which is identified by an anti-DIG antibody) or a molecule having a high affinity towards the tag [e.g., streptavidin and biotin]. The antibody or the molecule which binds the affinity tag can be fluorescently labeled or conjugated to enzyme as described above.

Various methods, widely practiced in the art, may be employed to attach a streptavidin or biotin molecule to the antibody of the invention. For example, a biotin molecule may be attached to the antibody of the invention via the recognition sequence of a biotin protein ligase (e.g., BirA) as described in the Examples section which follows and in Denkberg, G. et al., 2000. Eur. J. Immunol. 30:3522-3532. Alternatively, a streptavidin molecule may be attached to an antibody fragment, such as a single chain Fv, essentially as described in Cloutier S M. et al., 2000. Molecular Immunology 37:1067-1077; Dubel S. et al., 1995. J Immunol Methods 178:201; Huston J S. et al., 1991. Methods in Enzymology 203:46; Kipriyanov S M. et al., 1995. Hum Antibodies Hybridomas 6:93; Kipriyanov S M. et al., 1996. Protein Engineering 9:203; Pearce L A. et al., 1997. Biochem Molec Biol Intl 42:1179-1188).

Functional moieties, such as fluorophores, conjugated to streptavidin are commercially available from essentially all major suppliers of immunofluorescence flow cytometry reagents (for example, Pharmingen or Becton-Dickinson).

According to some embodiments of the invention, biotin conjugated antibodies are bound to a streptavidin molecule to form a multivalent composition (e.g., a dimmer or tetramer form of the antibody).

Table 1 provides non-limiting examples of identifiable moieties which can be conjugated to the antibody of the invention.

TABLE 1

Table 1.

| Identifiable Moiety | Amino Acid sequence (GenBank Accession No.)/ SEQ ID NO: | Nucleic Acid sequence (GenBank Accession No.)/ SEQ ID NO: |
| --- | --- | --- |
| Green Fluorescent protein | AAL33912/19 | AF435427/48 |
| Alkaline phosphatase | AAK73766/52 | AY042185/53 |
| Peroxidase | CAA00083/54 | A00740/55 |
| Histidine tag | Amino acids 264-269 of GenBank Accession No. AAK09208/56 | Nucleotides 790-807 of GenBank Accession No. AF329457/57 |
| Myc tag | Amino acids 273-283 of GenBank Accession No. AAK09208/58 | Nucleotides 817-849 of GenBank Accession No. AF329457/59 |
| Biotin lygase tag | LHHILDAQKMVWNHR/36 | |
| orange fluorescent protein | AAL33917/60 | AF435432/61 |
| Beta galactosidase | ACH42114/62 | EU626139/63 |
| Streptavidin | AAM49066/64 | AF283893/65 |

As mentioned, the antibody may be conjugated to a therapeutic moiety. The therapeutic moiety can be, for example, a cytotoxic moiety, a toxic moiety, a cytokine moiety and a second antibody moiety comprising a different specificity to the antibodies of the invention.

Non-limiting examples of therapeutic moieties which can be conjugated to the antibody of the invention are provided in Table 2, hereinbelow.

TABLE 2

Table 2.

| Therapeutic moiety | Amino acid sequence (GenBank Accession No.)/SEQ ID NO: | Nucleic acid sequence (GenBank Accession No.)/SEQ ID NO: |
| --- | --- | --- |
| *Pseudomonas* exotoxin | ABU63124/66 | EU090068/67 |
| Diphtheria toxin | AAV70486/68 | AY820132.1/69 |
| interleukin 2 | CAA00227/70 | A02159/71 |
| CD3 | P07766/72 | X03884/73 |
| CD16 | NP_000560.5/74 | NM_000569.6/75 |
| interleukin 4 | NP_000580.1/76 | NM_000589.2/77 |
| HLA-A2 | P01892/78 | K02883/79 |
| interleukin 10 | P22301/80 | M57627/81 |
| Ricin toxin | EEF27734/82 | EQ975183/83 |

According to some embodiments of the invention, the toxic moiety is PE38KDEL (SEQ ID NO:84 for the amino acid sequence; SEQ ID NO:85 for the nucleic acid sequence).

The functional moiety (the detectable or therapeutic moiety of the invention) may be attached or conjugated to the antibody of the invention in various ways, depending on the context, application and purpose.

When the functional moiety is a polypeptide, the immunoconjugate may be produced by recombinant means. For example, the nucleic acid sequence encoding a toxin (e.g., PE38KDEL) or a fluorescent protein [e.g., green fluorescent protein (GFP), red fluorescent protein (RFP) or yellow fluorescent protein (YFP)] may be ligated in-frame with the nucleic acid sequence encoding the antibody of the invention (e.g., SEQ ID NOs:16 and 18) and be expressed in a host cell to produce a recombinant conjugated antibody. Alternatively, the functional moiety may be chemically synthesized by, for example, the stepwise addition of one or more amino acid residues in defined order such as solid phase peptide synthetic techniques.

A functional moiety may also be attached to the antibody of the invention using standard chemical synthesis techniques widely practiced in the art [see e.g., hypertexttransferprotocol://worldwideweb (dot) chemistry (dot) org/portal/Chemistry)], such as using any suitable chemical linkage, direct or indirect, as via a peptide bond (when the functional moiety is a polypeptide), or via covalent bonding to an intervening linker element, such as a linker peptide or other chemical moiety, such as an organic polymer. Chimeric peptides may be linked via bonding at the carboxy (C) or amino (N) termini of the peptides, or via bonding to internal chemical groups such as straight, branched or cyclic side chains, internal carbon or nitrogen atoms, and the like. Description of fluorescent labeling of antibodies is provided in details in U.S. Pat. Nos. 3,940,475, 4,289,747, and 4,376,110.

Exemplary methods for conjugating peptide moieties (therapeutic or detectable moieties) to the antibody of the invention are described herein below:

SPDP Conjugation—

A non-limiting example of a method of SPDP conjugation is described in Cumber et al. (1985, Methods of Enzymology 112: 207-224). Briefly, a peptide, such as a detectable or therapeutic moiety (e.g., 1.7 mg/ml) is mixed with a 10-fold excess of SPDP (50 mM in ethanol); the antibody is mixed with a 25-fold excess of SPDP in 20 mM sodium phosphate, 0.10 M NaCl pH 7.2 and each of the reactions is incubated for about 3 hours at room temperature. The reactions are then dialyzed against PBS. The peptide is reduced, e.g., with 50 mM DTT for 1 hour at room temperature. The reduced peptide is desalted by equilibration on G-25 column (up to 5% sample/column volume) with 50 mM $KH_2PO_4$ pH 6.5. The reduced peptide is combined with the SPDP-antibody in a molar ratio of 1:10 antibody:peptide and incubated at 4° C. overnight to form a peptide-antibody conjugate.

Glutaraldehyde Conjugation—

A non-limiting example of a method of glutaraldehyde conjugation is described in G. T. Hermanson (1996, "Antibody Modification and Conjugation, in Bioconjugate Techniques, Academic Press, San Diego). Briefly, the antibody and the peptide (1.1 mg/ml) are mixed at a 10-fold excess with 0.05% glutaraldehyde in 0.1 M phosphate, 0.15 M NaCl pH 6.8, and allowed to react for 2 hours at room temperature. 0.01 M lysine can be added to block excess sites. After-the reaction, the excess glutaraldehyde is removed using a G-25 column equilibrated with PBS (10% v/v sample/column volumes)

Carbodiimide Conjugation—

Conjugation of a peptide with an antibody can be accomplished using a dehydrating agent such as a carbodiimide, e.g., in the presence of 4-dimethyl aminopyridine. Carbodiimide conjugation can be used to form a covalent bond between a carboxyl group of peptide and an hydroxyl group of an antibody (resulting in the formation of an ester bond), or an amino group of an antibody (resulting in the formation of an amide bond) or a sulfhydryl group of an antibody (resulting in the formation of a thioester bond). Likewise, carbodiimide coupling can be used to form analogous covalent bonds between a carbon group of an antibody and an hydroxyl, amino or sulfhydryl group of the peptide [see, J. March, Advanced Organic Chemistry: Reaction's, Mechanism, and Structure, pp. 349-50 & 372-74 (3d ed.), 1985]. For example, the peptide can be conjugated to an antibody via a covalent bond using a carbodiimide, such as dicyclohexylcarbodiimide [B. Neises et al. (1978), Angew Chem., Int. Ed. Engl. 17:522; A. Hassner et al. (1978, Tetrahedron Lett. 4475); E. P. Boden et al. (1986, J. Org. Chem. 50:2394) and L. J. Mathias (1979, Synthesis 561)].

As mentioned above and further illustrated in the Examples section which follows, the isolated antibodies of the invention can be used to detect the complex of MHC and HIV antigenic peptide on the surface of cells such as HIV-infected cells.

Thus, according to an aspect of some embodiments of the invention, there is provided a method of detecting a cell expressing an HIV antigen, comprising contacting the cell with the isolated antibody of the invention, the molecule comprising the antibody conjugated to a detectable moiety and/or the multivalent composition comprising same, under conditions which allow immunocomplex formation, wherein a presence or a level above a predetermined threshold of the immunocomplex is indicative of HIV expression in the cell.

The cell expressing the HIV antigen can be any nucleated cell such as an antigen presenting cells (APC) present in the blood.

Contacting the cell with the antibody/molecule or multivalent composition of the invention may be effected in vitro (e.g., in a cell line), ex vivo or in vivo.

As mentioned, the method of the invention is effected under conditions sufficient to form an immunocomplex; such conditions (e.g., appropriate concentrations, buffers, temperatures, reaction times) as well as methods to optimize such conditions are known to those skilled in the art, and examples are disclosed herein. As used herein the phrase "immunocomplex" refers to a complex which comprises the antibody of the invention and the MHC-HIV peptide complex. Determining a presence or level of the immunocomplex of the invention is dependent on the detectable moiety to which the antibody is attached, and can be performed using various methods are known in the art and described hereinabove.

The level of the immunocomplex in the tested cell (e.g., a cell of a subject in need thereof) is compared to a predetermined threshold. The threshold may be determined based on a known reference level and/or a level in a control cell. The control cell can be obtained from a control, healthy subject (e.g., a subject not infected with the HIV virus) or from a subject devoid of the specific MHC molecule forming the MHC-peptide complex (e.g., HLA-A2). According to some embodiments of the invention, the control subject is of the same species e.g. human, preferably matched with the same age, weight, sex etc. as the subject in need thereof.

Thus, the teachings of the invention can be used to diagnose an HIV infection in a subject by detecting an HIV-infected cell(s) in a biological sample of the subject.

As used herein the phrase "HIV-infected cell" refers to any cell or a portion thereof of the subject which displays the complex of MHC and MHC-restricted HIV antigen.

The biological sample can be any sample which contains cells or a portion thereof (e.g., cell debris, membrane vesicles) which putatively present the MHC-HIV antigenic peptide complex.

According to some embodiments of the invention, the subject is at risk of infection with the HIV virus.

As used herein the term "diagnosing" refers to determining presence or absence of a pathology, classifying a pathology or a symptom, determining a severity of the pathology, monitoring pathology progression, forecasting an outcome of a pathology and/or prospects of recovery.

To facilitate diagnosis, the above teachings can be combined with other methods of diagnosing HIV which are well known in the art include but are not limited to detection of HIV antibodies in the blood and/or detection of HIV specific antigens such as the p24 antigen [Patton J C, et al., Evaluation of the ultrasensitive human immunodeficiency virus type 1 (HIV-1) p24 antigen assay performed on dried blood spots for diagnosis of HIV-1 infection in infants. Clin Vaccine Immunol. 2008 February; 15(2):388-91. Epub 2007 Dec. 5], the p17 antigen [Ishikawa S., et al. Sensitive enzyme immunoassay of antibodies to HIV-1 p17 antigen using indirectly immobilized recombinant p17 for diagnosis of HIV-1 infection. J Clin Lab Anal. 1998; 12(6):343-50] and the reverse transcriptase antigen [Ishikawa S, et al. Whole saliva dried on filter paper or diagnosis of HIV-1 infection by detection of antibody IgG to HIV-1 with ultrasensitive enzyme immunoassay using recombinant reverse transcriptase as antigen. J Clin Lab Anal. 1996; 10(1):35-41].

The teachings of the invention can be used to treat a subject who is infected with the HIV virus.

Thus, according to an aspect of some embodiments of the invention, there is provided a method of treating AIDS, comprising administering to a subject in need thereof a therapeutically effective amount of the isolated antibody of the invention, the molecule of the invention (e.g., which includes the antibody conjugated to a therapeutic moiety such as toxin), the multivalent composition comprising same, the isolated polynucleotide or the nucleic acid construct encoding same, thereby treating the AIDS.

The term "treating" refers to inhibiting or arresting the development of a disease, disorder or condition and/or causing the reduction, remission, or regression of a disease, disorder or condition. Those of skill in the art will understand that various methodologies and assays can be used to assess the development of a disease, disorder or condition, and similarly, various methodologies and assays may be used to assess the reduction, remission or regression of a disease, disorder or condition.

According to some embodiments of the invention, the isolated antibody, molecule, multivalent composition, polynucleotide, and/or nucleic acid construct of the invention is capable of killing HIV-infected cells in the subject in need thereof.

The antibodies of the invention, the molecule of the invention (which comprise the antibody conjugated to a therapeutic or detectable moiety), the multivalent composition of the invention, the isolated polynucleotide or the nucleic acid construct of the invention may be provided per se or may be administered as a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the antibody of the invention, the molecule of the invention (which comprise the antibody conjugated to a therapeutic or detectable moiety), the multivalent composition of the invention, the isolated polynucleotide or the nucleic acid construct of the invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the invention may also be formulated in rectal compositions such as suppositories or retention enemas, using, e.g., conventional suppository bases such as cocoa butter or other glycerides.

Pharmaceutical compositions suitable for use in context of the invention include compositions wherein the active ingredients are contained in an amount effective to achieve the intended purpose. More specifically, a therapeutically effective amount means an amount of active ingredients [the antibody of the invention, the molecule of the invention (which comprise the antibody conjugated to a therapeutic or detectable moiety), the multivalent composition of the invention, the isolated polynucleotide or the nucleic acid construct of the invention] effective to prevent, alleviate or ameliorate symptoms of a disorder (HIV infection) or prolong the survival of the subject being treated.

Determination of a therapeutically effective amount is well within the capability of those skilled in the art, especially in light of the detailed disclosure provided herein.

For example, the effect of the active ingredients (e.g., the antibody of the invention) on HIV/AIDS treatment can be evaluated by monitoring the killing of HIV-infected cells since the antibody binds to class I HIV-derived MHC-peptide complexes presented on HIV-infected cells. Methods of detecting cell killing are known in the art and include, for example, assays which detect protein synthesis (e.g., incorporation of $^3$H-Leucine into cellular proteins as shown in FIG. 5B), Ethidium homodimer-1 staining (Invitrogen-Molecular Probes), the Tunnel assay (Roche, Basel, Switzerland), the Live/dead viability/cytotoxicity two-color fluorescence assay (Molecular Probes, Inc., L-3224, Eugene, Oreg., USA), FACS analysis [using molecules capable of specifically binding cells undergoing apoptosis, such as propidium iodide and Annexin V] and the like.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

According to some embodiments of the invention, the therapeutic agent of the invention (e.g., the antibody, molecule or multivalent composition of the invention) can be provided to the subject in combination with other drug(s) designed for treating HIV/AIDS (combination therapy). Such a combination therapy may increase the therapeutic effect of the agent of the invention in the treated subject.

Non-limiting examples of known anti-HIV drugs which can be co-administered to the subject in combination with the therapeutic agent of the invention include, but are not limited to entry and fusion inhibitors such as Celsentri (Selzentry), DP 178 (Fuzeon), DP178 (Fuzeon), Enfuvirtide (Fuzeon), Fuzeon (Fuzeon), MVC (Selzentry), Maraviroc (Selzentry), Pentafuside (Fuzeon), Selzentry (Selzentry), T 20 (Fuzeon), T-20 (Fuzeon), UK-427,857 (Selzentry); integrase inhibitors such as Isentress (Isentress), MK-0518 (Isentress), MK0158 (Isentress), RAL (Isentress) and Raltegravir (Isentress); non-nucleoside reverse transcriptase inhibitors such as 136817-59-9 (Rescriptor), BI-RG-587 (Viramune), DLV (Rescriptor), DMP-266 (Sustiva), Delavirdine (Rescriptor), Delavirdine mesylate (Rescriptor), EFV (Sustiva), ETR (Intelence), ETV (Intelence), Efavirenz (Sustiva), Etravirine (TMC125) (Intelence), Intelence (Intelence), L 743726 (Sustiva), NVP (Viramune), Nevirapine (Viramune), Rescriptor (Rescriptor), Stocrin (Sustiva), Sustiva (Sustiva), TMC 125 (Intelence), TMC-125 (Intelence), TMC125 (Intelence), U-901525 (Rescriptor), and Viramune (Viramune); nucleoside reverse transcriptase inhibitors such as 3TC (Epivir), 524W91 (Emtriva), ABC (Ziagen), ABC sulfate (Ziagen), AZT (Retrovir), Abacavir (Ziagen), Abacavir sulfate (Ziagen), Abacavir sulfate/Lamivudine (Trizivir), Abacavir sulfate/Lamivudine (Epzicom), Abacavir/Lamivudine (Epzicom), Abacavir/Lamivudine/Zidovudine (Trizivir), Azidothymidine (Retrovir), BMY 40900 (Videx, Videx EC), BMY-27857 (Zerit), BRN 3619529 (Videx, Videx EC), BW524W91 (Emtriva), CCRIS 805 (Videx, Videx EC), Combivir (Combivir), Coviracil (Emtriva), Didanosine (Videx, Videx EC), Dideoxyinosine (Videx, Videx EC), Emtricitabina (Emtriva), Emtricitabine (Emtriva), Emtricitabine/Tenofovir disopr (Truvada), Emtriva (Emtriva), Epivir (Epivir), Epivir-HBV (Epivir), Epzicom (Epzicom), Estavudina (Zerit), FTC (Emtriva), GS-4331-05 (Viread), HSDB 6548

(Videx, Videx EC), Lamivudine (Epivir), Lamivudine/Zidovudine (Combivir), PMPA Prodrug (Viread), Retrovir (Retrovir), Stavudine (Zerit), TDF (Viread), Tenofovir DF (Viread), Tenofovir disoproxil fumarate (Viread), Trizivir (Trizivir), Truvada (Truvada), Videx (Videx, Videx EC), Videx EC (Videx, Videx EC), Viread (Viread), ZDV (Retrovir), Zerit (Zerit), Ziagen (Ziagen), Zidovudina (Retrovir), Zidovudine (Retrovir), d4T (Zerit), ddI (Videx, Videx EC); and protease Inhibitors such as, APV (Agenerase), ATV (Reyataz), ATZ (Reyataz), Agenerase (Agenerase), Aluvia (Kaletra), Amprenavir (Agenerase), Aptivus (Aptivus), Atazanavir (Reyataz), BMS 232632 (atazanavir) (Reyataz), BMS-232632-05 (atazanavir sulfate) (Reyataz), Crixivan (Crixivan), Darunavir (Prezista), Fosamprenavir (Lexiva), Fosamprenavir calcium (Lexiva), GW 433908 (Lexiva), GW433908 (Lexiva), IDV (Crixivan), Indinavir (Crixivan), Indinavir sulfate (Crixivan), Invirase (Invirase), Kaletra (Kaletra), L-735,524 (Crixivan), LPV/RTV (Kaletra), LPV/r (Kaletra), Lexiva (Lexiva), Lopinavir/Ritonavir (Kaletra), MK-639 (Crixivan), NFV (Viracept), Nelfinavir (Viracept), Nelfinavir mesylate (Viracept), Norvir (Norvir), Prezista (Prezista), RTV (Norvir), Reyataz (Reyataz), Ritonavir (Norvir), Ro 31-8959/003 (Saquinavir mesylate) (Invirase), SQV (Invirase), Saquinavir mesylate (Invirase), Saquinavir mesylate (Invirase), Saquinavir monomethanesulfonat (Invirase), TMC 114 (Prezista), TMC114 (Prezista), TPV (Aptivus), Telzir (Lexiva), Tipranavir (Aptivus), VX 175 (Lexiva), VX-478 (Agenerase), Vertex VX478 (Agenerase), Viracept (Viracept), f-APV (Lexiva); and combination drugs such as Efavirenz/Emtricitabine/Tenofovir disoproxil fumarate (Atripla); Lamivudine/Zidovudine (Combivir); Abacavir/Lamivudine (Epzicom); Abacavir/Lamivudine/Zidovudine (Trizivir); Zidovudine/didanosine/Lamivudine; and Emtricitabine/Tenofovir disoproxil fumarate.

Compositions of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998);

methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Production of Biotinylated scMHC/Peptide Complexes—
To construct a plasmid of a single-chain major histocompatibility complex (scMHC, in which the β2 microglobulin is covalently attached upstream of the MHC heavy chain) with site specific biotinylation site (scMHC-BirA), a peptide sequence for site specific biotinylation [LHHILDAQ KMVWNHR (SEQ ID NO:36), the lysine residue undergoing biotinylation by the BirA biotin ligase enzyme is marked] was fused at the C-terminus of the HLA-A2. The construct was subcloned into a pET-based expression vector for efficient expression in E. Coli.

Folding and Purification of Recombinant MHC/Peptide Complexes or Recombinant Fusion Molecule—
Dithioerithriol was added to a final concentration of 65 mM (10 mg/ml) to the solubilized inclusion bodies of scMHC, or fusion molecule (immunotoxin Fab/ScFv-PE) which were incubated for more than 2 hours. The reduced inclusion bodies were diluted ×100 with refolding buffer (0.1 M Tris-HCl pH=8, 0.5 M Arginine, 0.09 mM Oxidized Glutathione, 2 mM EDTA, 0.2 mM PMSF) and 5 or 10 fold molar excess of peptide (usually 1 mg/100 ml refolding buffer) was added to scMHC, previously diluted in $H_2O$ or DMSO, and incubated at 4-10° C. for 48 hours.

After refolding, the protein was dialyzed against 100 mM Urea, 20 mM Tris-HCl pH=8, and concentrated by a Minisette system using a 10 K cutoff cassette to a final volume of 200 ml. The protein was loaded on Q Sepharose anion exchange column. The column was washed with buffer A containing 5 mM NaCl, 20 mM Tris HCl pH=8, 1 mM EDTA. Relevant fractions corresponding to correctly folded MHC/peptide or fusion molecule monomers were poured to a centricon device (30 kDa cut off; Amicon, Beverly Mass.) and concentrated to volume 0.3-1.0 ml (Usually no more than 2 mg/ml to avoid protein aggregation). The clean fractions were frozen at −70° C. at this step, until further use.

Biotinylation of MHC/Peptide Complexes—
The buffer was exchanged (using the centricon) with 10 mM Tris-HCl, pH=8, 50 mM NaCl. The final protein concentration was brought to 1-2 mg/ml (25-50 μM). Enzymatic biotinylation was performed at a specific lysine residue in the heavy chain C-terminal tag using biotin protein ligase—BirA enzyme (AVIDITY, Denver, Colo.) for 16 hour at 25° C., in presence of protease inhibitors cocktail (0.1 mM PMSF, 1 μg/ml Leupeptin, 1 μg/ml Pepstatin). The buffer was exchanged and the excess biotin was removed from the biotinylated complexes using centricon 30 ultrafiltration or G-25. The MHC/peptide biotinylated monomers were frozen at −70° C.

Selection of Phage-Antibodies on Biotinylated Complexes—
A large human Fab library containing $3.7 \times 10^{10}$ different Fab clones was used for the selection [de Haard, H. J. et al. Journal of Biological Chemistry 274, 18218-18230 (1999)]. Phages ($10^{13}$) were first pre-incubated for 1 hour at room temperature in PBS containing 2% nonfat dry milk with streptavidin-coated paramagnetic beads (200 ml; Dynal, Oslo) to deplete streptavidin binders. Streptavidin-coated paramagnetic beads (200 ml; Dynal, Oslo) were also incubated in phosphate buffer saline (PBS) buffer supplemented with 2% milk for 1 hour at room temperature. The remaining phages were subsequently incubated for 1 hour with decreasing amounts of biotinylated scMHC-peptide complexes. Streptavidin magnetic beads were added, and the mixture was incubated for 15 minutes with continuous rotation. A magnetic force was applied to pull down phages bound to biotinylated complexes. After 10 washes of the streptavidin-bound complexes with PBS 0.1% Tween and 2 washes with PBS, bound phages were eluted by incubation for 7 minutes with 1 ml of Triethylamine (TEA) (100 mM). The elusion mixture was neutralized by the addition of 100 μl of Tris-HCl (1 M, pH 7.4) and used to infect E. coli TG1 cells ($OD_{600}$=0.5) for 30 minutes at 37° C. Selected phages were rescued using M13KO7 helper phage ($5 \times 10^{11}$ cfu). The diversity of the selected antibodies was determined by DNA fingerprinting. The Fab DNA of different clones was PCR-amplified using the primers pUC-reverse [5'-AGCGGATAACAATTTCA-CACAGG-3' (SEQ ID NO:37) and fd-tet-seq24 (5'-TTTGTCGTCTTTCCAGACGTTAGT-3' (SEQ ID NO:38)]. The resulting PCR fragments were digested with BstNI (NEB) (2 hours, 37° C.) and analyzed by agarose gel electrophoresis.

Cell Lines—
JY (EBV-transformed B-lymphoblast), were maintained in RPMI-1640 supplemented with 10% fetal calf serum (FCS), 2 mM glutamine, Penicillin (100 units/ml) and Streptomycin (100 μg/ml) at 37° C. with 5% $CO_2$. The HEK293 cells were maintained in Dulbecco's modified Eagle's medium (DMEM) and with 10% fetal calf serum (FCS), 2 mM glutamine and 1% Penicillin Streptomycin antibiotics, and with 0.8 mg/ml of G418, and 100 μg/ml of hygromycin. The MT-2 and T-1 virus (HXB2) transfected were maintained in Sheba Hospital, Israel.

PBMC Media:
100 ml AIM-V medium, 10% FCS, Penicillin (100 units/ml), Streptomycin (100 μg/ml) and beta-mercaptoethanol (βME; 50 μM).

Expression and Purification of Soluble Recombinant Fab Antibodies—
4 μl of miniprep DNA was transformed to 100 μl BL 21 E. coli competent cells and the bacteria was plated on 2YT/A/G agar plates and incubated over night at 37° C. Inoculated plates were transferred into Superbroth supplemented with 12 ml/liter 40 gr/liter MgSO$_4$, 5 ml/liter 20% Glucose, and 100 µg/ml Ampicillin. For each liter of Superbroth, 5 plates (full with colonies) were used which were grew to OD$_{600}$ nm=0.8-1.0 and induced to express the recombinant Fab antibody by the addition of 1 mM IPTG for 3 hours at 30° C. The cells were centrifuged and the pellet was resuspended in 5 ml of a B-PER solution (Pierce) to release periplasmatic content. After 30 minutes of rotated incubation at room temperature (RT), the solution was centrifuged (15000 rpm, 15 minutes) and the supernatant was incubated with 0.5 ml of pre-washed TALON beads suspension (Clontech) for 45 minutes at RT. The solution was applied onto a Biorad disposable column, and after sedimentation the beads were washed three times with 10 ml of PBS/0.1% Tween-20 (pH 8.0). The bound Fabs were eluted using 0.5 ml of 100 mM Imidazole in PBS. The eluted Fabs were dialyzed twice against PBS (overnight, 4° C.) to remove residual imidazole. The homogeneity and purity of the purified Fabs was determined by analysis on non-reduced and reduced SDS-PAGE.

Production of Fluorescent Tetramerized Fabs—

The genes encoding the light and heavy chain of Fab E5 were cloned separately into a T7-promotor pET-based expression vector. The light chain gene was engineered to contain the BirA recognition sequence for site-specific biotinylation at the COOH terminus (E5 light-BirA). These constructs were expressed separately in E. coli BL21 cells and upon induction with IPTG, intracellular inclusion bodies that contain large amounts of the recombinant protein accumulated. Inclusion bodies of both chains were purified, reduced, and subsequently refolded at a 1:1 ratio in a redox-shuffling buffer system containing 0.1 M Tris, 0.5 M Arginine, 0.09 mM Oxidized Glutathione (pH 8.0). Correctly folded Fab was then isolated and purified by anion exchange QSepharose chromatography (Pharmacia). The Fab peak fractions were concentrated using Centricon 30 (Amicon) to 1 mg/ml, and the buffer was exchanged to Tris-HCl [10 mM (pH 8.0)]. Biotinylation was performed using the BirA enzyme (Avidity) as described previously. Excess biotin was removed from biotinylated Fabs using a G-25 desalting column. Phycoerythrin-labeled streptavidin (Jackson-Immunoresearch) was added at a molar ratio of 1:4 to produce fluorescent tetramers of the biotinylated Fab fragment.

ELISA with Purified Fab Antibodies—

The binding specificity of each of the soluble Fab fragments was determined by ELISA using biotinylated scMHC-peptide complexes. ELISA plates (Falcon) were coated overnight with BSA-biotin (1 µg/well), washed and incubated (1 hour, RT) with streptavidin (1 µg/well), washed extensively and further incubated (1 hour, RT) with 0.5 µg of MHC/peptide complexes. Plates were blocked for 30 minutes at RT with PBS 2% BSA and subsequently were incubated for 1 hour at RT with various concentrations of soluble purified Fab, and after washing, with 1:1000 HRP-conjugated/anti-human antibody. Detection was performed using TMB (3,3', 5,5'-tetramethylbenzidine) reagent (DAKO Cat. No. S1599). The HLA-A2-restricted peptides used for specificity studies of the purified Fab antibodies are: the Human immunodeficiency virus (HIV)-derived peptide POL: ILEPVHGV (SEQ ID NO:39), hTERT (540): ILAKFLHWL (SEQ ID NO:40) and (865):RLVDDFLLV (SEQ ID NO:41), and the gp100 derived peptide G9-209: ITDQVPFSV (SEQ ID NO:42).

Flow Cytometry—

The EBV-transformed B-lymphoblast JY cells or virus infected cells were used to determine the reactivity of the recombinant TCR-like antibody with cell surface-expressed HLA-A2/peptide complexes. About 10$^6$ JY cells were washed with serum-free RPMI and incubated overnight at 37° C. in medium containing 100 µM of the peptide. The cells were incubated for 60 minutes at 4° C. with recombinant Fab antibodies or Fab-PE (10-100 µg/ml) in 100 µl. After three washes, the cells were incubated with rabbit anti-PE polyclonal antibody followed by washing twice with PBS and further incubated for 60 minutes with FITC labeled anti rabbit IgG (for Fab-PE) or with FITC-labeled anti-human Fab or with PE-labeled anti-human Fab (Jackson) (for Fab Abs). After a final wash, the cells were resuspended in ice-cold PBS.

T-1 cells which are lines of human CD4+ T-cells infected with HIV-1 virus. T-1 cells were infected with HXB2 virus at multiplicity of infection (MOI) of 1 Infectious Unit (IU)/ml (information regarding the virus can be found in the web site: Hypertext Transfer Protocol://World Wide Web (dot) hiv (dot) lanl (dot) gov/content/hiv-db/HTML/reviews/HXB2 (dot) html). The efficiency of infection as measured by staining the cells with α-p24 Ag (anti p24 antigen)+α-MFITC (anti mouse FITC) and measured by FACS was 80-100%.

T1 virus infected cells were first fixed with 2% paraformaldehyde (PFA), and then treated like JY cells.

Analysis of the cells was performed by a FACStar flow cytometer (Becton Dickinson) and the results were analyzed with the WinMDI program (Trotter Hypertext Transfer Protocol://facs (dot) Scripps (dot) edu/).

Expression and Purification of Fab-PE38 Fusion Protein—

The genes encoding the light and heavy chain of Fab E5 were cloned separately into a T7-promotor pET-based expression vector. The heavy chain gene was engineered to contain the PE38 recognition sequence at the COOH terminus (E5 heavy-PE38). These constructs were expressed separately in E. coli BL21 cells and upon induction with IPTG, intracellular inclusion bodies which contain large amounts of the recombinant protein accumulated. Inclusion bodies of both chains were purified, reduced, and subsequently refolded at a heavyPE38: light 2.5:1 ratio respectively in a redox-shuffling buffer system containing 0.1 M Tris, 0.5 M Arginine, 0.09 mM Oxidized Glutathione (pH 7.4). Correctly folded Fab was then isolated and purified by ion-exchange chromatography Sepharose and MonoQ (Pharmacia).

Cytotoxicity Assays—

JY APCs (antigen presenting cells) were loaded with specific and control peptides. Peptide-loaded cells were subsequently incubated with increasing concentrations of immunotoxin and the inhibition of protein synthesis was determined by measuring the uptake of $^3$H-Leucine into cellular proteins, as previously described (Brinkmann, U., et al., 1991, Proceedings of the National Academy of Sciences of the United States of America 88, 8616-8620). IC$_{50}$ was determined as the concentration of immunotoxin required to inhibit protein synthesis by 50%.

Cloning Fab-E5 into IgG1 Scaffold—

The Fd and light chain genes encoding the human E5 Fab were recloned for expression as human IgG1 kappa antibody. Two vectors were generated based on the backbone of the eukaryotic expression vector pCMV/myc/ER (Invitrogen No. V82320). For the heavy chain, the multiple cloning sites, the myc epitope tag, and the ER retention signal of pCMV/myc/ER were replaced by a cloning site containing recognition sites for BssHI and NheI followed by the human IgG1 constant heavy chain region cDNA isolated by RT-PCR from human lymphocyte total RNA. A similar construct was generated for the light chain in which the multiple cloning site, the myc epitope tag, and the ER retention signal of pCMV/myc/ER were replaced by a cloning site containing region sites for BssHI and XbaI. Each shuttle expression vector carries a different antibiotics resistance gene and thus expression is facilitated by co-transfection of the two constructs into human embryonic kidney HEK293 cells and selection for positive clones, by using the two antibiotics neomycin and hygromycin.

Transient Transfection—

20 μg of pcDNA3-GAG, pcDNA-POL, pcDNA3-TAX and GFP added separately to 400 μl of 20×10$^6$ JY cells and transferred into a cuvette. The DNA was electrotransferred into the cells using a pulse controller at 250 kV, 950 μF. After the electric pulse the cells were incubated for 5 minutes at RT and then transferred into 10 ml RPMI-1640 supplemented with 10% FCS, 2 mM glutamine, Penicillin (100 units/ml) and Streptomycin (100 μg/ml) and incubated for 24-48 hours at 37° C.

Stable Transfection—

Cotransfections of HEK293 cells were performed using the nonliposomal transfection reagent FuGene 6 (Roche, Brussels, Belgium) according to the manufacturer's instructions. The transfection was performed with serum free medium containing 0.8 mg/ml of G418, and 100 μg/ml of hygromycin. Forty-eight hours after transfection limiting dilutions were performed into medium containing 0.8 mg/ml of G418, and 100 μg/ml of hygromycin. Cells were plated in 96-well plates at 1000 cells per well. Medium was exchanged after 5 and 10 days. Wells in which one colony grew to 50% of the well's area, were trypsinized and further splitted into two wells: 10 μl into a 24 well plate (backup) and 30 μl into a 24 well plate (experiment). When the plate reached 80% confluency, serum starvation was initiated by reducing each day serum percentile to 0.5%. After 48 hours of incubation with 0.5% FCS, screening of cell culture supernatants was performed by ELISA and FACS assays.

Dot Blot—

The cell culture supernatant was applied via a vacuum manifold onto a nitrocellulose filter using a dot-blot apparatus. After blocking the membrane with 5% non-fat milk for 1 hour, it was washed briefly with PBS and incubated with HRP-conjugated anti-human IgG antibody (1/5000 dilution with PBS/2% milk). The membrane was developed using chloronaphtol reagent.

Production and Purification of the E5-IgG from Culture Media of HEK293 Clones—

The IgG secreting clones that exhibited the best binding reactivity by ELISA and FACS and the highest amount of protein, were selected for antibody production and purification. Protein A-Sepharose™ 4 Fast Flow beads (Amersham) were prepared according to the manufacturer's instructions. Briefly, supernatant was loaded on the Protein A-Sepharose beads at 15-50 ml/hour. Unbound immunoglobulins were washed with 0.001 M $NaH_2PO_4$ and 0.019 M $Na_2HPO_4$. Bound immunoglobulins were then eluted with 0.1M citric acid pH 3. Five fractions were collected with 250 μl of elusion buffer and immediately neutralized with 80 μl of Tris-HCl pH 9. IgG concentration was measured using the Pierce protein assay. The eluted protein was dialyzed against PBS pH 7.4 over night. 10 mgs of IgG were produced from 1L of culture supernatant.

ELISA with Culture Supernatant and Purified IgG—

ELISA plates (Falcon) were coated overnight with BSA-biotin (1 μg/well). After washing, plates were incubated (1 hour, RT) with streptavidin (1 μg/well), washed extensively and further incubated (1 hour, RT) with 0.5 μg of MHC/peptide complexes. Plates were blocked for 30 minutes at RT with PBS/2% and subsequently were incubated for 2 hours at RT with 100 μl of clone supernatants or purified IgG and 100 μl of 1% milk. After washing, plates were incubated for 1 hour at RT with 1:5000 HRP-conjugated/anti-human IgG antibody. Detection was performed using TMB reagent (Sigma). The HLA-A2-restricted peptides used for specificity studies were: $Gag_{77-85}$ (SEQ ID NO:2) and G9-209 (SEQ ID NO:42).

Flow Cytometry with Culture Supernatant or Purified IgG—

The EBV-transformed B-lymphoblast JY cells were used to determine the specificity of the supernatant of cotransfected HEK293 cells with cell surface-expressed HLA-A2/TARP complexes. About 10$^6$ JY cells were washed with serum-free RPMI and incubated overnight at 37° C. in medium containing 100 μM of the peptide. The cells were incubated for 60-90 minutes at 4° C. with 100 μl supernatant or purified IgG. After three washes the cells were incubated with PE-labeled anti-human Fab (Jackson). After a final wash, the cells were resuspended in ice-cold PBS. Analysis of the cells was performed by a FACScalibur flow cytometer (Becton Dickinson).

Example 1

Isolation of Recombinant Antibodies which Specifically Bind the HIV-GAG/MHC Complex Experimental Results Selection of TCR-Like Recombinant Antibodies Towards HLA-A2/$Gag_{77-85}$—

Recombinant peptide-HLA-A2 complexes that present the $Gag_{77-85}$ HIV-1 derived peptide (SEQ ID NO:2) were generated using a scMHC construct that was described previously (Denkberg, G., et al., 2000, European Journal of Immunology 30, 3522-3532). In this construct, the extracellular domains of HLA-A2 are connected into a single chain molecule with β2m using a 15-aa flexible linker such that the β2m is upstream of the HLA-A2 heavy chain. The scMHC/peptide complexes were produced by in vitro refolding of inclusion bodies in the presence of the HIV-1-derived $Gag_{77-85}$ peptide. The refolded scHLA-A2/Gag complexes were found to be very pure, homogenous, and monomeric by SDS-PAGE and size exclusion chromatography analyses (data not shown). Recombinant scMHC/peptide complexes generated by this strategy were previously characterized in detail for their biochemical, biophysical, and biological properties, and were found to be correctly folded and functional (Denkberg, G., et al., 2000, European Journal of Immunology 30, 3522-3532; Denkberg, G., et al., 2001, Journal of Immunology 167, 270-276). For selection of TCR-like Abs, a large antibody (Ab) phage library consisting of a repertoire of 3.7×10$^{10}$ independent human recombinant Fab clones (de Haard, H. J. et al. 1999, Journal of Biological Chemistry 274, 18218-18230) was used. The selection strategy (described under the General Materials and Experimental Methods) was first depleting the library of streptavidin binders and subsequently applying the library to panning in solution on soluble recombinant scHLA/A2-peptide complexes containing the $Gag_{77-85}$ peptide. A 10-fold enrichment in phage titer was observed after three rounds of panning. The specificity of the selected phage Abs was determined by a differential ELISA analysis on streptavidin-coated wells incubated with biotinylated scMHC HLA-A2 complexes containing either the $Gag_{77-85}$ peptide or control complexes containing other HLA-A2-restricted peptides. Phage clones analyzed after the third round of selection exhibited two types of binding patterns toward the scHLA-A2/peptide complex: one class of Abs consisted of pan-MHC binders that cannot differentiate between the various MHC-peptide complexes; the second type consisted of Abs that bound the MHC/peptide complex in a peptide-specific manner. The ELISA screen revealed that 41 of 90 randomly selected clones screened (45%) from the third round of panning appeared to be fully peptide dependent and specific for the peptide/MHC used in the selection (i.e., the scHLA-A2/Gag$_{77-85}$ complex).

A representative analysis of three TCR-like Fab clones that reacted only with the scHLA-A2/Gag$_{77-85}$ complex and not with control scHLA-A2/peptide complexes is shown in FIG. 1A. The diversity within the selected TCR-like Fabs was assessed by DNA fingerprint analysis; 4 different antibodies with TCR-like specificity were revealed, indicating the selection of several different Abs with TCR-like specificity.

Example 2

Characterization of the E5 Fab Antibody

Experimental Results

Characterization of Recombinant Soluble Fab Antibodies with TCR-Like Specificity—

Out of the four Fab clones specific for the HLA-A2-Gag-derived complex, one phage (clone E5) that exhibited the most specific peptide-dependent and TCR-like binding pattern as analyzed by the phage ELISAs was further sequenced, produced in a soluble form in *E. coli* TG1 or BL21 cells and purified by immobilized metal ion affinity chromatography (IMAC). Yields were 2-4 mg of pure material from 1 liter of bacterial culture. SDS-PAGE analysis (FIG. 1B) revealed a homogenous and pure population of Fab with the expected molecular size.

The sequences of the light chain (FIG. 9A—amino acid sequence; FIG. 9B—nucleic acid sequence) and heavy chain (FIG. 9C—amino acid sequence; FIG. 9D—nucleic acid sequence) of the E5 antibody were determined.

The Isolated E5 Fab Antibody Specifically Binds the MHC/Peptide Complex of HLA-A2/Gag$_{77-85}$ but not the HLA-A2 or the Peptide when not in Complex—

The binding specificity of the purified Fab fragment was determined by ELISA on biotinylated MHC/peptide complexes immobilized to wells through BSA-biotin-streptavidin. The correct folding of the bound complexes and their stability during the binding assays were determined by their ability to react with the conformational specific monoclonal antibody W6/32, which binds HLA complexes only when folded correctly and when it contains peptide (data not shown). When soluble purified Fabs were used, the ELISA revealed a very specific recognition pattern. Thus, the E5 Fab clone bound to the HLA-A2/Gag$_{77-85}$ complex but not to control HLA-A2/peptide complexes displaying various tumor or viral-derived T-cell epitopes (peptides) (FIG. 2A) or to the peptide alone (data not shown). Thus, the peptide-specific, MHC-restricted Fab E5 exhibited binding characteristic and fine specificity of a TCR-like molecule, which binds the MHC/peptide complex but not the MHC or the peptide when not in complex.

The affinity binding properties of the TCR-like soluble purified E5 antibody was determined by using a saturation ELISA in which biotinylated complexes were bound to BSA-biotin-streptavidin-coated plates to which increasing amounts of E5 Fab Ab were added. The binding of Fab E5 to the specific HLA-A2/Gag$_{77-85}$ complex was dose dependent and saturable (not shown). Extrapolating the 50% binding signal revealed that this antibody possessed an apparent affinity binding of 140 nanomolar.

Binding of E5 Fab Antibody to Antigen Presenting Cells (APCs) Displaying the Gag-Derived Epitope—

To demonstrate that the isolated soluble Fab E5 antibody can bind the specific MHC-peptide complex not only in its recombinant soluble form but also in the native form as expressed on the cell surface, TAP$^+$ Epstein-Barr virus (EBV)-transformed B lymphoblast JY cells, which express HLA-A2, were incubated with the Gag-derived or control peptides. These cells express TAP (transporter associated with antigen processing) and consequently, the display of exogenous peptides is facilitated by peptide exchange. By using this strategy, a mixture of exogenously and endogenously derived peptides presented on HLA-A2 and displayed on the cell surface were obtained. As shown in FIG. 2B, using the E5 Fab antibody, which is specific to the HLA-A2/Gag$_{77-85}$ complex, an intensive staining of JY cells loaded with the specific Gag$_{77-85}$-derived peptide was observed, however, no binding was observed when other control peptides were used. These results demonstrate the ability of the TCR-like E5 antibody to detect the specific Gag$_{77-85}$ MHC-peptide complex on the surface cells.

Example 3

Generation of E5 Fab Tetramers with Increased Avidity

Experimental Results

Increasing the Avidity of TCR-Like Fab E5—

The density of a particular peptide-HLA complex on cells is expected to be low as compared with peptide-pulsed APCs. In order to increase the avidity and sensitivity of the TCR-like antibody, Fab tetramers which are directly tagged with a fluorescent probe were generated. This approach was previously used to increase the binding avidity of peptide-MHC complexes to the TCR or to increase the sensitivity of recombinant Ab molecules (Cloutier, S. M. et al. 2000, Molecular Immunology 37, 1067-1077). Another advantage of using fluorescently labeled tetramers is that only a single staining step is required, whereas monomeric unlabeled Fabs require a fluorescently labeled secondary Ab. To generate Fab tetramers the BirA peptide sequence was introduced at the C-terminus of the light chain for site-specific biotinylation. Recombinant E5 Fab was refolded by in vitro refolding as described under "General Materials and Experimental Methods" and was subjected to in vitro biotinylation by the *E. coli* BirA enzyme as described previously (Cloutier, S. M. et al. 2000, Molecular Immunology 37, 1067-1077). The E5 Fab tetramers, which were generated with fluorescently labeled streptavidin, were used to measure the expression of HLA-A2/Gag$_{77-85}$ complexes on the surface of peptide pulsed APCs. As shown in FIG. 3, the fluorescence intensity measured by flow cytometry on peptide-pulsed JY cells upon the binding of the E5 Fab tetramer was significantly improved compared with the reactivity of the Fab monomer. These results further demonstrated the ability of these high affinity TCR-like Abs to detect the specific MHC-peptide complex on the surface of APCs.

Detection of Gag Complexes Formed by Active Intracellular Processing—

To examine the ability of the TCR-like E5 Fab Ab to detect HLA-A2/Gag complexes produced by physiological active intracellular antigen processing, the full length Gag gene was transfected into the EBV-transformed B cell HLA-A2-positive Antigen-presenting JY cells. Twenty-four hours after transfection, the reactivity of the HLA-A2/Gag-specific Ab E5 (in the form of a tetramer) was tested with the transfected cells by flow cytometry. As shown in FIG. 4A, significant and specific reactivity was observed with HLA-A2-positive JY cells 24 hours after transfection with the Gag gene (pVR1012X/S Gag/h (pVRC 3900)) but not with the HTLV-1-Tax gene or with vector alone. Similarly, as shown in FIG. 4B, significant and specific reactivity was observed with HLA-A2-positive JY cells 24 hours after transfection with the Gag gene but not with the HIV Pol gene or with vector alone. The efficiency of Gag gene transduction into JY cells was high as monitored by transfection with a GFP construct (FIG. 4C). Control EBV transformed APD B cells which are HLA-A2 negative were also used as controls and when transfected with the Gag gene no reactivity with the E5 Fab tetramer was observed (data not shown). These results demonstrate that Fab E5 can detect the authentic HLA-A2/Gag complex after naturally occurring intracellular processing of the gene in virus-infected cells.

Example 4

Generation of Immuno-Toxins Directed Against Cells Presenting the HIV Antigen

Experimental Results
Construction and Characterization of a Toxin Armed Recombinant E5 Fab Fusion—

To further characterize the binding specificity and the biological properties of the selected E5 Fab TCR-like antibody and to test its ability to serve as a specific targeting molecule the E5 Fab was armed with a potent truncated bacterial toxin. The E5 Fab gene was fused to a truncated form of *Pseudomonas* Exotoxin A (PE38) to generate a Fab-immunotoxin as described in Pastan, I. 1997, Biochimica et Biophysica Acta-Reviews on Cancer 1333, C1-C6. This truncated form of PE contains the translocation and ADP-ribosylation domains of whole PE but lacks the cell-binding domain, which is replaced by the Fab fragment fused at the N-terminus of the truncated toxin. The E5 light chain and heavy chain-PE38 fusion were cloned separately into a T7-promotor pET-based expression vector and were expressed in *E. coli* BL21 cells as intracellular inclusion bodies. Using established renaturation protocols, a E5 Fab-PE38 fusion molecule was refolded and purified. A highly purified E5 Fab-PE38 fusion protein with the expected molecule weight of 88 kDa was obtained as analyzed by SDS-PAGE under non reducing conditions (data not shown). The E5 Fab-immunotoxin fusion was generated with two forms of PE38, one of them contains a native C-terminal sequence which serves as an ER retention signal (REDLK).

Binding of E5 Fab-PE38 to APCs Displaying the $Gag_{77-85}$ Epitope—

To demonstrate that purified E5 Fab-PE38 can bind the specific MHC-peptide complex as expressed on the cell surface, the EBV-transformed B lymphoblast JY cells, which express HLA-A2 were used. The cells were incubated with the $Gag_{77-85}$ or control peptides and the binding of the fusion protein was tested by monitoring the reactivity of anti-PE38 antibodies. As shown in FIG. 5A, the E5 Fab-toxin fusion exhibited specific binding to JY cells loaded with the $Gag_{77-85}$ peptide but not to cells that were loaded with control tumor-derived epitope (gp100-209 peptide). These results demonstrate that the Fab-fusion can specifically recognize its corresponding native HLA-A2 complex on the surface of cells and that the reactivity was not altered as a result of fusion with the toxin. These results demonstrate that the E5 Fab-PE38 retains its specificity to Gag/HLA-A2 peptide complexes expressed on the surface of cells.

Cytotoxicity of E5 Fab-PE38 Towards JY APC Cells Displaying the Gag Derived Epitope—

The ability of the E5 (Fab)-PE38 to inhibit protein synthesis was used as a measure to test the specificity and biological activity of the TCR-like E5 Fab fusion molecule. Because the cell binding domain in the toxin was deleted, cytotoxicity induced by internalization of the Fab-Toxin fusion reflects specific antigen binding. To test this activity, JY cells were loaded with the specific $Gag_{77-85}$ peptide for which it was selected, and with the gp-100 derived peptide p-280V (SEQ ID NO:47). The loaded cells were incubated with increasing concentrations of the E5 Fab-fusion protein and protein synthesis was tested by measuring incorporation of $[^3H]$-leucine into cellular proteins. As shown in FIG. 5B, the E5 Fab-PE38 fusion inhibited protein synthesis in a dose dependent manner and was cytotoxic to JY cells loaded with the specific $Gag_{77-85}$ peptide for which it was selected, but no inhibition was observed when other peptides were tested. The cytotoxic activity correlated the reactivity of the E5 TCR-like Fab; JY cells loaded with the $Gag_{77-85}$ which react well with the antibody were killed efficiently ($IC_{50}$ of 600 ng/ml). Control JY cells loaded with control peptide were not affected by the immuno-toxin, even in the presence of high concentrations of fusion protein (e.g., 10 μg/ml). These results further demonstrate the fine and unique specificity of the E5 Fab antibody and its ability to serve as a targeting moiety to deliver a cytotoxic effector molecule with antigen (peptide)-specific, MHC-restricted specificity of T cells directed toward a human viral T-cell epitope.

Example 5

Generation of Whole Antibodies with the Specificity of the E5 Fab to the Complex of MHC/HIV Antigen Experimental Results Cloning of E5 Fab into a Mammalian Expression Vector and Selection of Transfectants into HEK293 Cells—

The E5 Fab had an affinity of about 140 nanomolar. To increase the apparent affinity, avidity and sensitivity of the TCR-like Fab for the peptide and cellular $Gag_{77-85}$ the heavy and light antibody genes encoding the human E5 Fab directed to $Gag_{77-85}$ were recloned for expression as fully human IgG1 lambda antibody into the mammalian backbone of the eukaryotic expression vector pCMV/myc/ER (Invitrogen No. V82320). For the heavy chain, the multiple cloning site, the myc epitope tag, and the ER retention signal of pCMV/myc/ER were replaced by a cloning site containing recognition sites for BssHI and NheI followed by the human IgG1 constant heavy chain region cDNA isolated by RT-PCR from human lymphocyte total RNA. A similar construct was generated for the light chain. Each shuttle expression vector carries a different antibiotics resistance gene and thus expression is facilitated by co-transfection of the two constructs into human embryonic kidney HEK293 cells. After co-transfection of HEK293 cells with the two heavy and light chain gene-containing plasmids, cells were grown on selective media. On the plate with 100 cells/well seeded, 25% of the wells showed cell growth after 5 days in culture. Antibody-producing cells were adapted to growth in 0.5% serum followed by determining the presence of human IgG in culture supernatants and binding to Gag/HLA-A2 complexes in ELISA and FACS assays.

The ELISA screen revealed that 25 of 35 wells analyzed, produced antibody which was peptide specific and bound only to scHLA-A2/Gag complexes.

To further characterize the human IgG in culture supernatants, flow cytometry analysis was performed. JY APCs were loaded with $Gag_{77-85}$ and control G9-209 peptides and incubated with culture supernatant originating from a single colony. These studies revealed that 18 of 25 clones tested were peptide specific and bound only to scHLA-A2/Gag complexes. Two third of the examined wells were positive for binding to HLA-A2/Gag complexes in ELISA and FACS assays. Next, a dot-blot analysis was performed to quantify the amount of IgG in each sample of culture supernatant.

Clones that exhibited the best binding reactivity by ELISA and FACS analysis and secreted high levels of IgG, were selected for further analysis.

Production and Purification of E5-IgG—

The Gag/HLA-A2-specific E5-IgG antibody was purified from HEK293 cells grown in 0.5% fetal calf serum. SDS-PAGE analysis of the purified protein revealed homogenous, pure IgG with the expected MW of about 200 kDa (FIG. 6A). Approximately 30 mg of highly purified IgG could be obtained from 1 Liter of culture supernatant.

Characterization of E5 IgG Antibody—

ELISA assays were performed in order to test the TCR-like binding specificity after transforming recombinant Fab fragment into whole IgG molecule. ELISA was performed on biotinylated scHLA-A2/peptide complexes that were immobilized to BSA-streptavidin-coated wells. The correct folding of the bound complexes and their stability during the binding assays was tested with the conformation-specific mAb, w6/32, that recognizes HLA complexes only when folded correctly and when containing peptide (data not shown). E5 IgG clones reacted specifically with the Gag-containing HLA-A2 complex, but not with control HLA-A2/peptide complexes displaying various tumor or viral-derived T cell epitopes (peptides). To further demonstrate that the TCR-like binding specificity is maintained after transforming recombinant Fab fragment into whole IgG molecule, flow cytometry assays were performed. Using the HLA-A2$^+$ JY cells as APCs, the inventors found intensive staining of JY cells loaded with the specific Gag$_{77-85}$ peptide, but no binding was observed when other control peptides were used (FIG. 6B). These results indicate that the whole IgG molecules maintain the specificity of the original Fab antibody Comparative Flow Cytometric Analysis—

The data presented herewith demonstrate the fine and unique specificity of the HLA-A2/Gag-specific Fab or a whole Ab and their ability to detect naturally processed Tax peptide bound to HLA-A2. To demonstrate that ligand recognition sensitivity is improved by using a whole IgG Ab the staining with whole IgG E5 Abs was tested over a broad range of Ab concentration on peptide-pulsed JY cells (FIGS. 7A-B; Table 3 below) and on a broad range of peptide concentrations of the Gag peptide (FIGS. 7C-D; Table 3 below). Both Abs bind the JY cells that present the Gag peptide, but with a different binding pattern. The staining intensity was 25 times stronger with the whole IgG E5 Ab on cells loaded with 50 μM peptide comparing to a Fab E5 Ab.

TABLE 3

Table 3: Quantification of the comparative flow cytometric analysis. Broad range of Ab concentration on peptide pulsed JY cells. JY cells were pulsed with 50 μM of the Gag$_{77-85}$ and interacted with increasing concentrations of E5 Fab Ab or whole IgG E5 Ab from 100 μg/ml antibody to $3.2 \times 10^{-3}$ μg/ml antibody. (data obtained from FIGS. 7A-B); MFI = median fluorescent intensity.

| Concentration of antibody | MFI Fab | MFI IgG |
|---|---|---|
| αHF | 3.62 | 3.57 |
| 100 μg/ml | 17.61 | |
| 50 μg/ml | 15.82 | 37.72 |
| 10 μg/ml | 10.84 | 35.91 |
| 2 μg/ml | 6.38 | 32.41 |
| 0.4 μg/ml | 4.41 | 14.56 |
| 0.08 μg/ml | 3.66 | 7.53 |
| 0.016 μg/ml | | 4.27 |
| $3.2 \times 10^{-3}$ μg/ml | | 3.40 |

TABLE 4

Table 4: Quantification of the flow cytometry analysis using 20 μg/ml of the Fab or whole IgG E5 antibody using decreasing amounts of the Gag$_{77-85}$ peptide loaded on APCs (data obtained from FIGS. 7C-D); MFI = median fluorescent intensity.

| Peptide concentration | MFI Fab | MFI IgG |
|---|---|---|
| 200 μM p280V | 2.89 | 3.09 |
| 200 μM pGAG | 13.12 | 45.09 |
| 100 μM pGAG | 12.71 | 43.64 |
| 12.5 μM pGAG | 5.55 | 17.24 |
| 6.25 μM pGAG | 4.33 | 11.81 |
| 1.56 μM pGAG | 3.62 | 5.55 |
| 0.78 μM pGAG | 3.48 | 4.84 |
| 0.39 μM pGAG | 3.22 | 4.23 |
| 0.19 μM pGAG | 3.11 | 3.67 |
| 0.09 μM pGAG | | 3.39 |

The staining intensity was also dependent on the concentration of the peptide used for pulsing, and peptide concentration at the low μM range was sufficient to detect binding with the whole E5 Ab. Specific ligand detection sensitivity was observed with as low as 4 times lower peptide concentration for the whole E5 IgG Ab. These results demonstrate that the sensitivity of ligand detection by the whole E5 IgG is improved and thus further demonstrated the ability of these high affinity TCR-like Abs to detect the specific Gag MHC-peptide complex on the surface of APCs.

1. Binding of E5 IgG Antibody to T-1 HIV Infected Cells—

T-1 cells were infected with HXB2 virus at multiplicity of infection (MOI) of 1 Infectious Unit (IU)/ml. The efficiency of infection as measured by staining the cells with αp24 Ag$^+$ αMFITC and measured by FACS was 80-100% (data are not shown). The E5 IgG was used for detecting HLA-A2/Gag complexes on virus infected cells. To this end, HLA-A2 negative MT-2 and HLA-A2 positive T-1 cells which are lines of human CD4+ T cells infected with HIV-1 were used. T-1 cells were infected with HXB2 virus at multiplicity of infection (MOI) of 1 Infectious Unit (IU)/ml. The efficiency of infection as measured by staining the cells with αp24 Ag+ αMFITC and measured by FACS was 80-100% (data are not shown). As shown in FIGS. 8A-D, the processing of the Gag$_{77-85}$ epitope and its presentation on the cell-membrane as function of time post infection was determined with purified E5 IgG (5 or 10 μg/ml) by FACS. 17 days post infection a specific staining is observed on the virus infected cells but not on the uninfected cells (FIG. 8C). These results underscore the utility of using TCR-like Abs for the study of Ag presentation on virus-infected cells. In chronic infection, the dominant HLA-A0201-restricted CTL response is directed towards the epitope SLYNTVATL ("SL9"; SEQ ID NO:2) in p17 Gag (residues 77-85). This epitope is targeted by 75% of HLA-A* 0201-positive adults, and the magnitude of this A*0201-SL9 response shows a strong negative association with viral load in progressive infection. Despite using the highly sensitive peptide-major histocompatibility complex tetramer and intracellular cytokine assays, responses to the SL9 epitope were not detectable in any of 11 HLA-A*0201-positive subjects with acute HIV-1 infection even when assays were repeated using the SL9 peptide variant that was encoded by their autologous virus (Dalod, M. et al. 1999, Weak anti-HIV CD8(+) T-cell effector activity in HIV primary infection. J. Clin. Invest 104, 1431-1439; Goulder, P. J. et al. 2001, Substantial differences in specificity of HIV-specific cytotoxic T cells in acute and chronic HIV infection. J. Exp. Med. 193, 181-194).

In this study the present inventors isolated, by phage display, a panel of human recombinant Fab antibody fragments with peptide-specific, MHC-restricted TCR-like reactivity directed toward an HLA-A2-restricted T-cell epitope. These Fabs are derived from a HIV-HLA-A2-restricted $Gag_{77-85}$ SLYNTVATL (SL9) epitope which is by far the most studied. HIV infected HLA-A2 cell lines were specially lysed by A2 restricted CTL. The recombinant antibodies and their capacity to directly detect the specific HLA-A2/Gag T-cell epitope on antigen presenting cells that have complexes formed by naturally occurring active intracellular processing of the antigen was demonstrated. To improve the sensitivity and targeting capabilities of these TCR-like Ab molecules the present inventors changed the format from the single binding site of a Fab to two binding sites of an IgG1. Moreover, by genetic fusion the present inventors armed the TCR-like antibody with a potent toxin and demonstrated that it can serve as a targeting moiety killing APCs loaded cell in a peptide-specific, MHC-restricted manner similar to cytotoxic T-cell Lymphocytes.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text 1. de Haard, H. J. et al. A large non-immunized human Fab fragment phage library that permits rapid isolation and kinetic analysis of high affinity antibodies. Journal of Biological Chemistry 274, 18218-18230 (1999).
2. Brinkmann, U., Pai, L. H., Fitzgerald, D. J., Willingham, M. & Pastan, I. B3(Fv)-Pe38Kdel, A Single-Chain Immunotoxin That Causes Complete Regression of A Human Carcinoma in Mice. Proceedings of the National Academy of Sciences of the United States of America 88, 8616-8620 (1991).
3. Denkberg, G., Cohen, C. J., Segal, D., Kirkin, A. F. & Reiter, Y. Recombinant human single-chain MHC-peptide complexes made from *E-coli* by in vitro refolding: functional single-chain MHC-peptide complexes and tetramers with tumor associated antigens. European Journal of Immunology 30, 3522-3532 (2000).
4. Denkberg, G., Cohen, C. J. & Reiter, Y. Critical role for CD8 in binding of MHC tetramers to TCR: CD8 antibodies block specific binding of human tumor-specific MHC-Peptide tetramers to TCR. Journal of Immunology 167, 270-276 (2001).
5. Cloutier, S. M. et al. Streptabody, a high avidity molecule made by tetramerization of in vivo biotinylated, phage display-selected scFv fragments on streptavidin. Molecular Immunology 37, 1067-1077 (2000).
6. Pastan, I. Targeted therapy of cancer with recombinant immunotoxins. Biochimica et Biophysica Acta-Reviews on Cancer 1333, C1-C6 (1997).
7. Dalod, M. et al. Weak anti-HIV CD8(+) T-cell effector activity in HIV primary infection. J. Clin. Invest 104, 1431-1439 (1999).
8. Goulder, P. J. et al. Substantial differences in specificity of HIV-specific cytotoxic T cells in acute and chronic HIV infection. J. Exp. Med. 193, 181-194 (2001).

What is claimed is:

1. An isolated antibody comprising an antigen recognition domain comprising SEQ ID NO: 3-8 as its six complementarity determining regions (CDRs), wherein the antibody is capable of binding a human MHC molecule being complexed with SEQ ID NO:2, derived from an HIV polypeptide Pr55 (Gag), wherein the antibody does not bind said human MHC molecule in an absence of said complexed peptide and wherein the antibody does not bind said peptide in an absence of said human MHC molecule.

2. A molecule comprising the antibody of claim 1, conjugated to a therapeutic moiety.

3. A molecule comprising the antibody of claim 1, conjugated to a detectable moiety.

4. The isolated antibody of claim 1, being multivalent.

5. The isolated antibody of claim 4, being of an IgG class.

6. A multivalent composition comprising the isolated antibody of claim 1.

7. An isolated polynucleotide comprising a nucleic acid sequence encoding the isolated antibody of claim 1.

8. The isolated polynucleotide of claim 7, wherein said nucleic acid sequence comprises SEQ ID NOs:9-14.

9. A nucleic acid construct comprising the isolated polynucleotide of claim 7 and a promoter for directing expression of said nucleic acid sequence in a host cell.

10. A method of detecting a cell expressing a human immunodeficiency virus (HIV) antigen, comprising contacting the cell with the isolated antibody of claim 1 under conditions which allow immunocomplex formation, wherein a presence or a level above a predetermined threshold of said immunocomplex is indicative of HIV expression in the cell.

11. A method of diagnosing human immunodeficiency virus (HIV) infection in a subject in need thereof, comprising contacting a biological sample of the subject with the isolated antibody of claim 1 under conditions which allow immunocomplex formation, wherein a presence or a level above a pre-determined threshold of said immunocomplex in the biological sample is indicative of HIV-infected cells in the subject, thereby diagnosing HIV infection in the subject.

* * * * *